United States Patent
Ishikawa et al.

(10) Patent No.: US 9,512,075 B2
(45) Date of Patent: Dec. 6, 2016

(54) COMPOUND; TAUTOMER AND GEOMETRIC ISOMER THEREOF; SALT OF SAID COMPOUND, TAUTOMER, OR GEOMETRIC ISOMER; METHOD FOR MANUFACTURING SAID COMPOUND, TAUTOMER, ISOMER, OR SALT; ANTIMICROBIAL AGENT; AND ANTI-INFECTIVE DRUG

(71) Applicants: OKAYAMA UNIVERSITY, Okayama (JP); MICROBIAL CHEMISTRY RESEARCH FOUNDATION, Tokyo (JP); KINKI UNIVERSITY, Osaka (JP)

(72) Inventors: Teruhiko Ishikawa, Okayama (JP); Tatsuya Kitaoka, Okayama (JP); Shyota Katayama, Okayama (JP); Yoshikuni Itoh, Osaka (JP); Ryutaro Utsumi, Nara (JP); Masayuki Igarashi, Tokyo (JP)

(73) Assignees: OKAYAMA UNIVERSITY, Okayama (JP); MICROBIAL CHEMISTRY RESEARCH FOUNDATION, Tokyo (JP); KINKI UNIVERSITY, Osaka (JP)

( * ) Notice: Subject to any disclaimer, the term of this patent is extended or adjusted under 35 U.S.C. 154(b) by 0 days.

(21) Appl. No.: 14/436,316

(22) PCT Filed: Oct. 17, 2013

(86) PCT No.: PCT/JP2013/078233
§ 371 (c)(1),
(2) Date: Apr. 16, 2015

(87) PCT Pub. No.: WO2014/061752
PCT Pub. Date: Apr. 24, 2014

(65) Prior Publication Data
US 2015/0291523 A1   Oct. 15, 2015

(30) Foreign Application Priority Data

Oct. 17, 2012   (JP) .................... 2012-230270

(51) Int. Cl.
C07D 209/34   (2006.01)
C07D 311/56   (2006.01)

(52) U.S. Cl.
CPC .......... *C07D 209/34* (2013.01); *C07D 311/56* (2013.01)

(58) Field of Classification Search
None
See application file for complete search history.

(56) References Cited

U.S. PATENT DOCUMENTS

| 3,122,557 A | 2/1964 | Molho |
| 5,624,951 A | 4/1997 | Yang et al. |
| 5,723,476 A | 3/1998 | Larsen et al. |
| 2004/0176610 A1 | 9/2004 | Poel |
| 2005/0043389 A1 | 2/2005 | Roth et al. |
| 2011/0144355 A1 | 6/2011 | Igarashi et al. |

FOREIGN PATENT DOCUMENTS

| CN | 102217597 A | 10/2011 |
| EP | 2 327 789 A1 | 6/2011 |
| GB | 1539811 | 2/1979 |
| JP | 52-42881 A | 4/1977 |
| JP | 06-501248 A | 2/1994 |
| JP | 06-340649 A | 12/1994 |
| JP | 07-509488 A | 10/1995 |
| JP | 11-349568 A | 12/1999 |
| JP | 2000-500490 A | 1/2000 |
| JP | 2005-533841 A | 11/2005 |
| JP | 2006-515012 A | 5/2006 |
| WO | 92/06083 | 4/1992 |
| WO | 2004/074282 A1 | 9/2004 |

OTHER PUBLICATIONS

Extended European Search Report dated Mar. 8, 2016, mailed by the European Patent Office, for corresponding Patent Application No. EP 13 84 7221.
M. Patricia Jevons, "To-day's Drugs", British Medical Journal, Jan. 14, 1961, pp. 124-125.
DM Sievert, et al., "*Staphylococcus aureus* Resistant to Vancomycin—United States, 2002", Morbidity and Mortality Weekly Report (MMWR), Jul. 5, 2002, pp. 565-567, vol. 51-issue No. 26, Centers for Disease Control and Prevention (CDC), Atlanta, GA, United States.
S. Yu. Shtringol, et al., "The nootropic properties of new 2-oxoindolin-3-glyoxylic acid derivates", Visnik Farmatsii, SciFinder, 2008, pp. 75-77, issue No. 4, Vidavnitstvo NFaU, Ukraine. (With English Abstract).
S. K. Agarwal and R. C. Saxena, "Synthesis, Characterization and Screening of Antibacterial Activity of Some New Mannich Bases", J. Indian Chem. Soc., Dec. 1980, pp. 1240-1241, vol. 57-issue No. 12.
Tyunosin Ukita and Kiichi Arakawa, "Antibacterial Properties of Compounds Containing the Tricarbonylmethane Group. IX. Effects of Nitrogenous Radicals in the Side-chains of 3-Acyl-4-hydroxycoumarins and their Derivatives", 1953, pp. 255-260, vol. 1-issue No. 3.
T. Patonay, et al., "Synthesis, Antibacterial and Antifungal Activity of 4-Hydroxycoumarin Derivatives, Analogs of Novobiocin", Phamazie, 1984, pp. 86-91, vol. 39-issue No. 2.

(Continued)

*Primary Examiner* — Alicia L Otton
(74) *Attorney, Agent, or Firm* — Pergament & Cepeda LLP; Milagros A. Cepeda; Edward D. Pergament

(57) ABSTRACT

The present invention provides compounds belonging to 3-acyloxyindole compounds or 3-acyl-4-hydroxycoumarin compounds, a tautomer or geometric isomer thereof, or a salt thereof and methods for producing the same, which compounds are useful as antibacterial agent and as therapeutic drugs against infectious diseases.

9 Claims, No Drawings

(56) References Cited

OTHER PUBLICATIONS

Byung H. Lee, et al., "Anthelmintic β-Hydroxyketoamindes (BKAS)", Bioorganic and Medicinal Chemistry Letters, 1998, pp. 3317-3320, Elsevier Science Ltd.

Par L. Fontaine, et al., "Activite anti-inflammatoire experimentale de coumarines, indane-doines et acyl-indane diones apparentees aux anticoagulants oraux", Med. Phamacol. exp., 1967, pp. 497-507, vol. 17-issue No. 5.

L. Fontaine, et al., "Etude experimentale des proprietes choleretiques de coumarines, indane-doines et acyl indane diones apparentees aux anticoagulants oraux", Nov.-Dec. 1967, pp. 430-440, issue No. 6.

Pen-Yuan Lin, et al., "Synthesis and Antibacterial Activities of Novel 4-Hydroxy-7-hydroxy- and 3-Carboxycoumarin Derivatives", Molecules, 2012, pp. 10843-10863, vol. 17.

Shipra Baluja, et al., "Antibacterial Studies of Some Metal Complexes of Coumarin Chalcones: Part-II", J. Inst. Chemists (India), 2009, pp. 102-109, vol. 81, Part 4.

Josef Klosa, "Synthese von Derivaten des 6-Methyl-4-oxicumarine", Archiv der Pharmazie, 1956, pp. 156-161, vol. 289.

Josef Klosa, "Synthese von 4-Oxy-6-chlor-curmarin-derivaten", Archiv der Pharmazie, 1956, pp. 143-150, vol. 289.

Trkovnik, et al., "Synthesen von 4-Hydroxycumarinen mit hoheren Monocarbonsauren", Croatica Chemica ACTA, 1968, pp. 91-92, vol. 40.

V V Mulwad and Rupesh B Pawar, "Synthesis of some antibacterial compounds from 4-hydroxycoumarin", Indian Journal of Chemistry, Sep. 2003, pp. 2091-2096, vol. 42B-issue No. 9, New Delhi, India.

International Search Report dated Jan. 21, 2014, for corresponding International Patent Application No. PCT/JP2013/078233. (With English Translation).

International Preliminary Report on Patentability issued Apr. 21, 2015, for corresponding International Patent Application No. PCT/JP2013/078233.

Written Opinion dated Jan. 21, 2014, for corresponding International Patent Application No. PCT/JP2013/078233. (With English Translation).

COMPOUND; TAUTOMER AND GEOMETRIC ISOMER THEREOF; SALT OF SAID COMPOUND, TAUTOMER, OR GEOMETRIC ISOMER; METHOD FOR MANUFACTURING SAID COMPOUND, TAUTOMER, ISOMER, OR SALT; ANTIMICROBIAL AGENT; AND ANTI-INFECTIVE DRUG

This application is a National Phase application under 35 U.S.C. 371 of International Application No. PCT/JP2013/078233, filed on Oct. 17, 2013, which claims priority to Japanese application No. 2012-230270, filed on Oct. 17, 2012, all of which are hereby incorporated by reference in their entireties.

TECHNICAL FIELD

The present invention relates to a compound belonging to 3-acyloxyindole compounds or 3-acyl-4-hydroxycoumarin compounds, a tautomer or geometric isomer thereof, or a salt thereof; a method for producing the same; an antibacterial agent; and an infectious disease therapeutic drug. The present invention also relates to an antibacterial compound having antibacterial effects and belonging to 3-acyloxyindole compounds or 3-acyl-4-hydroxycoumarin compounds, or a salt thereof; a method for producing the same; an antibacterial agent; and an infectious disease therapeutic drug.

BACKGROUND ART

Since the practical use of the first antibiotic penicillin G in 1940, many antibacterial agents have been developed, and antibacterial chemotherapy has greatly contributed to the advance of modern medicine and the extension of the average lifetime. However, pathogenic bacteria have acquired resistance to such antibacterial agents one after another, and the effects of antibacterial chemotherapy have considerably decreased in the 21st century (see NPL 1). In particular, in 1960 in the United Kingdom, methicillin-resistant *S. aureus* (MRSA), which acquired resistance to all β-lactam antibacterial agents, appeared from *Staphylococcus aureus* (*S. aureus*) which is a pathogenic bacterium mainly causing hospital infection (see NPL 2). Since then, the number of MRSA has continued to increase up to the present, so that it has spread all over the world today. It is not too much to say that there are no hospitals without MRSA.

There are many types of antibacterial agents. Thus, even when one type of antibacterial agent is ineffective to an infectious disease, the infectious disease can be cured using another type of antibacterial agent having a different action mechanism. Pathogenic bacteria, however, have continued to acquire resistance to each of the antibacterial agents. As a result, by the end of the 20th century, multiply antibiotic-resistant bacteria appeared which acquired resistance to almost all currently-available antibacterial agents. Typical examples of the multiply antibiotic-resistant bacteria include MRSA as Gram-positive bacteria, *Acinetobacter* as Gram-negative bacteria, and tuberculosis bacteria as acid-fast bacteria.

Vancomycin was an only antibacterial agent that maintained its effectiveness to multiply antibiotic-resistant bacteria. However, there has currently appeared vancomycin-resistant *Enterococcus* (VRE) and the like that acquired drug resistance to vancomycin, which needs sufficient care to be taken in using vancomycin.

Therefore, keen demand has arisen for the provision of a novel compound which exhibits a low antibacterial activity against bacteria acquiring no drug resistance and thus does not permit them to become drug resistant and which exhibits an excellent antibacterial activity against drug-resistant bacteria resistant to at least one drug such as vancomycin (see NPL 3).

Also, there have recently been problems with infectious diseases caused by bacteria belonging to the genus *Clostridium*, which are pathogenic enterobacteria. Bacteria belonging to the genus *Clostridium* have characteristics that they are positive in Gram staining, obligately anaerobic, and form spores. Some of the bacteria belonging to the genus *Clostridium* are present as normal bacterial flora within the intestine of a human and animals, and pathogenic bacteria are also present there. Among them, there have been problems with infectious diseases such as colitis caused by *Clostridium difficile* and *Clostridium perfringens*.

More than 400 kinds of enterobacteria reside in the intestine of a healthy human in a well-balanced manner. When an antibacterial agent is administered against the intestinal flora (intestinal normal bacterial flora) formed by these enterobacteria, the balance of the intestinal flora is broken, so that *Clostridium difficile* originally existing in the intestine proliferate abnormally due to microbial substitution to produce toxin in the large intestine. Also, *Clostridium difficile* is propagated from the developed patients directly or via medical staff in hospitals. Abnormal proliferation of *Clostridium difficile* not only causes severe diarrhea in patients but also often causes them to die. 20% to 30% of the cases of diarrhea and 90% of the cases of pseudomembranous enterocolitis accompanied by use of antibacterial agents for patients in hospitals are due to abnormal proliferation of *Clostridium difficile*. Infectious diseases caused by *Clostridium difficile* are characterized by being high in morbidity rate and death rate.

In many advanced countries such as the United States of America, Canada, and Europe, hospital infection caused by *Clostridium difficile* has become serious problems. For example, only in the United States of America, about 700,000 cases occur in a year, and economic impact relating to this infectious disease is as much as 3.2 billion dollars per year. In member states of the EU, medical care cost relating to it is estimated to be 4.4 billion dollars in a year. In Japan, although infection of *Clostridium difficile* is not usually tested, it is considered that there are many potentially infected individuals.

Almost all antibacterial agents do not effectiveness to *Clostridium difficile* and in that sense, *Clostridium difficile* can also be said to be one of the multiply antibiotic-resistant bacteria. There are only vancomycin and metronidazole used today as therapeutic drugs against infectious diseases caused by *Clostridium difficile*, and there has been a serious problem with reoccurrence upon withdrawal of the drugs. Drug resistance thereto will become a problem eventually, and at present it has strongly been desired to develop a novel compound having novel antibacterial activity against *Clostridium difficile*.

SUMMARY OF INVENTION

Technical Problem

The present invention aims to solve the above existing problems and achieve the following objects. That is, an object of the present invention is to provide a compound belonging to 3-acyloxyindole compounds or 3-acyl-4-hydroxycoumarin compounds, a tautomer or geometric isomer thereof, or a salt thereof. Another object of the present invention is to provide a method for efficiently producing the compound, the tautomer or geometric isomer, or the salt thereof. Another object of the present invention is to provide an excellent antibacterial agent containing the compound, the tautomer or geometric isomer thereof, or the salt thereof. Also, another object of the present invention is to provide an infectious disease therapeutic drug containing the antibacterial agent. Also, another object of the present invention is to provide: an antibacterial compound having antibacterial effects and belonging to 3-acyloxyindole compounds or 3-acyl-4-hydroxycoumarin compounds, or a salt thereof; a method for efficiently producing the same; an excellent antibacterial agent containing the antibacterial compound or salt thereof; and an infectious disease therapeutic drug containing the antibacterial agent.

Solution to Problem

The present inventors conducted extensive studies in order to solve the above problems and have obtained the following findings. That is, they have found that compounds belonging to 3-acyloxyindole compounds or 3-acyl-4-hydroxycoumarin compounds of the present invention have antibacterial activity and have further found that these compounds include many compounds having antibacterial activity against MRSA, VRE, or *Clostridium difficile*, or any combination thereof, which are multiply antibiotic-resistant bacteria. The present invention has been accomplished on the basis of these findings.

The present invention is based on the above findings obtained by the present invention, and means for solving the above problems are as follows.

In one aspect, the present invention provides a compound represented by any one of General Formulas (1) to (3) below, a tautomer or geometric isomer thereof, or a salt thereof:

General Formula (1)

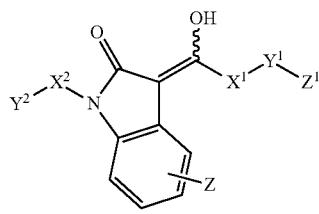

AI

General Formula (2)

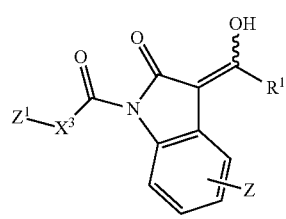

AII

General Formula (3)

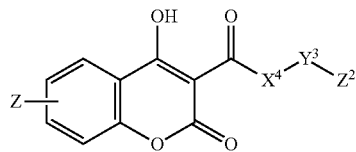

B where in the General Formulas (1) to (3),
$X^1$ represents a single bond or an alkylene group having 1 to 8 carbon atoms,
$Y^1$ represents a single bond, —O—, —NHCO—, —NHCOO—, —S—, —SO—, or —SO$_2$—,
$Z^1$ represents a cyclic, linear, or branched alkyl group which has 8 to 30 carbon atoms and may have a halogen atom,
$X^2$ represents a single bond, —CO—, —CONH—, or —COO—, $Y_2$ represents a hydrocarbon group which has 1 to 30 carbon atoms and may have —CN, —NO$_2$, an alkoxy group, a halogen atom, or any combination thereof; or a hydrogen atom,
$Z^2$ represents a hydrocarbon group which has 5 to 30 carbon atoms and may have a halogen atom,
$X^3$ represents a single bond or —NH—,
$Y^3$ represents —O—, —NH—, —NHCO—, —NHCOO—, —S—, —SO—, or —SO$_2$—,
$X^4$ represents an alkylene group having 1 to 8 carbon atoms,
Z represents a hydrogen atom, a halogen atom, an alkoxy group having 1 to 6 carbon atoms, or a hydrocarbon group having 1 to 20 carbon atoms, and
$R^1$ represents a hydrocarbon group which has 1 to 30 carbon atoms and may have an alkoxy group, —OH, —CN, —NO$_2$, a halogen atom, or any combination thereof.

In one aspect, the present invention provides an antibacterial compound represented by General Formula (4) or (5) below, or a salt thereof:

General Formula (4)

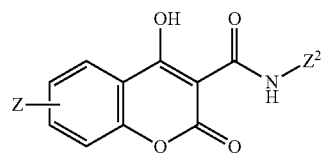

BI

General Formula (5)

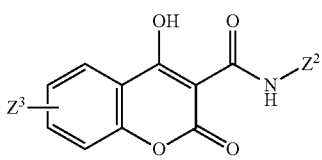

BII where in the General Formulas (4) and (5),
Z represents a hydrogen atom, a halogen atom, an alkoxy group having 1 to 6 carbon atoms, or a hydrocarbon group having 1 to 20 carbon atoms,
$Z^2$ represents a hydrocarbon group which has 5 to 30 carbon atoms and may have a halogen atom, and
$Z^3$ represents a halogen atom, an alkoxy group having 1 to 6 carbon atoms, or a hydrocarbon group having 1 to 20 carbon atoms.

In one variant, the present invention provides a method for producing the compound represented by any one of General Formulas (1) to (3), the tautomer or geometric isomer thereof, or the salt thereof according to the present invention, the method including:

mixing and reacting an oxyindole compound represented by General Formula (6) or (7) below or a 4-hydroxy-coumarin compound represented by General Formula (8) below with a carboxylic acid in an organic solvent in the presence of a condensation agent and an amine base, where in the General Formulas (6) to (8), General Formula (6)

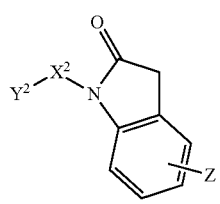

Aa

General Formula (7)

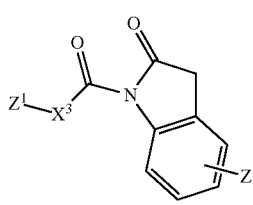

Ab

General Formula (8)

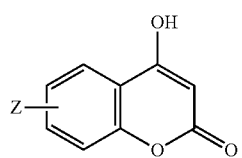

Ba $Z^1$ represents a cyclic, linear, or branched alkyl group which has 8 to 30 carbon atoms and may have a halogen atom, $X^2$ represents a single bond, —CO—, —CONH—, or —COO—, $Y^2$ represents a hydrocarbon group which has 1 to 30 carbon atoms and may have —CN, —NO$_2$, an alkoxy group, a halogen atom, or any combination thereof; or a hydrogen atom, $X^3$ represents a single bond or —NH—, and Z represents a hydrogen atom, a halogen atom, an alkoxy group having 1 to 6 carbon atoms, or a hydrocarbon group having 1 to 20 carbon atoms.

In one variant, the present invention provides a method for producing the compound represented by any one of General Formulas (1) to (3), the tautomer or geometric isomer thereof, or the salt thereof according to the present invention, the method including:

mixing and reacting an oxyindole compound represented by General Formula (6) or (7) below or a 4-hydroxy-coumarin compound represented by General Formula (8) below with a carboxylic acid chloride in an organic solvent in the presence of an amine base, General Formula (6)

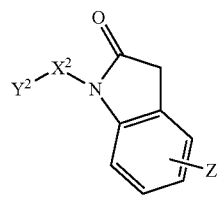

Aa

General Formula (7)

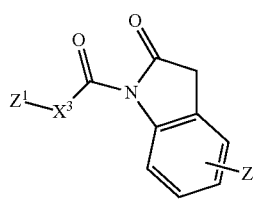

Ab

General Formula (8)

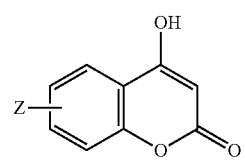

Ba where in the General Formulas (6) to (8), $Z^1$ represents a cyclic, linear, or branched alkyl group which has 8 to 30 carbon atoms and may have a halogen atom, $X^2$ represents a single bond, —CO—, —CONH—, or —COO—, $Y^2$ represents —CN, —NO$^2$, a hydrocarbon group which has 1 to 30 carbon atoms and may have an alkoxy group, a halogen atom, or both thereof; or a hydrogen atom, $X^3$ represents a single bond or —NH—, and Z represents a hydrogen atom, a halogen atom, an alkoxy group having 1 to 6 carbon atoms, or a hydrocarbon group having 1 to 20 carbon atoms.

In one variant, the present invention provides a method for producing the compound represented by any one of General Formulas (1) to (3), the tautomer or geometric isomer thereof, or the salt thereof according to the present invention, the method including:

mixing and reacting an oxyindole compound represented by General Formula (6) or (7) below or a 4-hydroxy-coumarin compound represented by General Formula (8) below with a carboxylic anhydride in an organic solvent in the presence of an amine base, General Formula (6)

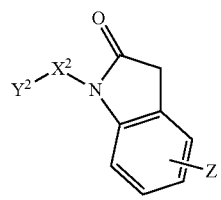

Aa

General Formula (7)

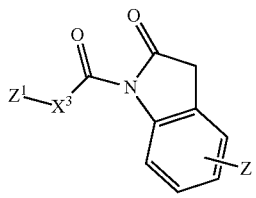

General Formula (8)

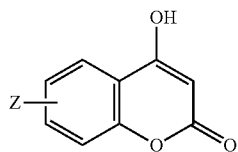

where in the General Formulas (6) to (8),

Z¹ represents a cyclic, linear, or branched alkyl group which has 8 to 30 carbon atoms and may have a halogen atom, X² represents a single bond, —CO—, —CONH—, or —COO—, Y² represents —CN, —NO$_2$, a hydrocarbon group which has 1 to 30 carbon atoms and may have an alkoxy group, a halogen atom, or both thereof; or a hydrogen atom, X³ represents a single bond or —NH—, and Z represents a hydrogen atom, a halogen atom, an alkoxy group having 1 to 6 carbon atoms, or a hydrocarbon group having 1 to 20 carbon atoms.

In one variant, the present invention provides a method for producing the antibacterial compound represented by General Formula (5) or the salt thereof according to the present invention, the method including:

mixing and reacting a 4-hydroxycoumarin compound represented by General Formula (8) below with a carboxylic acid in an organic solvent in the presence of a condensation agent and an amine base, General Formula (8)

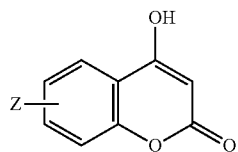

where in the General Formula (8),

Z represents a hydrogen atom, a halogen atom, an alkoxy group having 1 to 6 carbon atoms, or a hydrocarbon group having 1 to 20 carbon atoms.

In one variant, the present invention provides a method for producing the antibacterial compound represented by General Formula (4) or the salt thereof according to the present invention, the method including:

mixing and reacting a 4-hydroxycoumarin compound represented by General Formula (8) below with an isocyanate in an organic solvent in the presence of an amine base, General Formula (8)

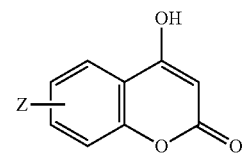

where in the General Formula (8),

Z represents a hydrogen atom, a halogen atom, an alkoxy group having 1 to 6 carbon atoms, or a hydrocarbon group having 1 to 20 carbon atoms.

In one variant, the present invention provides an antibacterial agent, including:

the compound represented by any one of the General Formulas (1) to (3), the tautomer or geometric isomer thereof, or the salt thereof according to the present invention.

In one variant, the present invention provides an antibacterial agent, including:

the antibacterial compound represented by General Formulas (4) to (5), or the salt thereof according to the present invention.

In one variant, the present invention provides an infectious disease therapeutic drug, including:

the antibacterial agent, represented by any one of General Formulas (1) to (3), the tautomer or geometric isomer thereof, or the salt thereof according to the present invention, the antibacterial agent represented by General Formulas (4) or (5), or a salt thereof according to the present invention, or both thereof.

Advantageous Effects of Invention

The compound, the tautomer or geometric isomer thereof, or the salt thereof of the present invention can solve the above existing problems, and it is possible to provide the compound belonging to 3-acyloxyindole compounds or 3-acyl-4-hydroxycoumarin compounds, the tautomer or geometric isomer thereof, or the salt thereof.

The antibacterial compound or the salt thereof of the present invention can solve the above existing problems, and it is possible to provide the antibacterial compound having antibacterial effects and belonging to 3-acyloxyindole compounds or 3-acyl-4-hydroxycoumarin compounds, or the salt thereof.

The method for producing the compound or the antibacterial compound of the present invention can solve the above existing problems, and it is possible to provide the method for efficiently producing the compound, the tautomer or geometric isomer thereof, or the salt thereof; or the antibacterial compound or the salt thereof.

The antibacterial agent of the present invention can solve the above existing problems, and it is possible to provide the excellent antibacterial agent containing the compound, the tautomer or geometric isomer thereof, or the salt thereof; or the antibacterial compound or the salt thereof.

The infectious disease therapeutic drug of the present invention can solve the above existing problems, and it is possible to provide the excellent infectious disease therapeutic drug containing the antibacterial agent.

DESCRIPTION OF EMBODIMENTS

Compound, Tautomer or Geometric Isomer Thereof, or Salt Thereof; or Antibacterial Compound or Salt Thereof The compound of the present invention is a novel compound represented by any one of General Formulas (1) to (3) below and an antibacterial compound represented by General Formula (4) or (5) below. The novel compound represented by any one of General Formulas (1) to (3) below and the antibacterial compound represented by General Formula (4) or (5) below each compounds belonging to 3-acyloxy-indole compounds and 3-acyl-4-hydroxycoumarin compounds. Hereinafter, the compound represented by General Formula (1) may be referred to as compound AI, the compound represented by General Formula (2) may be referred to as compound AII, the compound represented by General Formula (3) may be referred to as compound B, the compound represented by General Formula (4) may be referred to as compound BI, and the compound represented by General Formula (5) may be referred to as compound BII.

General Formula (1)

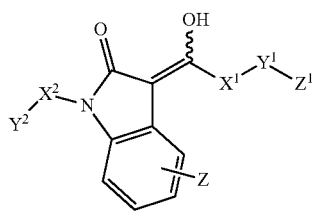

AI

General Formula (2)

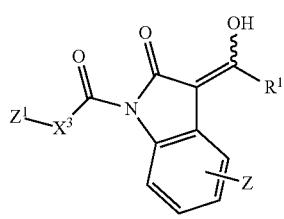

AII

General Formula (3)

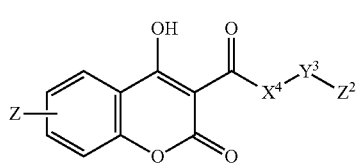

B

General Formula (4)

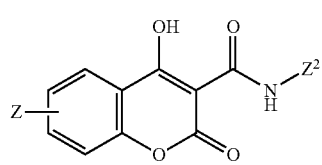

BI

General Formula (5)

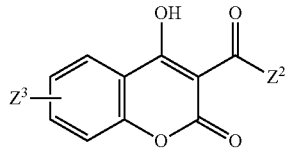

BII

In the General Formulas (1) to (5),
$X^1$ represents a single bond or an alkylene group having 1 to 8 carbon atoms,
$Y^1$ represents a single bond, —O—, —NHCO—, —NHCOO—, —S—, —SO—, or —SO$_2$—,
$Z^1$ represents a cyclic, linear, or branched alkyl group which has 8 to 30 carbon atoms and may have a halogen atom,
$X^2$ represents a single bond, —CO—, —CONH—, or —COO—,
$Y^2$ represents a hydrocarbon group which has 1 to 30 carbon atoms and may have —CN, —NO$_2$, an alkoxy group, a halogen atom, or any combination thereof; or a hydrogen atom,
$Z^2$ represents a hydrocarbon group which has 5 to 30 carbon atoms and may have a halogen atom,
$X^3$ represents a single bond or —NH—,
$Y^3$ represents —O—, —NH—, —NHCO—, —NHCOO—, —S—, —SO—, or —SO$_2$—,
$X^4$ represents an alkylene group having 1 to 8 carbon atoms,
Z represents a hydrogen atom, a halogen atom, an alkoxy group having 1 to 6 carbon atoms, or a hydrocarbon group having 1 to 20 carbon atoms,
$R^1$ represents a hydrocarbon group which has 1 to 30 carbon atoms and may have an alkoxy group, —OH, —CN, —NO$_2$, a halogen atom, or any combination thereof, and
$Z^2$ represents a hydrocarbon group which has 5 to 30 carbon atoms and may have a halogen atom.

Among the compounds represented by the General Formulas (1) to (3), any of the below-described aspects (i) to (iii) is preferable.

The aspect (i) is an aspect where, in the General Formulas (1) to (3), $X^1$ and $X^4$ each are a methylene group, $X^2$ is —CO— or —CONH—, $X^3$ is a single bond, $Y^1$ and $Y^3$ each are —O—, $Y^2$ is a methyl group, or a phenyl group which may have, as a substituent, an alkoxy group, a trifluoromethyl group, a halogen atom, or any combination thereof, Z is a hydrogen atom, a methyl group, or a halogen atom, and $Z^1$ and $Z^2$ each are a cyclic, linear, or branched alkyl group having 8 to 12 carbon atoms.

Z is preferably a hydrogen atom or a halogen atom.

The halogen atom is not particularly limited and may be appropriately selected depending on the intended purpose. Examples thereof include a fluorine atom, a chlorine atom, and a bromine atom.

The aspect (ii) is an aspect where, in the General Formulas (1) to (3), $X^1$ and $X^4$ each are a methylene group, $X^2$ is —CO— or —CONH—, $X^3$ is a single bond, $Y^1$ and $Y^3$ each are —S—, $Y^2$ is a methyl group, or a phenyl group which may have, as a substituent, an alkoxy group, a trifluoromethyl group, a halogen atom, or any combination thereof, Z is a hydrogen atom, a methyl group, or a halogen atom, and $Z^1$ and $Z^2$ each are a cyclic, linear, or branched alkyl group having 8 to 12 carbon atoms.

Z is preferably a hydrogen atom or a halogen atom.

The halogen atom is not particularly limited and may be appropriately selected depending on the intended purpose. Examples thereof include a fluorine atom, a chlorine atom, and a bromine atom.

The aspect (iii) is an aspect where, in the General Formulas (1) to (3), $X^1$, $X^3$, and $Y^1$ each are a single bond, $X^2$ is —CO— or —CONH—, $X^4$ is a methylene group, $Y^3$ is —O— or —S—, $Y^2$ is a methyl group, or a phenyl group which may have, as a substituent, an alkoxy group, a trifluoromethyl group, a halogen atom, or any combination thereof, Z is a hydrogen atom, a methyl group, or a halogen atom, and $Z^1$ and $Z^2$ each are a cyclic, linear, or branched alkyl group having 8 to 12 carbon atoms.

Z is preferably a hydrogen atom or a halogen atom.

The halogen atom is not particularly limited and may be appropriately selected depending on the intended purpose. Examples thereof include a fluorine atom, a chlorine atom, and a bromine atom.

Specific examples of $Z^3$ in the compounds represented by the General Formulas (4) and (5) include a methyl group, a fluorine atom, a chlorine atom, and a bromine atom.

Whether the compounds AI, AII and B and the antibacterial compounds BI and BII have the structures represented by the General Formulas (1) to (5) can be confirmed by various analysis methods appropriately selected. For example, it can be confirmed by performing analysis with nuclear magnetic resonance spectroscopy.

The compounds AI and AII have tautomers and geometric isomers thereof, and thus such tautomers and geometric isomers are also included in the compounds AI and AII. Examples of the tautomers and geometric isomers include those having structures represented by Chemical Formula (1) below. The compounds AI and AII can have several kinds of structural patterns as shown and exist in a state where they are not fixed as a certain state.

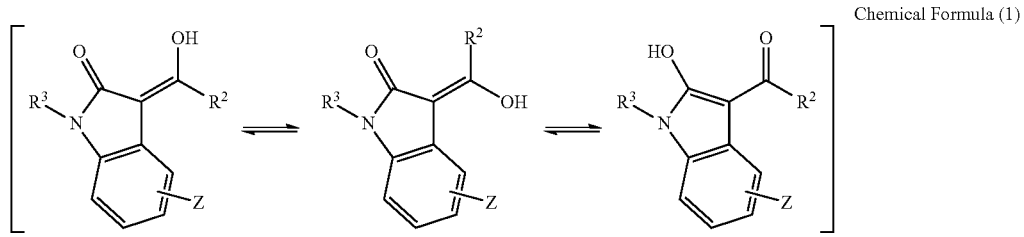

Chemical Formula (1)

In the Chemical Formula (1), $R^2$ and $R^3$ each are any substituent.

Also, the compounds AI, AII and B and the antibacterial compounds BI and BII, and the tautomers and the geometric isomers of the compounds AI and AII may be in the form of salt. The salt is not particularly limited and may be appropriately selected depending on the intended purpose. Examples thereof include: alkali metal salts formed with, for example, sodium and potassium; alkaline earth metal salts formed with, for example, calcium and magnesium; and organic amine salts formed with, for example, methylamine, ethylamine, and diethanolamine.

Methods for producing the compounds AI, AII and B and the antibacterial compounds BI and BII, and the tautomers and the geometric isomers of the compounds AI and AII, or the salts thereof are not particularly limited and can be performed by routine methods. In particular, the compounds AI, AII and B and the antibacterial compounds BI and BII, and the tautomers and the geometric isomers of the compounds AI and AII, or the salts thereof are preferably obtained by the below-described methods of the present invention for producing a compound, a tautomer or geometric isomer thereof, or a salt thereof; or an antibacterial compound or a salt thereof.

The compounds AI, AII and B and the antibacterial compounds BI and BII, and the tautomers and the geometric isomers of the compounds AI and AII, or the salts thereof have excellent antibacterial activity as described below. Therefore, the compounds AI, AII and B and the antibacterial compounds BI and BII, and the tautomers and the geometric isomers of the compounds AI and AII, or the salts thereof can suitably be used as active ingredients of the below-described antibacterial agent of the present invention.

Also, in the aspect (iii), $R^1$ is preferably a methyl group, an alkoxymethyl group, or a phenyl group which may have, as a substituent, a hydroxyl group, a fluorine atom, a chlorine atom, a bromine atom, or any combination thereof.

The cyclic alkyl group having 8 to 12 carbon atoms or the linear or branched alkyl group for $Z^1$ and $Z^2$ in any of the aspects (i) to (iii) is not particularly limited and may be appropriately selected depending on the intended purpose. It is preferably a n-octyl group, a n-nonyl group, a n-decyl group, a n-undecyl group, a n-dodecyl group, or a 4-butylcyclohexyl group.

$Y^2$ in any of the aspects (i) to (iii) is not particularly limited and may be appropriately selected depending on the intended purpose. Examples thereof include a methyl group, a phenyl group, a 4-methoxyphenyl group, a 4-chlorophenyl group, a 4-fluorophenyl group, a 4-bromophenyl group, a (4-trifluoromethyl)phenyl group, and a 4-trifluoromethoxyphenyl group.

$R^1$ in any of the aspects (i) to (iii) is not particularly limited and may be appropriately selected depending on the intended purpose. Examples thereof include a methyl group, a methoxymethyl group, a phenyl group, a 4-methoxyphenyl group, a 4-chlorophenyl group, a 4-fluorophenyl group, a 4-bromophenyl group, and a 2-hydroxyphenyl group.

Specific examples of Z in the compounds represented by the General Formulas (4) and (5) include a hydrogen atom, a methyl group, a fluorine atom, a chlorine atom, and a bromine atom.

Regarding specific examples of the hydrocarbon group which has 5 to 30 carbon atoms and may have a halogen atom for $Z^2$ in the compounds represented by the General Formulas (4) and (5), it is preferably a cyclic alkyl group having 8 to 12 carbon atoms, and a linear or branched alkyl group, more preferably a n-octyl group, a n-nonyl group, a n-decyl group, a n-undecyl group, a n-dodecyl group, or a 4-butylcyclohexyl group.

<Compounds AI and AII>

The compounds AI and AII are 3-acyloxyindole compounds and are represented by the General Formulas (1) and (2), respectively.

Examples of the compounds AI and AII include 3-acyloxyindole compounds expressed by Structural Formulas (1) to (60) below.

Structural Formula (1)

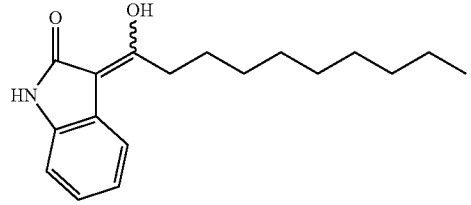

A001 (3-decanoyl-2-oxyindole)

1H NMR (300 Hz) 0.88 (t, 3H, J=6.6 Hz), 1.18-1.52 (m, 12H), 1.71-1.86 (m, 2H), 2.74 (t, 2H, J=7.5 Hz), 7.32 (d, 1H, J=7.5 Hz), 6.98-7.36 (m, 3H), 9.48-9.68 (br, 1H)

13C NMR (75 Hz) 14.1, 22.6, 25.9, 29.2, 29.3, 29.39, 29.45, 31.8, 33.9, 101.6, 110.5, 119.9, 121.98, 122.47, 125.2, 136.3, 173.2, 178.1

Structural Formula (2)

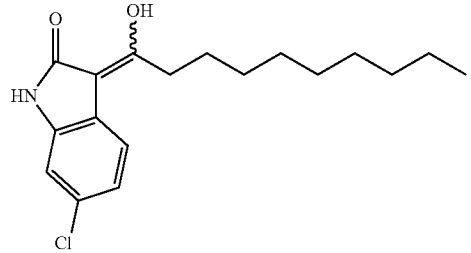

A002 (3-decanoyl-6-chloro-2-oxyindole)

1H NMR (300 Hz) 0.88 (t, 3H, J=6.6 Hz), 1.16-1.83 (m, 14H), 2.36 (t, 2H, J=7.5 Hz), 6.82-7.35 (m, 3H), 8.92-9.29 (br, 1H)

Structural Formula (3)

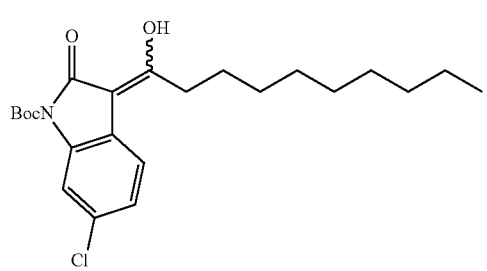

In the Structural Formula (3), Boc represents a tert-butoxycarbonyl group (the same applies hereinafter).

A003 (N-Boc-3-decanoyl-6-chloro-2-oxyindole)

1H NMR (300 Hz) 0.88 (t, 3H, J=6.9), 1.22-1.52 (m, 14H), 1.67 (s, 9H), 2.73 (t, 2H, J=7.5 Hz), 7.15-2.27 (m, 2H), 8.00 (d, 1H, J=1.8 Hz)

Structural Formula (4)

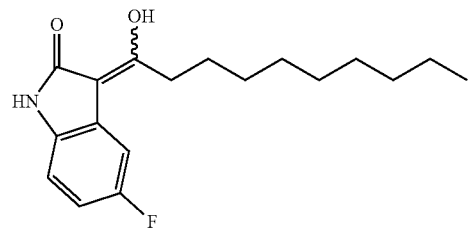

A004 (3-decanoyl-5-fluoro-2-oxyindole)

1H NMR (300 Hz) 0.87 (t, 3H, J=6.6), 1.15-1.82 (m, 14H), 2.34 (t, 2H, 7.5 Hz), 6.79-7.04 (m, 3H), 9.48-9.67 (br, 1H)

Structural Formula (5)

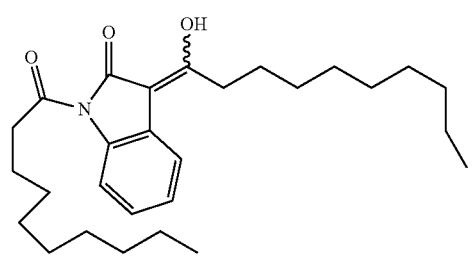

A005 (1,3-didecanoyl-2-oxyindole)

1H NMR (300 Hz) 0.88 (t, 6H, J=6.9 Hz), 1.13-1.86 (m, 28H), 2.35 (t, 2H, J=7.2 Hz), 2.77 (t, 2H, J=7.2 Hz), 6.97-7.39 (m, 4H), 9.39-9.82 (br, 1H)

13C NMR (75 Hz) 14.1, 22.6, 24.7, 25.9, 29.1, 29.2, 29.33, 29.37, 29.44, 31.8, 33.9, 34.1, 101.5, 110.7, 119.9, 122.2, 122.4, 125.3, 136.1, 173.3, 178.5, 179.9

Structural Formula (6)

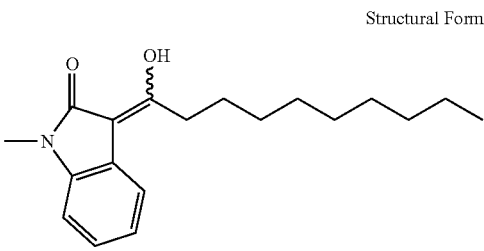

A007 (N-methyl-3-decanoyl-2-oxyindole)

1H NMR (300 Hz) 0.86 (t, 3H, J=6.3 Hz), 1.12-1.82 (m, 14H), 2.72 (t, 2H, 7.8 Hz), 3.34 (s, 3H), 6.94 (d, 1H, J=7.8 Hz), 7.05-7.28 (m, 2H), 7.34 (d, 1H, J=7.8 Hz)

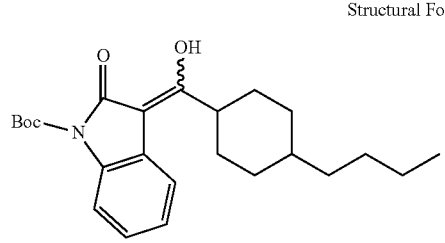

A008
(N-Boc-3-(4-butylcyclohexylcarbonyl)-2-oxyindole)

1H NMR (300 Hz) 0.91 (t, 3H, J=6.9 Hz), 0.98-1.99 (m, 15H), 1.65 (s, 9H), 2.85-2.94 (m, 1H), 7.17-7.36 (m, 3H), 7.92 (d, 1H, J=7.8 Hz)

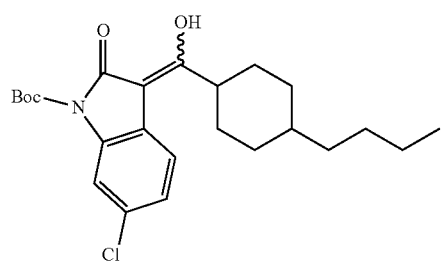

A009 (N-Boc-3-(4-butylcyclohexylcarbonyl)-6-chloro-2-oxyindole)

1H NMR (300 Hz) 0.90 (t, 3H, J=6.9 Hz), 0.96-1.80 (m, 12H), 1.67 (s, 9H), 1.88-1.98 (m, 3H), 2.85 (t, 1H, 2.7 Hz), 7.14-7.22 (m, 2H), 7.99 (d, 1H, 1.8 Hz)

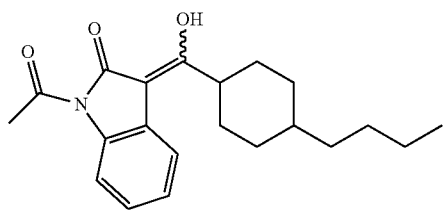

A010 (N-acetyl-3-(4-butylcyclohexylcarbonyl)-2-oxyindole)

1H NMR (300 Hz) 0.91 (t, 3H, J=6.9 Hz), 0.99-2.02 (m, 15H), 2.75 (s, 3H), 2.85-2.98 (m, 1H), 7.16-7.37 (m, 3H), 8.32 (dd, 1H, J=1.8, 7.8 Hz)
13C NMR (75 MHz) 14.1, 22.9, 27.0, 28.33, 38.35, 29.0, 32.6, 36.9, 42.6, 99.8, 116.5, 119.3, 122.5, 124.8, 125.7, 135.1, 170.7, 172.6, 183.5

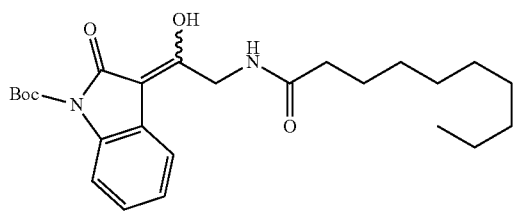

A011 (N-Boc-3-decanoylaminoacetyl-2-oxyindole)

1H NMR (300 Hz) 0.86 (t, 3H, J=6.9 Hz), 0.99-1.80 (m, 14H), 1.64 (s, 9H), 2.20-2.40 (m, 2H), 4.50-4.65 (bs, 2H), 6.40-6.52 (br, 1H), 7.12-8.05 (m, 3H)

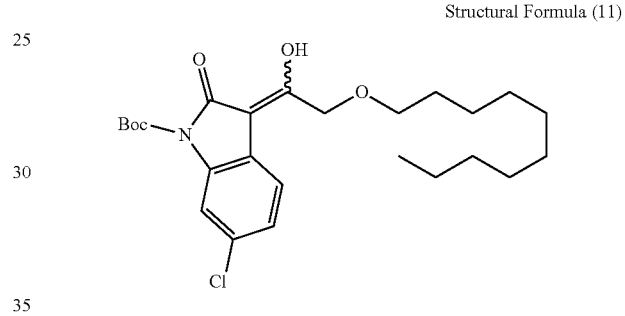

A012
(N-Boc-3-decyloxyacetyl-6-chloro-2-oxyindole)

1H NMR (300 Hz) 0.87 (t, 3H, J=6.9 Hz), 1.16-1.73 (m, 16H), 1.67 (s, 9H), 3.56 (t, 2H, J=6.6 Hz), 4.49 (s, 2H), 7.09-7.44 (m, 2H), 7.97 (d, 1H, J=1.8 Hz)

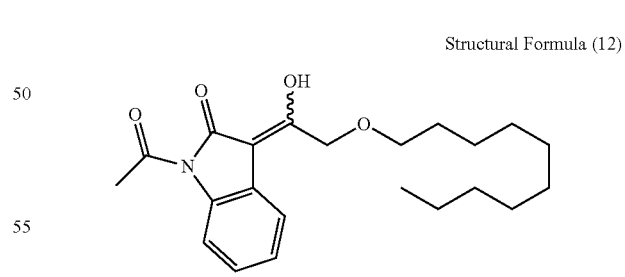

A013 (N-acetyl-3-decyloxyacetyl-2-oxyindole)

1H NMR (300 Hz) 0.87 (t, 3H, J=6.9 Hz), 1.02-1.78 (m, 16H), 2.76 (s, 3H), 3.60 (t, 2H, J=6.9 Hz), 4.54 (s, 2H), 7.17-7.32 (m, 2H), 7.43 (dd, 1H, J=2.0, 7.2 Hz), 8.30 (d, 1H, J=7.8 Hz)

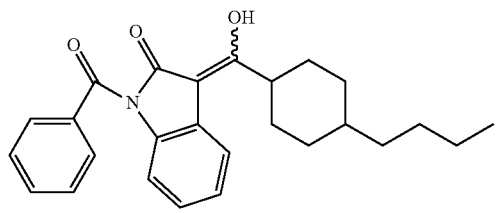

A014 (N-benzoyl-3-(4-butylcyclohexylcarbonyl)-2-oxyindole)

1H NMR (300 Hz) 0.91 (t, 3H, J=6.9 Hz), 1.00-2.07 (m, 15H), 2.93-2.98 (m, 1H), 7.21-8.00 (m, 9H)

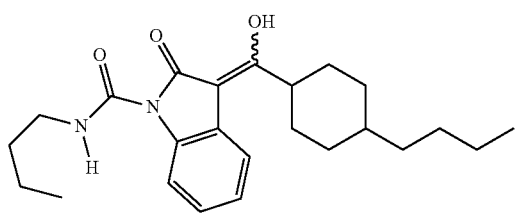

A015 (N-(butylaminocarbonyl)-3-(4-butylcyclohexylcarbonyl)-2-oxyindole)

1H NMR (300 Hz) 0.91 (t, 3H, J=6.9 Hz), 0.93 (t, 3H, J=6.9 Hz), 1.20-2.06 (m, 19H), 2.94-3.00 (m, 1H), 3.37-3.46 (m, 2H), 7.15-7.39 (m, 3H), 8.40 (d, 1H, 7.8 Hz), 8.56-8.78 (br, 1H), 13.50 (s, 1H)

13C NMR (75 Hz) 13.7, 14.1, 20.1, 22.9, 28.4, 29.1, 31.6, 32.6, 36.8, 36.9, 40.0, 42.7, 100.1, 116.3, 119.3, 121.5, 124.0, 125.7, 136.0, 152.2, 172.6, 183.6

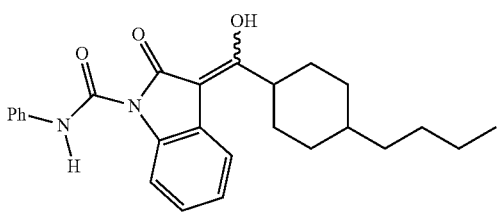

A016 (N-(phenylaminocarbonyl)-3-(4-butylcyclohexylcarbonyl)-2-oxyindole)

1H NMR (300 Hz) 0.91 (t, 3H, J=6.9 Hz), 0.98-2.13 (m, 15H), 2.95-3.02 (m, 1H), 7.07-7.44 (m, 6H), 7.61 (dd, 2H, J=2.1, 6.9 Hz), 8.44 (d, 1H, J=7.8 Hz), 10.78 (s, 1H), 13.40 (s, 1H)

13C NMR (75 Hz) 14.1, 22.9, 28.3, 28.4, 29.0, 32.5, 36.9, 42.8, 100.0, 110.3, 116.4, 119.3, 120.4, 121.6, 124.3, 125.9, 129.0, 135.4, 137.3, 149.4, 172.5, 184.3

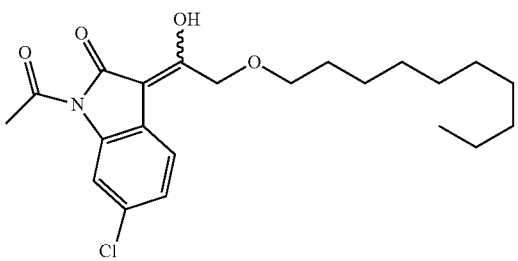

A017 (N-acetyl-3-decyloxyacetyl-6-chloro-2-oxyindole)

1H NMR (300 Hz) 0.87 (t, 3H, J=6.9 Hz), 1.02-1.80 (m, 16H), 2.77 (s, 3H), 3.61 (t, 2H, J=6.9 Hz), 4.56 (s, 2H), 7.10-7.44 (m, 2H), 8.02 (d, 1H, J=1.8 Hz)

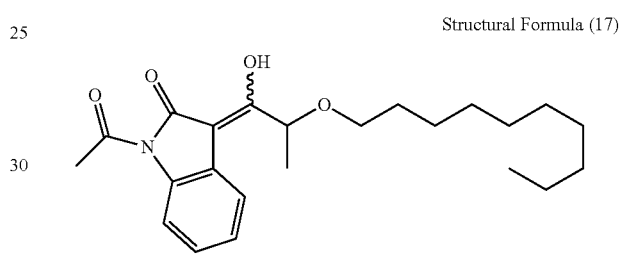

A018 (N-acetyl-3-(2-decyloxypropionyl)-2-oxyindole)

1H NMR (300 Hz) 0.87 (t, 3H, J=6.9 Hz), 1.13-1.71 (m, 16H), 1.57 (d, 3H, J=6.6 Hz), 2.77 (s, 3H), 3.37-3.67 (m, 2H), 4.60 (q, 1H, J=6.6 Hz), 7.09-7.31 (m, 2H), 7.62-7.71 (m, 1H), 8.24-8.39 (m, 1H)

13C NMR (75 Hz) 14.1, 18.1, 19.6, 16.0, 27.0, 29.2, 29.3, 29.5, 29.66, 29.73, 31.8, 70.1, 75.0, 101.1, 116.4, 121.5, 122.4, 124.8, 126.4, 135.5, 170.5, 173.0, 178.8

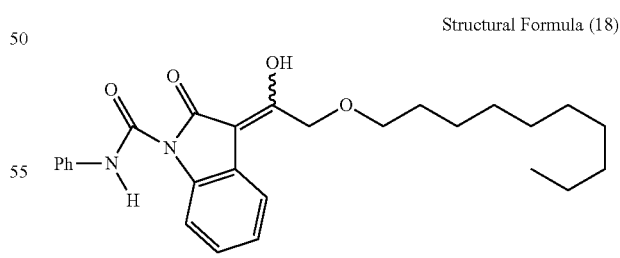

A019 (N-(phenylaminocarbonyl)-3-decyloxyacetyl-2-oxyindole)

1H NMR (300 Hz) 0.88 (t, 3H, J=6.9 Hz), 1.00-2.00 (m, 16H), 3.62 (t, 2H, J=6.6 Hz), 4.58 (s, 2H), 6.40-7.71 (m, 8H), 8.42 (d, 1H, J=7.8 Hz), 10.67 (s, 1H)

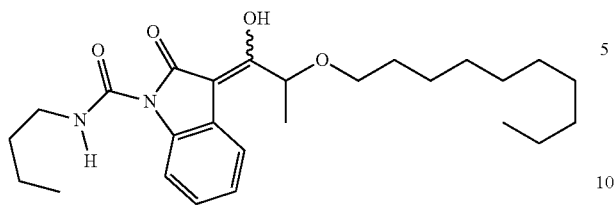

Structural Formula (19)

A020 (N-(butylaminocarbonyl)-3-(2-decyloxypropionyl)-2-oxyindole)

1H NMR (300 Hz) 0.87 (t, 3H, J=6.9 Hz), 0.91 (t, 3H, J=6.9 Hz), 1.13-1.71 (m, 20H), 1.58 (d, 3H, J=6.6 Hz), 3.37-3.67 (m, 2H), 3.64 (t, 2H, J=6.9 Hz), 4.62 (q, 1H, J=6.6 Hz), 7.10-7.70 (m, 3H), 8.25 (d, 1H, J=1.8 Hz), 10.8 (s, 1H)

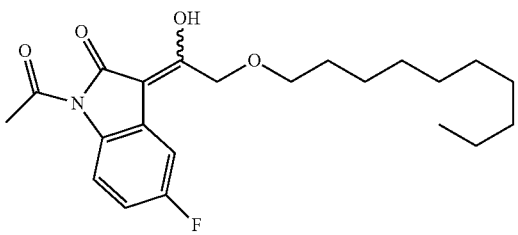

Structural Formula (22)

A023 (N-acetyl-3-decyloxyacetyl-5-fluoro-2-oxyindole)

1H NMR (300 Hz) 0.86 (t, 3H, J=6.6 Hz), 1.16-1.76 (m, 16H), 2.74 (s, 3H), 3.71 (t, 2H, J=6.9 Hz), 4.84 (s, 2H), 6.88-7.55 (m, 2H), 8.29 (d, 1H, J=7.8 Hz), 8.73 (s, 1H)

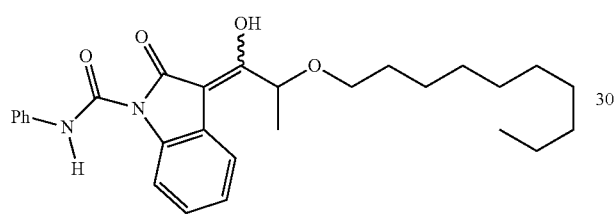

Structural Formula (20)

A021 (N-(phenylaminocarbonyl)-3-(2-decyloxypropionyl)-2-oxyindole)

1H NMR (300 Hz) 0.88 (t, 3H, Hz=6.6 Hz), 1.19-1.72 (m, 16H), 1.61 (d, 3H, J=6.6 Hz), 3.39-3.67 (m, 2H), 5.30 (q, 1H, J=6.3 Hz), 7.09-7.90 (m, 8H), 8.48 (d, 1H, J=9.0 Hz), 11.13 (s, 1H), 13.45 (s, 1H)

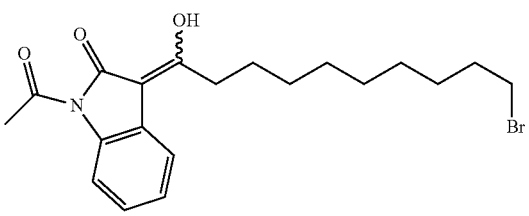

Structural Formula (23)

A024 (N-acetyl-3-(10-bromodecanoyl)-2-oxyindole)

1H NMR (300 Hz) 1.21-1.81 (m, 14H), 2.76 (s, 3H), 2.78 (t, 2H, J=7.5 Hz), 3.40 (t, 2H, J=6.6 Hz), 7.18-7.38 (m, 3H), 8.31 (d, 1H, J=0.00 Hz)

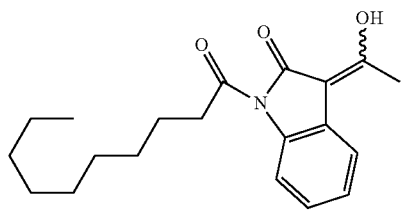

Structural Formula (21)

A022 (N-decanoyl-3-acetyl-2-oxyindole)

1H NMR (300 Hz) 0.88 (t, 3H, 6.3 Hz), 1.17-1.45 (m, 14H), 2.50 (s, 3H), 3.15 (t, 2H, J=7.2 Hz), 7.17-7.39 (m, 3H), 8.33 (dd, 1H, J=1.8, 7.5 Hz)

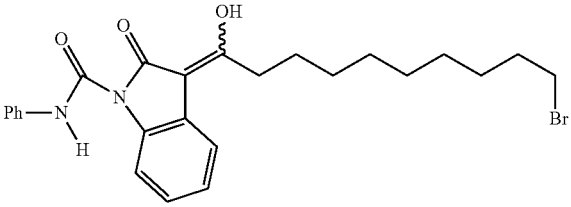

Structural Formula (24)

A025 (N-(phenylaminocarbonyl)-3-(10-bromodecanoyl)-2-oxyindole)

1H NMR (300 Hz) 1.19-1.91 (m, 14H), 2.82 (t, 2H, J=7.5 Hz), 3.40 (t, 2H, J=6.9 Hz), 7.10-7.64 (m, 6H), 7.61 (d, 2H, J=7.5 Hz), 8.44 (d, 1H, J=7.8 Hz)

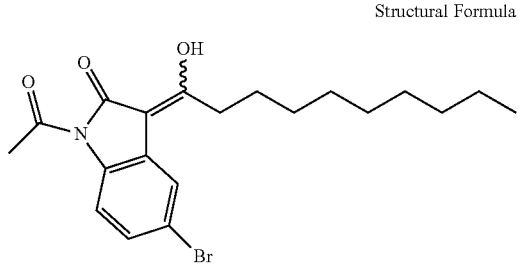

A026 (N-acetyl-5-bromo-3-decanoyl-2-oxyindole)

1H NMR (300 Hz) 0.88 (t, 3H, J=6.9 Hz), 1.23-1.85 (m, 14H), 2.74 (s, 3H), 2.78 (t, 2H, J=7.5 Hz), 7.31-7.44 (m, 2H), 8.19 (d, 1H, J=8.7 Hz)

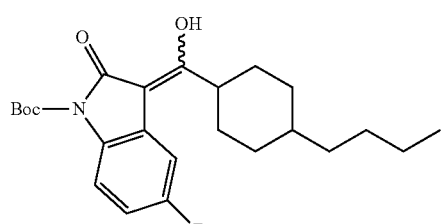

A027 (N-Boc-3-(4-butylcyclohexylcarbonyl)-5-fluoro-2-oxyindole)

1H NMR (300 Hz) 0.92 (t, 3H, J=6.9 Hz), 1.24-1.95 (m, 15H), 1.65 (s, 9H), 2.76-2.84 (m, 1H), 6.86-7.03 (m, 2H), 7.90 (d, 1H, J=9.0 Hz)

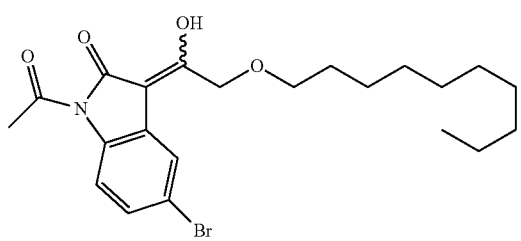

A029 (N-acetyl-5-bromo-3-decyloxyacetyl-2-oxyindole)

1H NMR (300 Hz) 0.87 (t, 3H, J=6.3 Hz), 1.16-1.22 (m, 16H), 2.73 (s, 3H), 3.71 (t, 2H, J=6.6 Hz), 4.82 (s, 2H), 7.28-7.95 (m, 2H), 8.16 (d, 1H, 8.7 Hz)

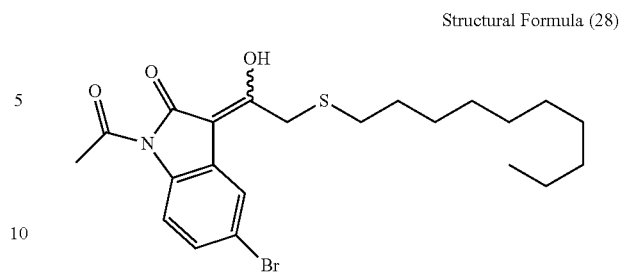

A030 (N-acetyl-5-bromo-3-decylthioacetyl-2-oxyindole)

1H NMR (300 Hz) 0.87 (t, 3H, J=6.6 Hz), 1.18-1.71 (m, 16H), 2.69-2.74 (m, 2H), 2.74 (s, 3H), 3.64 (s, 2H), 7.25-7.42 (m, 3H), 8.19 (d, 1H, 8.7 Hz)

13C NMR (75 Hz) 14.1, 22.6, 26.9, 28.7, 29.1, 29.3, 29.4, 29.5, 30.9, 31.9, 32.7, 33.1, 100.4, 118.0, 118.2, 122.9, 123.6, 129.1, 139.8, 170.3, 172.2, 176.1

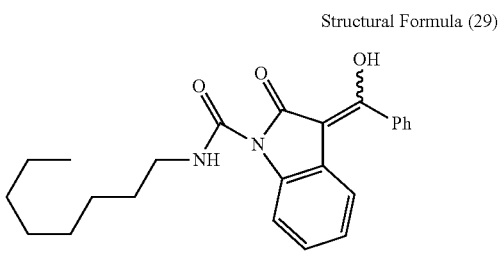 [SMILES: CCCCCCCCNC(=O)N1C(=O)C(=C(O)c2ccccc2)c2ccccc21]

A031 (N-(octylaminocarbonyl)-3-benzoyl-2-oxyindole)

1H NMR (300 Hz) 0.88 (t, 3H, J=6.6 Hz), 1.19-1.90 (m, 12H), 3.45 (q, 2H, J=5.7 Hz), 6.90-7.77 (m, 8H), 8.34 (d, 1H, J=7.8 Hz), 8.60-8.68 (br, 1H)

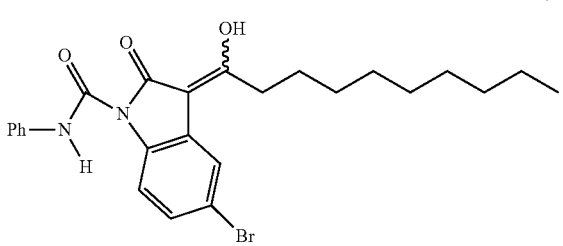

A033 (N-(phenylaminocarbonyl)-5-bromo-3-decanoyl-2-oxyindole)

1H NMR (300 Hz) 0.89 (t, 3H, J=6.6 Hz), 1.19-1.89 (m, 14H), 2.80 (t, 2H, 7.5 Hz), 7.13-7.65 (m, 5H), 7.61 (d, 2H, J=8.7 Hz), 8.34 (d, 1H, J=8.7 Hz), 10.67 (s, 1H), 13.25 (s, 1H)

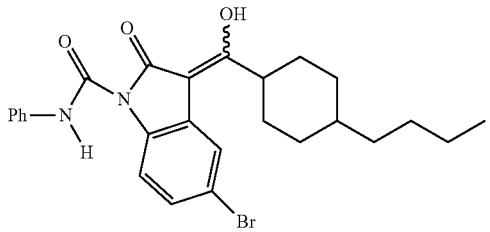

A034 (N-(phenylaminocarbonyl)-5-bromo-3-(4-butylcyclohexylcarbonyl)-2-oxyindole)

1H NMR (300 Hz) 0.92 (t, 3H, J=6.6 Hz), 1.01-2.05 (m, 15H), 2.87 (t, 1H, J=12 Hz), 7.12-7.63 (m, 5H), 7.59 (d, 2H, J=7.8 Hz), 8.32 (d, 1H, J=8.7 Hz), 10.67 (s, 1H), 13.29 (s, 1H)

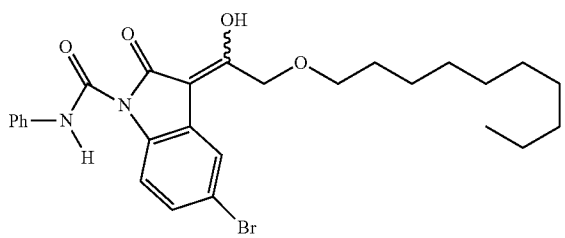

A035 (N-(phenylaminocarbonyl)-5-bromo-3-decyloxyacetyl-2-oxyindole)

1H NMR (300 Hz) 0.89 (t, 3H, J=6.6 Hz), 1.15-1.79 (m, 16H), 3.73 (t, 2H, 6.6 Hz), 4.82 (s, 2H), 7.08-7.44 (m, 5H), 7.58 (d, 2H, J=7.5 Hz), 8.24 (d, 1H, J=9.0 Hz), 8.86 (s, 1H), 10.95 (s, 1H), 12.48-13.39 (br, 1H)

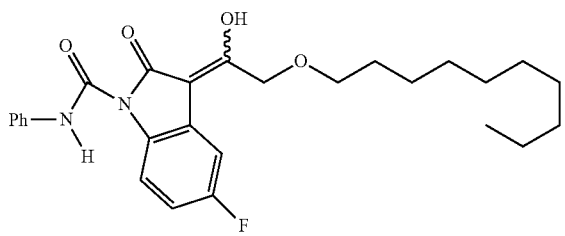

A036 (N-(phenylaminocarbonyl)-3-(4-butylcyclohexylcarbonyl)-5-fluoro-2-oxyindole)

1H NMR (300 Hz) 0.83 (t, 3H, J=6.9), 1.18-2.13 (m, 16H), 3.70 (t, 1H, J=6.6 Hz), 3.70 (t, 1H, J=6.6 Hz), 4.83 (s, 1H), 6.88-7.59 (m, 7H), 8.26 (dd, 1H, J=4.8, 9.0 Hz), 8.81 (s, 1H), 10.95 (s, 1H)

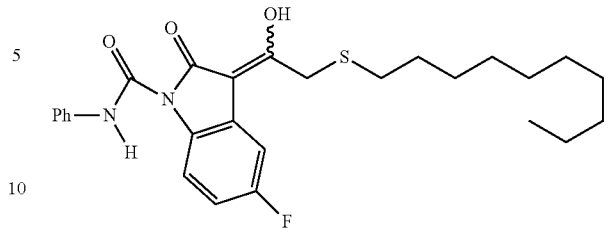

A037 (N-(phenylaminocarbonyl)-3-decylthioacetyl-5-fluoro-2-oxyindole)

1H NMR (300 Hz) 0.83 (t, 3H, J=6.6 Hz), 1.01-1.74 (m, 16H), 2.68 (t, 2H, J=7.2 Hz), 3.61 (s, 2H), 6.74-7.38 (m, 5H), 7.53 (d, 2H, J=7.5 Hz), 8.34 (dd, 1H, J=4.8, 9.0 Hz), 10.56 (s, 1H), 12.81-13.40 (br, 1H)

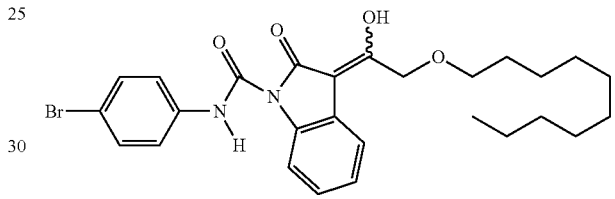

A038 (N-(4-bromophenylaminocarbonyl)-3-decyloxyacetyl-2-oxyindole)

1H NMR (300 Hz) 0.88 (t, 3H, J=6.6 Hz), 1.13-1.77 (m, 16H), 3.71 (t, 2H, J=6.6 Hz), 4.81 (s, 2H), 7.12-7.59 (m, 6H), 7.80 (d, 1H, J=7.8 Hz), 8.29 (d, 1H, J=7.8 Hz), 8.58-8.94 (br, 1H), 11.11 (s, 1H)
13C NMR (75 Hz) 14.1, 22.7, 25.7, 25.9, 29.28, 29.34, 29.4, 29.5, 31.9, 67.7, 72.1, 115.6, 116.3, 120.9, 121.7, 122.0, 124.3, 126.7, 131.9, 135.6, 136.3, 136.8, 149.9, 167.1, 174.2

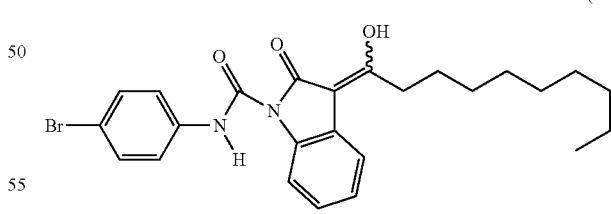

A039 (N-(4-bromophenylaminocarbonyl)-3-decanoyl-2-oxyindole)

1H NMR (300 Hz) 0.88 (t, 3H, J=6.6 Hz), 1.20-1.81 (m, 14H), 2.78 (t, 2H, J=7.5 Hz), 7.01-7.55 (m, 7H), 8.38 (d, 1H, J=8.1 Hz), 10.79 (s, 1H), 12.98-13.36 (br, 1H)
13C NMR (75 Hz) 14.1, 22.6, 25.6, 29.2, 29.3, 29.4, 30.9, 31.8, 34.3, 101.0, 116.4, 116.6, 116.9, 119.3, 121.8, 124.4, 126.0, 132.0, 135.3, 136.4, 149.2, 172.2, 180.8

Structural Formula (37)

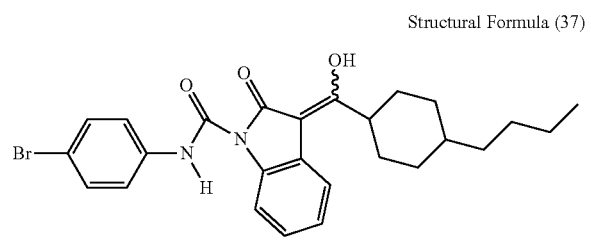 [SMILES: CCCCC1CCC(C(O)=C2C(=O)N(C(=O)Nc3ccc(Br)cc3)c3ccccc32)CC1]

A040 (N-(4-bromophenylaminocarbonyl)-3-(4-butylcyclohexylcarbonyl)-2-oxyindole)

1H NMR (300 Hz) 0.90 (t, 3H, J=6.6 Hz), 0.98-2.23 (m, 15H), 2.98 (t, 1H, J=6.7 Hz), 7.19-7.56 (m, 7H), 8.42 (d, 3H, J=7.8 Hz), 10.85 (s, 1H), 11.70 (s, 1H)

Structural Formula (38)

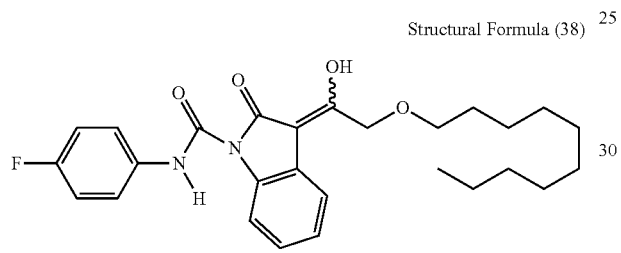

A041 (N-(4-fluorophenylaminocarbonyl)-3-decyloxyacetyl-2-oxyindole)

1H NMR (300 Hz) 0.87 (t, 3H, J=6.3 Hz), 1.08-1.79 (m, 16H), 3.73 (t, 1H, J=6.6Hz), 4.58 (s, 1H), 8.40 (d, 1H, J=7.2 Hz), 6.98 (m, 7H), 11.04 (s, 1H) 10.64 (s, 1H), 12.90-13.10 (br, 1H)

Structural Formula (39)

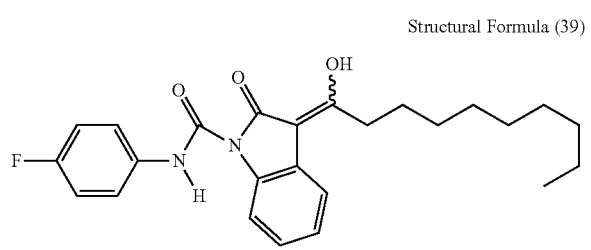 [SMILES: CCCCCCCCCC(O)=C1C(=O)N(C(=O)Nc2ccc(F)cc2)c2ccccc21]

A042 (N-(4-fluorophenylaminocarbonyl)-3-decanoyl-2-oxyindole)

1H NMR (300 Hz) 0.90 (t, 3H, J=6.6 Hz), 1.08-1.91 (m, 14H), 2.83 (t, 2H, 7.8 Hz), 6.92-7.72 (m, 7H) 8.43 (d, 1H, J=7.8 Hz), 10.77 (s, 1H), 13.21 (s, 1H)

Structural Formula (40)

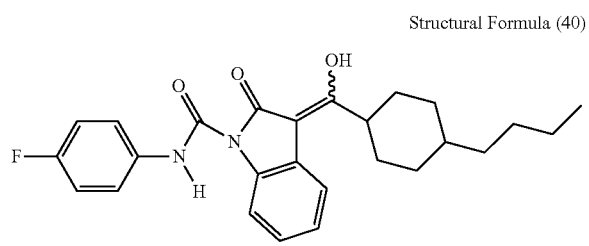 [SMILES: CCCCC1CCC(C(O)=C2C(=O)N(C(=O)Nc3ccc(F)cc3)c3ccccc32)CC1]

A043 (N-(4-fluorophenylaminocarbonyl)-3-(4-butylcyclohexylcarbonyl)-2-oxyindole)

1H NMR (300 Hz) 0.92 (t, 3H, J=6.6 Hz), 1.20-2.07 (m, 15H), 2.96-3.04 (m, 1H), 7.04-7.62 (m, 7H), 8.44 (d, 1H, J=7.5 Hz), 10.78 (s, 1H), 13.18 (s, 1H)

Structural Formula (41)

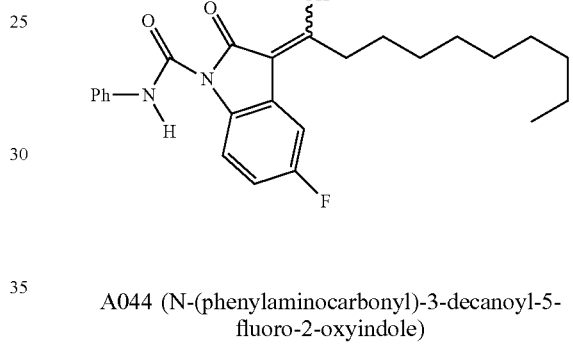

A044 (N-(phenylaminocarbonyl)-3-decanoyl-5-fluoro-2-oxyindole)

1H NMR (300 Hz) 0.89 (t, 3H, J=6.6 Hz), 1.17-1.87 (m, 14H), 2.77 (t, 2H, J=7.5 Hz), 6.85-7.44 (m, 5H), 7.59 (d, 2H, J=7.5 Hz), 8.40 (dd, 1H, J=4.8, 9.0 Hz), 10.68 (s, 1H), 13.19-13.23 (br, 1H)

13C NMR (75 Hz) 14.1, 22.6, 25.5, 29.1, 29.2, 29.3, 29.4, 31.8, 34.2, 100.8, 106.5 (d), 112.3 (d), 117.4 (d), 120.3, 122.9 (d), 124.4, 129.0, 131.3, 137.1, 149.0, 158.3, 160.5 (d), 172.0, 181.7

Structural Formula (42)

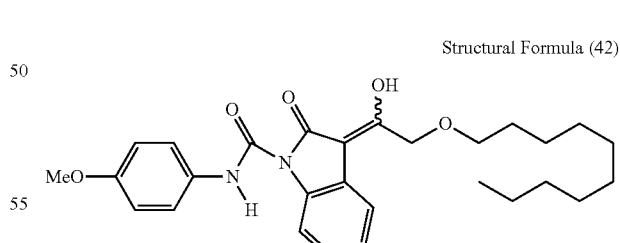

A045 (N-(4-methoxyphenylaminocarbonyl)-3-decyloxyacetyl-2-oxyindole)

1H NMR (300 Hz) 0.87 (t, 3H, J=6.9 Hz), 1.14-1.77 (m, 16H), 3.61 (t, 2H, J=6.6 Hz), 3.81 (s, 3H), 4.56 (s, 2H), 6.83-7.57 (m, 7H), 8.40 (d, 1H, J=7.8 Hz), 8.62-8.93 (br, 1H), 10.49 (s, 1H)

2H, J (doublet)=6.6 Hz), 8.40 (dd, 1H, J=4.8, 9.0 Hz), 10.51 (s, 1H), 13.10-13.22 (br, 1H)

Structural Formula (43)

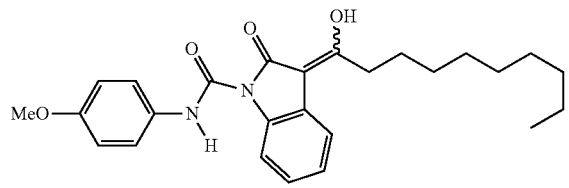

A046 (N-(4-methoxyphenylaminocarbonyl)-3-decanoyl-2-oxyindole)

1H NMR (300 Hz) 0.89 (t, 3H, J=6.9 Hz), 1.18-1.87 (m, 14H), 2.79 (t, 2H, J=7.8 Hz), 3.81 (s, 3H), 6.90 (dt, 2H, J (doublet)=6.9 Hz), 7.16-7.39 (m, 3H), 7.51 (dt, 2H, J (doublet)=6.9 Hz), 8.42 (d, 1H, J=7.5 Hz), 10.59 (s, 1H), 13.04-13.21 (br, 1H)

13C NMR (75 Hz) 14.1, 22.6, 25.7, 29.2, 29.28, 29.37, 29.43, 31.8, 34.3, 55.4, 101.1, 114.2, 116.4, 119.2, 121.6, 122.2, 124.2, 126.0, 130.2, 135.6, 149.6, 156.5, 172.2, 180.5

Structural Formula (46)

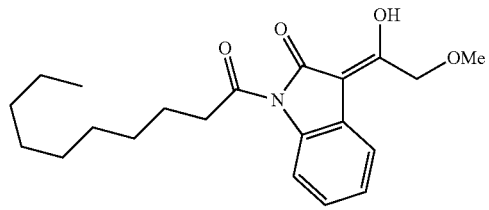

A049 (N-decanoyl-3-methoxyacetyl-2-oxyindole)

1H NMR (300 Hz) 0.87 (t, 3H, J=6.9 Hz), 0.97-1.83 (m, 14H), 3.14 (t, 2H, J=6.9 Hz), 3.52 (s, 3H), 4.51 (s, 2H), 7.14-7.44 (m, 3H), 8.30 (d, 1H, J=7.8 Hz)

Structural Formula (44)

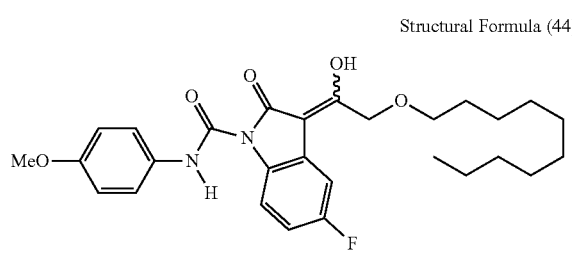

A047 (N-(4-methoxyphenylaminocarbonyl)-3-decyloxyacetyl-5-fluoro-2-oxyindole)

1H NMR (300 Hz) 0.88 (t, 3H, J=6.6 Hz), 0.98-1.78 (m, 16H), 3.60 (t, 2H, J=6.6 Hz), 3.80 (s, 3H), 4.82 (s, 2H), 6.76-7.56 (m, 6H), 8.26 (dd, 1H, J=4.8, 9.0 Hz), 8.74-9.01 (br, 1H), 10.79 (s, 1H)

Structural Formula (47)

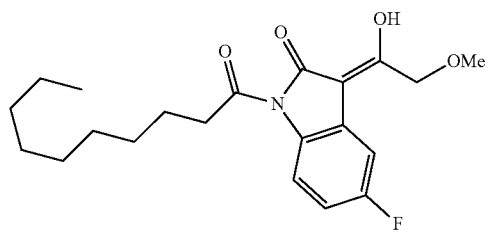

A050 (N-decanoyl-3-methoxyacetyl-5-fluoro-2-oxyindole)

1H NMR (300 Hz) 0.87 (t, 3H, J=6.6 Hz), 1.14-1.85 (m, 14H), 3.13 (t, 2H, J=7.5 Hz), 3.51 (s, 3H), 4.47 (s, 2H), 6.86-7.31 (m, 2H), 8.30 (d, 1H, J=7.8 Hz)

Structural Formula (45)

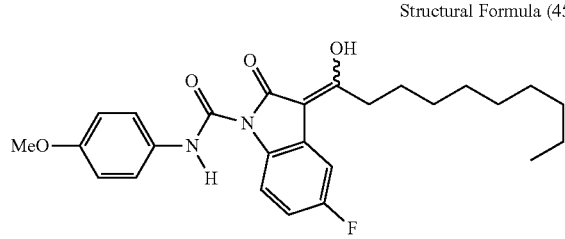

A048 (N-(4-methoxyphenylaminocarbonyl)-3-decanoyl-5-fluoro-2-oxyindole)

1H NMR (300 Hz) 0.88 (t, 3H, J=6.6 Hz), 1.18-1.87 (m, 14H), 2.78 (t, 2H, J=7.5 Hz), 6.88-7.10 (m, 5H), 7.50 (dt,

Structural Formula (48)

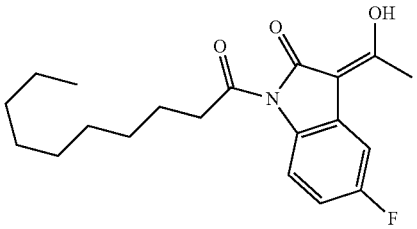

A051 (N-decanoyl-3-acetyl-5-fluoro-2-oxyindole)

1H NMR (300 Hz) 0.88 (t, 3H, J=6.6 Hz), 1.06-1.81 (m, 16H), 2.47 (s, 3H), 3.13 (t, 2H, J=7.2 Hz), 6.85-7.07 (m, 2H), 8.29 (dd, 1H, J=4.8, 9.2 Hz)

Structural Formula (49)

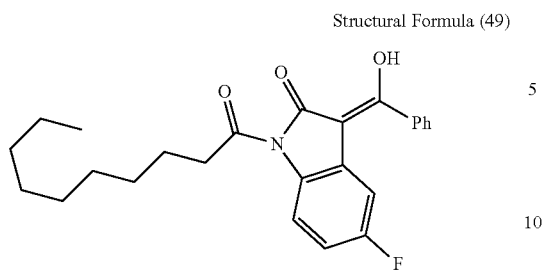

A052 (N-decanoyl-3-benzoyl-5-fluoro-2-oxyindole)

1H NMR (300 Hz) 0.88 (t, 3H, J=6.9 Hz), 1.04 (m, 14H), 3.18 (t, 2H, J=7.5 Hz), 6.74 (dd, 1H, J=2.7, 9.3 Hz), 6.88 (dt, 1H, J=2.7, 9.0 Hz), 7.44-7.77 (m, 5H), 8.28 (dd, 1H, J=4.8, 9.0 Hz)

Structural Formula (50)

A053 (N-(4-(trifluoromethoxy)phenylaminocarbonyl)-3-decanoyl-2-oxyindole)

1H NMR (300 Hz) 0.87 (t, 3H, J=6.6 Hz), 1.18-1.89 (m, 14H), 2.83 (t, 2H, J=7.5 Hz), 7.10-7.69 (m, 5H), 7.64 (dt, 2H, J (doublet)=8.8 Hz), 8.43 (d, 1H, J=8.4 Hz), 10.9 (s, 1H), 13.2 (s, 1H)

Structural Formula (51)

A054 (N-(2-(trifluoromethyl)phenylaminocarbonyl)-3-decanoyl-2-oxyindole)

1H NMR (300 Hz) 0.87 (t, 3H, J=6.6 Hz), 1.18-1.90 (m, 14H), 2.84 (t, 2H, J=7.5 Hz), 7.20-7.40 (m, 4H), 7.62 (t, 1H, J=7.8 Hz), 7.64 (d, 1H, J=7.8 Hz), 8.22 (d, 1H, J=8.4 Hz), 8.34 (d, 1H, J=8.4 Hz) 11.5 (s, 1H)

Structural Formula (52)

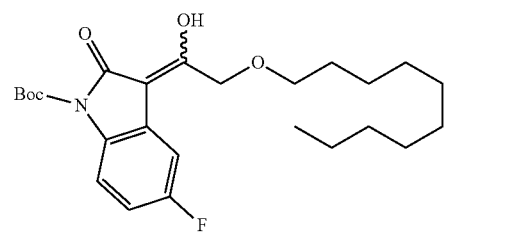

A055 (N-Boc-3-decyloxyacetyl-5-fluoro-2-oxyindole)

1H NMR (300 Hz) 0.86 (t, 3H, J=6.9 Hz), 1.18-1.40 (m, 14H), 1.64 (s, 3H), 1.65-1.75 (m, 2H), 3.56 (t, 2H, J=6.0 Hz), 4.48 (s, 2H), 6.92 (dt, 1H, J=2.5, 8.8 Hz), 7.21 (dd, 1H, J=2.5, 8.8 Hz), 7.86 (dd, 1H, J=4.8, 8.8 Hz)

Structural formula (53)

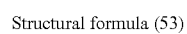

A056 (N-Boc-6-chloro-3-decyloxyacetyl-2-oxyindole)

1H NMR (300 Hz) 0.86 (t, 3H, J=6.9 Hz), 1.18-1.42 (m, 14H), 1.66 (s, 3H), 1.52-1.76 (m, 2H), 3.55 (t, 2H, J=6.0 Hz), 4.48 (s, 2H), 7.10-7.20 (m, 1H), 7.39 (d, 1H, J=8.4 Hz), 7.98 (d, 1H, J=2.1 Hz)

Structural Formula (54)

A057 (N-acetyl-3-octyloxyacetyl-2-oxyindole)

1H NMR (300 Hz) 0.87 (t, 3H, J=6.9 Hz), 1.13-1.87 (m, 12H), 2.76 (s, 3H), 3.60 (t, 2H, J=6.9 Hz), 4.54 (s, 2H), 7.17-7.32 (m, 2H), 7.43 (dd, 1H, J=2.1, 7.8 Hz), 8.30 (d, 1H, J=7.8 Hz)

Structural Formula (55)

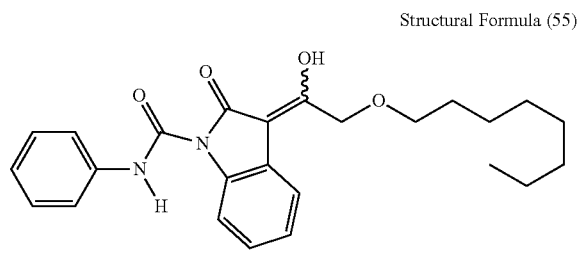 [SMILES: CCCCCCCCOCC(O)=C1C(=O)N(C(=O)Nc2ccccc2)c2ccccc21]

A058 (N-(phenylaminocarbonyl)-3-octyloxyacetyl-2-oxyindole)

1H NMR (300 Hz) 0.87 (t, 3H, J=6.9 Hz), 1.13-1.87 (m, 12H), 3.60 (t, 2H, J=6.9 Hz), 4.58 (s, 2H), 6.98-7.45 (m, 6H), 7.61 (dt, 2H, J (doublet=8.7 Hz), 8.44 (d, 1H, J=7.8 Hz), 10.67 (s, 1H)

Structural Formula (56)

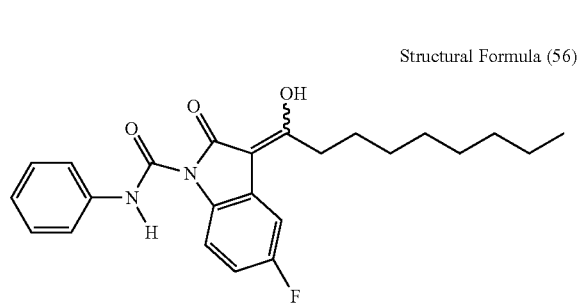 [SMILES: CCCCCCCCC(O)=C1C(=O)N(C(=O)Nc2ccccc2)c2ccc(F)cc21]

A059 (N-(phenylaminocarbonyl)-5-fluoro-3-nonanoyl-2-oxyindole)

1H NMR (300 Hz) 0.90 (t, 3H, J=6.6 Hz), 1.21-1.85 (m, 12H), 2.72 (t, 2H, J=6.9 Hz), 6.86-7.20 (m, 3H), 7.35 (t, 2H, J=8.8 Hz), 7.58 (d, 2H, J=8.8 Hz), 8.38 (dd, 1H, J=4.8, 8.8 Hz), 10.62 (s, 1H)

Structural Formula (57)

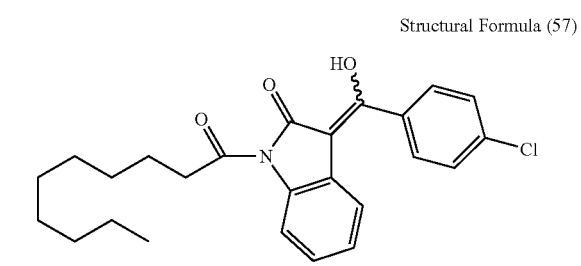 [SMILES: CCCCCCCCCC(=O)N1C(=O)C(=C(O)c2ccc(Cl)cc2)c2ccccc21]

A060 (N-decanoyl-3-(4-chlorobenzoyl)-2-oxyindole)

1H NMR (300 Hz) 0.89 (t, 3H, J=6.3 Hz), 1.10-1.56 (m, 12H), 1.74-1.86 (m, 2H), 3.20 (t, 2H), 3.20 (t, 2H, J=7.6 Hz), 6.98-7.30 (m, 4H), 7.55 (dt, 2H, J (doublet=8.7 Hz), 7.72 (dt, 2H, J (doublet=8.7 Hz), 8.31 (d, 1H, J=8.1 Hz), 13.80 (brs, 1H)

Structural Formula (58)

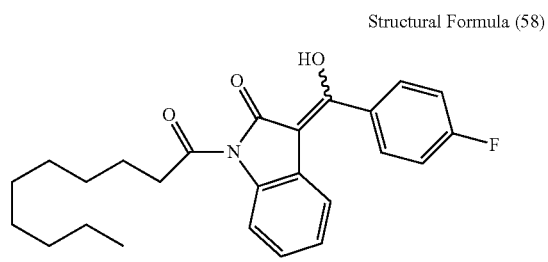 [SMILES: CCCCCCCCCC(=O)N1C(=O)C(=C(O)c2ccc(F)cc2)c2ccccc21]

A061 (N-decanoyl-3-(4-fluorobenzoyl)-2-oxyindole)

1H NMR (300 Hz) 0.89 (t, 3H, J=6.3 Hz), 1.10-1.56 (m, 12H), 1.74-1.88 (m, 2H), 3.20 (t, 2H, J=7.6 Hz), 3.92 (s, 3H), 6.98-7.30 (m, 4H), 7.23 (dd, 2H, J=7.8, 8.4 Hz), 7.78 (dd, 2H, J=7.8, 8.4 Hz), 8.34 (d, 1H, J=8.1 Hz), 13.85 (brs, 1H)

Structural Formula (59)

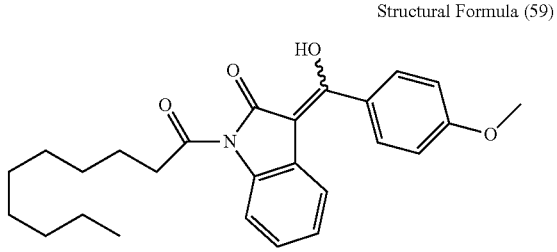 [SMILES: CCCCCCCCCC(=O)N1C(=O)C(=C(O)c2ccc(OC)cc2)c2ccccc21]

A062 (N-decanoyl-3-(4-methoxybenzoyl)-2-oxyindole)

1HNMR (300 Hz) 0.88 (t, 3H, J=6.3 Hz), 1.10-1.56 (m, 12H), 1.74-1.86 (m, 2H), 3.21 (t, 2H, J=7.6 Hz), 6.98-7.30 (m, 4H), 7.05 (dt, 2H, J (doublet=8.7 Hz), 7.78 (dt, 2H, J (doublet=8.7 Hz), 8.30 (d, 1H, J=8.1 Hz), 13.78 (brs, 1H)

Structural Formula (60)

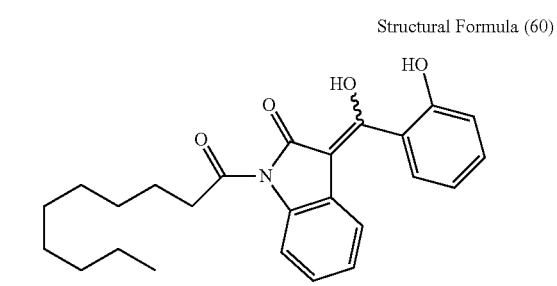 [SMILES: CCCCCCCCCC(=O)N1C(=O)C(=C(O)c2ccccc2O)c2ccccc21]

A063 (N-decanoyl-3-(2-hydroxybenzoyl)-2-oxyindole)

1H NMR (300 Hz) 0.88 (t, 3H, J=6.3 Hz), 1.10-1.56 (m, 12H), 1.74-1.86 (m, 2H), 3.16 (t, 2H, J=7.6 Hz), 7.02-8.40 (m, 8H)

<Compound B>

The compound B is a 3-acyl-4-hydroxycoumarin compound represented by the General Formula (3).

Examples of the compound B include 3-acyl-4-hydroxycoumarin compounds expressed by Structural Formulas (61) to (75) below.

Structural Formula (61)

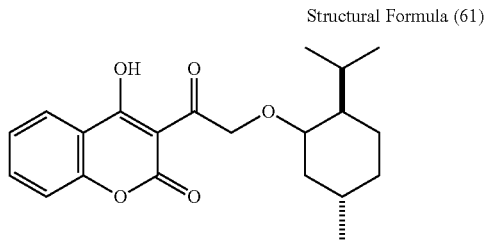 [SMILES: CC(C)[C@H]1CC[C@H](C)CC1OCC(=O)c1c(O)c2ccccc2oc1=O]

B006 (4-hydroxy-3-menthyloxyacetylcoumarin)

1H NMR (300 Hz) 0.81 (d, 3H, J=6.9 Hz), 0.91 (d, 6H, J=6.9 Hz), 0.75-2.40 (m, 9H), 3.20-3.30 (m, 1H), 4.87 and 5.00 (ABq, 2H, J=20.4 Hz), 7.29-7.40 (m, 2H), 7.71 (dt, 1H, J=1.5, 8.4 Hz), 8.08 (dd, 1H, J=1.5, 7.8 Hz)

Structural Formula (62)

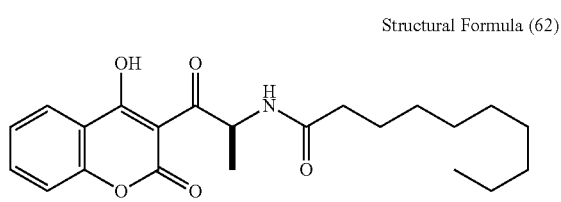 [SMILES: CCCCCCCCCC(=O)N[C@@H](C)C(=O)c1c(O)c2ccccc2oc1=O]

B011
(3-(2-decanoylaminopropionyl)-4-hydroxycoumarin)

1H NMR (300 Hz) 0.87 (t, 3H, J=6.6 Hz), 1.11-1.69 (m, 14H), 1.49 (d, 3H, J=7.2 Hz), 2.24 (t, 2H, J=7.5 Hz), 5.78-5.94 (m, 1H), 6.20 (d, 1H, J=7.5 Hz), 7.24-7.39 (m, 2H), 7.72 (dt, 2H, J=1.5, 8.4 Hz), 8.06 (dd, 1H, J=1.5, 7.8 Hz)

Structural Formula (63)

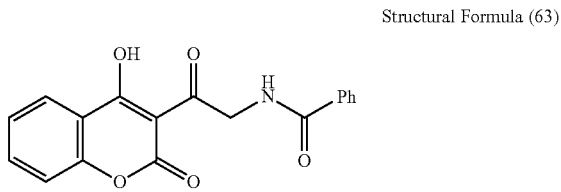 [SMILES: O=C(NCC(=O)c1c(O)c2ccccc2oc1=O)c1ccccc1]

B013 (3-benzoylaminoacetyl-4-hydroxycoumarin)

1H NMR (300 Hz) 4.49 (s, 2H), 7.36-7.84 (m, 9H), 7.93-8.04 (br, 1H), 12.57 (s, 1H)

Structural Formula (64)

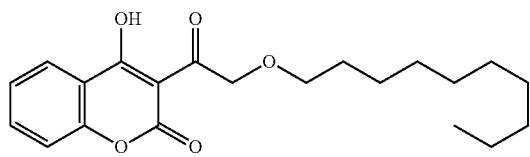

B015 (3-decyloxyacetyl-4-hydroxycoumarin)

1H NMR (300 Hz) 0.87 (t, 3H, J=6.9 Hz), 1.18-1.75 (m, 16H), 3.61 (t, 2H, J=6.6 Hz), 4.89 (s, 2H), 7.23-7.40 (m, 2H), 7.72 (dt, 1H, J=1.5, 8.4 Hz), 8.07 (dd, 1H, J=1.5, 7.8 Hz)

Structural Formula (65)

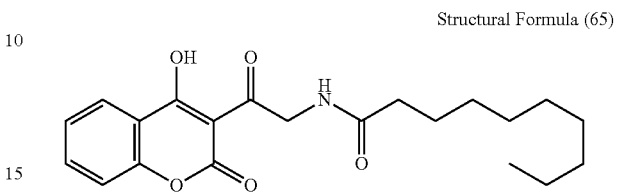

B016 (3-decanoylaminoacetyl-4-hydroxycoumarin)

1H NMR (300 Hz) 0.87 (t, 3H, J=6.9 Hz), 0.91-1.76 (m, 14H), 2.36 (t, 2H, J=6.6 Hz), 4.87 (d, 2H, 6.0 Hz), 6.30-6.42 (br, 1H), 7.26-7.44 (m, 2H), 7.72 (dt, 1H, J=1.5, 8.4 Hz), 8.07 (dd, 1H, J=1.5, 7.8 Hz)

Structural Formula (66)

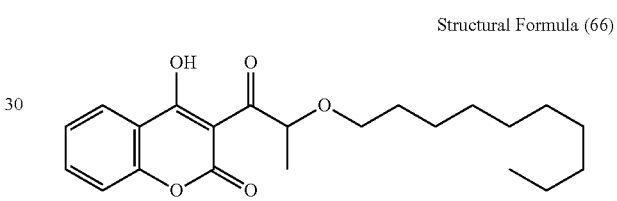

B017 (3-(2-decyloxypropionyl)-4-hydroxycoumarin)

1H NMR (300 Hz) 0.87 (t, 3H, J=6.9 Hz), 1.18-1.42 (m, 14H), 1.46 (d, 3H, J=6.6 Hz), 1.57-1.70 (m, 2H), 3.33-3.57 (m, 2H), 5.29 (q, 1H, J=6.6 Hz), 7.22-7.35 (m, 2H), 7.66 (dt, 1H, J=1.5, 8.4 Hz), 8.03 (dd, 1H, J=1.2, 7.8 Hz)
13C NMR (75 Hz) 14.1, 18.4, 22.7, 26.0, 29.3, 29.4, 29.5, 29.7, 29.9, 31.9, 70.5, 78.0, 100.1, 115.0, 117.0, 124.6, 125.6, 136.4, 154.8, 159.4, 178.9, 208.8

Structural Formula (67)

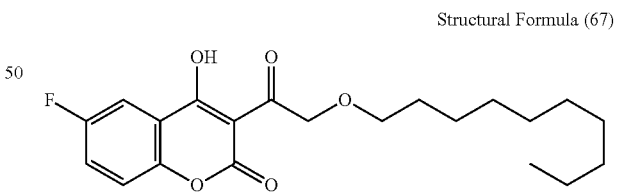

B019
(3-decyloxyacetyl-6-fluoro-4-hydroxycoumarin)

1H NMR (300 Hz) 0.91 (t, 3H, J=6.9 Hz), 1.18-1.78 (m, 16H), 3.64 (t, 2H, J=6.9 Hz), 4.92 (s, 2H), 7.22-7.35 (m, 1H), 7.39 (dt, 1H, J=3.0, 9.0 Hz), 7.70 (dd, 1H, J=3.0, 7.8 Hz)
13C NMR (75 Hz) 14.1, 22.7, 26.0, 29.3, 29.4, 29.5, 29.6, 29.7, 31.9, 72.1, 75.4, 100.1, 110.9, 119.0, 124.0, 150.9, 157.2, 159.3, 160.4, 176.9, 204.6

Structural Formula (68)

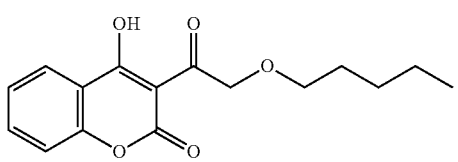

B021 (4-hydroxy-3-(pentyloxyacetyl)coumarin)

1H NMR (300 Hz) 0.90 (t, 3H, J=6.9 Hz), 1.29-1.82 (m, 6H), 3.60 (t, 2H, J=6.9 Hz), 4.87 (s, 2H), 7.22-7.35 (m, 2H), 7.66 (dt, 1H, J=1.3, 10.5 Hz), 8.03 (dd, 1H, J=1.3, 7.8 Hz)

Structural Formula (69)

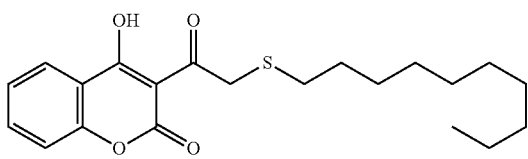

B023 (3-decylthioacetyl-4-hydroxycoumarin)

1H NMR (300 Hz) 0.86 (t, 3H, J=6.6 Hz), 1.17-1.68 (m, 16H), 2.57 (t, 2H, J=7.5 Hz), 4.00 (s, 2H), 7.25-7.38 (m, 2H), 7.69 (dt, 1H, J=1.5, 8.4 Hz), 8.04 (dd, 1H, J=1.5, 7.5 Hz)
13C NMR (75 Hz) 14.1, 22.6, 28.7, 29.0, 29.1, 29.2, 29.42, 29.47, 31.8, 32.0, 40.0, 99.8, 114.9, 117.0, 124.5, 125.4, 136.1, 154.6, 159.5, 178.6, 201.9

Structural Formula (70)

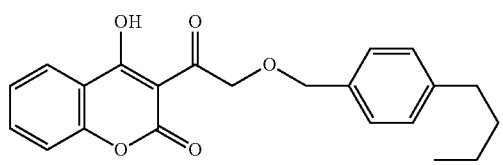

B024 (3-(4-butylphenylmethoxyl)acetyl-4-hydroxycoumarin)

1H NMR (300 Hz) 0.92 (t, 3H, J=6.6 Hz), 1.24-1.64 (m, 4H), 2.60 (t, 2H, J=7.5 Hz), 4.68 (s, 2H), 4.92 (s, 2H), 7.17 (d, 2H, J=7.8 Hz), 7.30-7.40 (m, 4H), 7.72 (dt, 1H, J=1.5, 8.4 Hz), 8.08 (dd, 1H, J=1.5, 7.8 Hz)
13C NMR (75 Hz) 13.9, 22.3, 33.6, 35.4, 73.4, 74.3, 100.0, 114.7, 117.1, 124.7, 125.5, 128.1, 128.6, 134.4, 136.3, 142.8, 154.7, 159.6, 177.7, 204.2

Structural Formula (71)

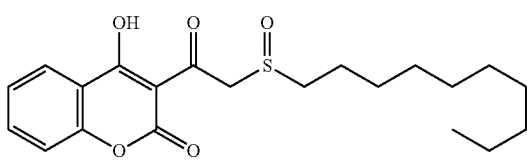

B026 (3-(decylsulfonyl)acetyl-4-hydroxycoumarin)

1H NMR (300 Hz) 0.88 (t, 3H, J=6.6 Hz), 1.17-1.91 (m, 16H), 2.94 (dt, 2H, J=2.7, 7.5 Hz), 4.30 and 4.74 (ABq, 2H, J=13.2 Hz), 7.31-7.42 (m, 2H), 7.75 (dt, 1H, J=1.5, 8.4 Hz), 8.09 (dd, 1H, J=1.5, 7.8 Hz)

Structural Formula (72)

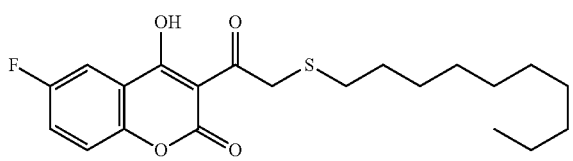

B027 (3-decylthioacetyl-6-fluoro-4-hydroxycoumarin)

1H NMR (300 Hz) 0.87 (t, 3H, J=6.6 Hz), 1.12-1.67 (m, 16H), 2.57 (t, 2H, J=7.5 Hz), 3.99 (s, 2H), 7.23-7.34 (m, 1H), 7.41 (dt, 1H, J=3.0, 9.0 Hz), 7.70 (dd, 1H, J=3.0, 7.8 Hz)

Structural Formula (73)

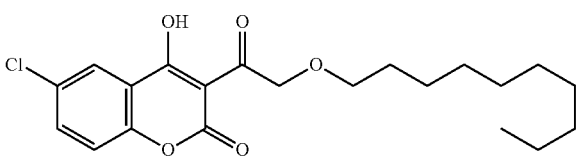

B028 (3-decyloxyacetyl-6-chloro-4-hydroxycoumarin)

1H NMR (300 Hz) 0.87 (t, 3H, J=6.9 Hz), 1.20-1.50 (m, 14H), 1.62-1.78 (m, 2H), 3.60 (t, 2H, J=6.0 Hz), 4.87 (s, 2H), 7.28 (d, 1H, J=8.8 Hz), 7.63 (dd, 1H, J=2.4, 8.8 Hz), 8.02 (d, 1H, J=2.4 Hz)
13C NMR (75 Hz) 14.1, 22.7, 26.0, 29.3, 29.4, 29.50, 29.54, 29.6, 31.9, 72.2, 75.4, 100.2, 110.3, 118.7, 124.8, 130.4, 136.3, 153.1, 160.8, 178.2, 204.6

Structural Formula (74)

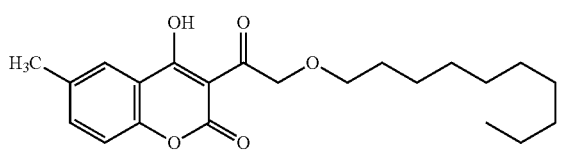

B029 (3-decyloxyacetyl-6-methyl-4-hydroxycoumarin)

1H NMR (300 Hz) 0.87 (t, 3H, J=6.9 Hz), 1.18-1.48 (m, 14H), 1.60-1.78 (m, 2H), 2.44 (s, 3H), 3.60 (t, 2H, J=6.0 Hz), 4.88 (s, 2H), 7.22 (d, 1H, J=8.8 Hz), 7.52 (dd, 1H, J=2.4, 8.8 Hz), 7.84 (d, 1H, J=2.4 Hz)
13C NMR (75 Hz) 14.1, 20.8, 22.6, 26.0, 29.3, 29.4, 29.51, 29.54, 29.6, 31.8, 72.0, 75.4, 99.8, 114.3, 116.8, 124.9, 134.6, 137.5, 152.9, 159.8, 177.8, 204.4

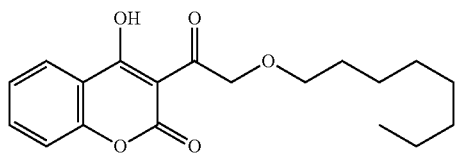

B030 (3-octyloxyacetyl-4-hydroxycoumarin)

1H NMR (300 Hz) 0.87 (t, 3H, J=6.9 Hz), 1.13-1.87 (m, 12H), 3.60 (t, 2H, J=6.9 Hz), 4.88 (s, 2H), 7.22-7.35 (m, 2H), 7.66 (dt, 1H, J=1.5, 8.4 Hz), 8.03 (dd, 1H, J=1.2, 7.8 Hz)

<Compounds BI and BII>

The antibacterial compounds BI and BII are 3-acyl-4-hydroxycoumarin compounds and are represented by the General Formulas (4) and (5), respectively.

Examples of the antibacterial compounds BI and BII include 3-acyl-4-hydroxycoumarin compounds expressed by Structural Formulas (76) to (83) below.

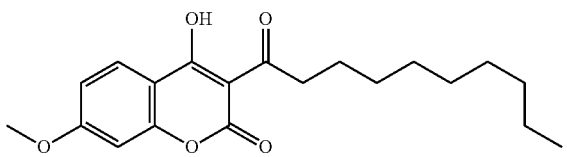

B001 (3-decanoyl-4-hydroxy-7-methoxycoumarin)

1H NMR (300 Hz) 0.87 (t, 3H, J=6.9 Hz), 0.98-1.82 (m, 14H), 3.15 (t, 2H, J=7.5 Hz), 3.90 (s, 3H), 6.73 (d, 1H, J=2.4 Hz), 6.88 (dd, 1H, J=2.4, 8.7 Hz), 7.94 (d, 1H, J=8.7 Hz)

13C NMR (75 Hz) 14.1, 22.6, 24.2, 24.8, 25.2, 29.3, 29.4, 31.9, 41.5, 56.0, 99.4, 100.1, 108.4, 113.3, 127.0, 156.9, 160.2, 166.2, 178.6, 208.4

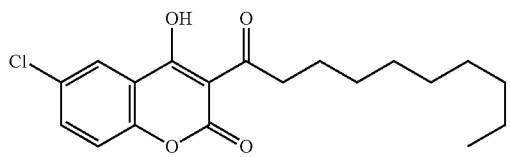

B003 (6-chloro-3-decanoyl-4-hydroxycoumarin)

1H NMR (300 Hz) 0.87 (t, 3H, J=6.6 Hz), 1.21-1.77 (m, 14H), 3.19 (t, 2H, J=7.5 Hz), 7.23-7.27 (m, 1H), 7.62 (dd, 1H, J=2.4, 9.0 Hz), 8.02 (d, 1H, J=2.4 Hz)

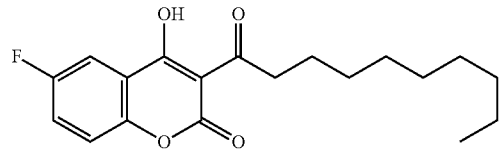

B004 (3-decanoyl-6-fluoro-4-hydroxycoumarin)

1H NMR (300 Hz) 0.87 (t, 3H, J=6.6 Hz), 1.17-2.78 (m, 14H), 3.19 (t, 2H, J=7.5 Hz), 7.25-7.35 (m, 1H), 7.40 (dt, 1H, J=3.0, 9.0 Hz), 7.70 (dd, 1H, J=3.0, 7.8 Hz)

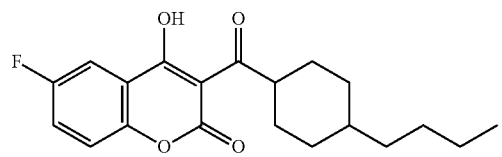

B009 (3-(4-butylcyclohexylcarbonyl)-6-fluoro-4-hydroxycoumarin)

1H NMR (300 Hz) 0.89 (t, 3H, J=6.9 Hz), 1.00-2.05 (m, 15H), 3.77 (tt, 1H, J=2.7, 7.2 Hz), 7.22-7.35 (m, 1H), 7.39 (dt, 1H, J=3.0, 9.0 Hz), 7.70 (dd, 1H, J=3.0, 7.8 Hz)

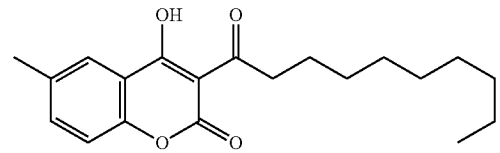

B012 (3-decanoyl-6-methyl-4-hydroxycoumarin)

1H NMR (300 Hz) 0.86 (t, 3H, J=6.9 Hz), 1.18-1.86 (m, 14H), 2.41 (s, 3H), 3.17 (t, 2H, J=7.2 Hz), 7.17 (d, 1H, J=9.0 Hz), 7.45 (d, 1H, 9.0 Hz), 7.80 (s, 1H)

13C NMR (75 Hz) 14.1, 20.8, 22.6, 24.1, 29.21, 29.24, 29.4, 29.5, 31.8, 41.7, 100.9, 114.9, 116.7, 124.9, 134.2, 137.1, 152.8, 160.1, 178.7, 208.8

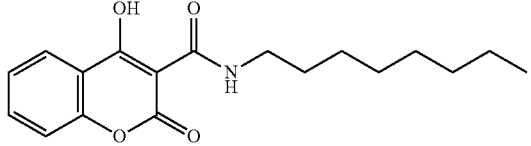

B020 (3-(octylaminocarbonyl)-4-hydroxycoumarin)

1H NMR (300 Hz) 0.86 (t, 3H, J=6.9 Hz), 1.17-1.77 (m, 12H), 3.37-3.47 (m, 2H), 7.22-7.35 (m, 2H), 7.66 (dt, 1H, J=1.5, 8.4 Hz), 8.03 (dd, 1H, J=1.5, 7.8 Hz), 9.11-9.32 (br, 1H)
13C NMR (75 Hz) 14.0, 22.6, 26.9, 29.1, 29.2, 30.9, 31.7, 39.5, 91.3, 116.2, 116.9, 124.5, 125.0, 134.7, 153.4, 162.7, 170.5, 177.1

Structural Formula (82)

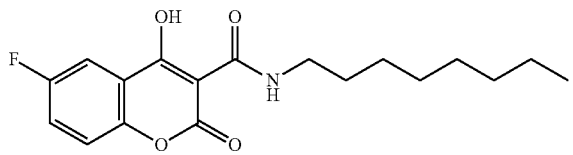

B022 (6-fluoro-3-(octylaminocarbonyl)-4-hydroxycoumarin)

1H NMR (300 Hz) 0.89 (t, 3H, J=6.9 Hz), 1.17-1.67 (m, 12H), 2.85-2.97 (m, 2H), 5.45-5.53 (br, 1H), 7.22-7.35 (m, 1H), 7.39 (dt, 1H, J=3.0, 9.0 Hz), 7.70 (dd, 1H, J=3.0, 7.8 Hz)

Structural Formula (83)

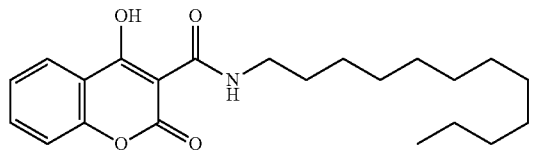

B025 (3-(dodecylaminocarbonyl)-4-hydroxycoumarin)

1H NMR (300 Hz) 0.87 (t, 3H, J=6.6 Hz), 1.18-1.69 (m, 20H), 3.38-3.47 (m, 2H) 7.26-7.38 (m, 2H), 7.65 (dt, 1H, J=1.5, 8.4 Hz), 8.03 (dd, 1H, J=1.5, 7.5 Hz), 9.18-9.29 (br, 1H)
13C NMR (75 Hz) 14.1, 22.6, 26.9, 29.13, 29.18, 29.31, 29.35, 29.46, 29.52, 29.57, 31.9, 39.5, 91.3, 116.2, 116.9, 124.5, 125.0, 134.7, 153.4, 162.7, 170.5, 177.1

(Method for Producing the Compound, the Tautomer or Geometric Isomer Thereof, or the Salt Thereof; and Method for Producing the Antibacterial Compound or the Salt Thereof)

A method for producing the compound, the tautomer or geometric isomer thereof, or the salt thereof of the present invention, and a method for producing the antibacterial compound or the salt thereof of the present invention are any one of synthesis methods 1 to 5 below.

<Compound and Antibacterial Compound>

The compound and the antibacterial compound are compounds belonging to the 3-acyloxyindole compounds and the 3-acyl-4-hydroxycoumarin compounds represented by the General Formulas (1) to (5) (compounds AI, AII, B, BI, and BII).

<Tautomer and Geometric Isomer Thereof>

The tautomer and geometric isomer thereof include tautomers and geometric isomers of the compound AI and AII since the compound AI represented by the General Formula (1) and the compound AII represented by the General Formula (2) have tautomers and geometric isomers thereof. The compounds A and C can have several kinds of structural patterns represented by the above Chemical Formula (1), for example, and are considered to exist in a state where they are not fixed as a certain state.

<Salt>

The salt is not particularly limited and may be appropriately selected depending on the intended purpose. Examples thereof include: alkali metal salts formed with, for example, sodium and potassium; alkaline earth metal salts formed with, for example, calcium and magnesium; and organic amine salts formed with, for example, methylamine, ethylamine, and diethanolamine.

<Synthesis Method 1>

The synthesis method 1 is a method for producing the compound represented by any one of the General Formula (1) to the General Formula (3), a tautomer or geometric isomer thereof, or a salt thereof, the method including: a reaction step of mixing and reacting a substrate that is an oxyindole compound represented by General Formula (6) or General Formula (7) (hereinafter may be referred to as "oxyindole (Aa)" or "oxyindole (Ab)") or a 4-hydroxycoumarin compound represented by General Formula (8) (hereinafter may be referred to as "4-hydroxycoumarin (Ba)") with a carboxylic acid in an organic solvent in the presence of a condensation agent and an amine base; and, if necessary, further includes other steps.

General Formula (6)

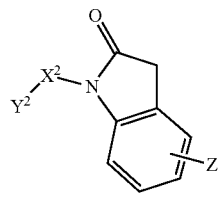

Aa

General Formula (7)

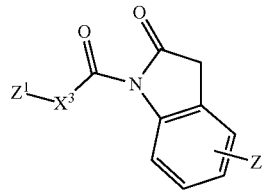

Ab

General Formula (8)

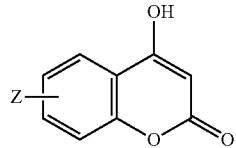

Ba

In the General Formulas (6) to (8), $Z^1$ represents a cyclic, linear, or branched alkyl group which has 8 to 30 carbon atoms and may have a halogen atom.

$X^2$ represents a single bond, —CO—, —CONH—, or —COO—.

$Y^2$ represents a hydrocarbon group which has 1 to 30 carbon atoms and may have —CN, —NO$_2$, an alkoxy group, a halogen atom, or any combination thereof; or a hydrogen atom.

$X^3$ represents a single bond or —NH—.

Z represents a hydrogen atom, a halogen atom, an alkoxy group having 1 to 6 carbon atoms, or a hydrocarbon group having 1 to 20 carbon atoms.

—Oxyindole Compound—

The oxyindole compounds (oxyindole (Aa) and oxyindole (Ab)) are not particularly limited and may be appropriately selected depending on the intended purpose so long as they are represented by the General Formula (6) or (7). The oxyindole compounds may be commercially available products or newly synthesized synthetic products. Examples of the oxyindole compounds include oxyindole compounds expressed by Structural Formulas (85) to (106) below.

(Structural Formula 85)

A-b-01

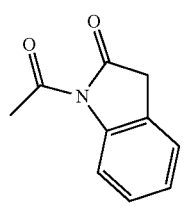

(Structural Formula 86)

A-b-02

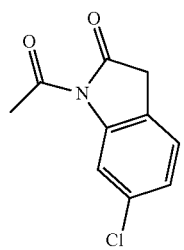

(Structural Formula 87)

A-b-03

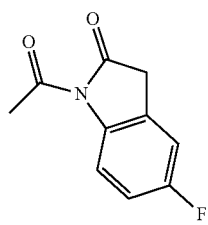

(Structural Formula 88)

A-b-04

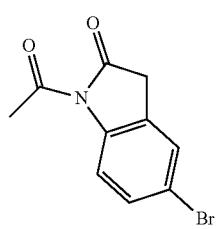

(Structural Formula 89)

A-b-05

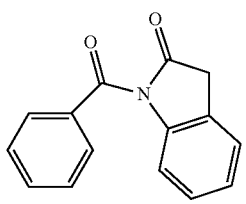

(Structural Formula 90)

A-b-06

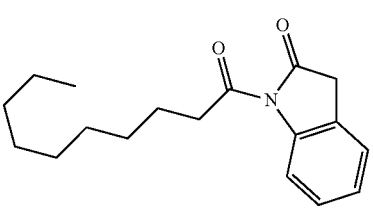

(Structural Formula 91)

A-b-07

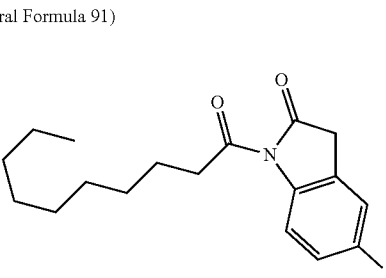

(Structural Formula 92)

A-c-01

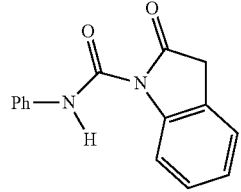

(Structural Formula 93)

A-c-02

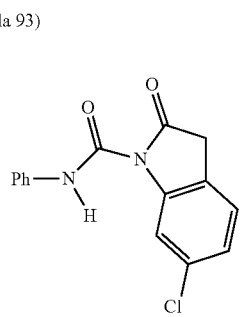

(Structural Formula 94)

A-c-03

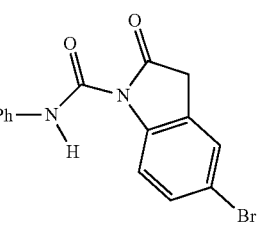

-continued (Structural Formula 95)

A-c-04
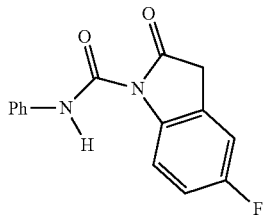

(Structural Formula 96)

A-c-05
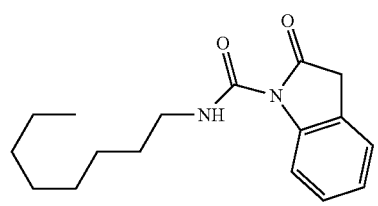

(Structural Formula 97)

A-c-06
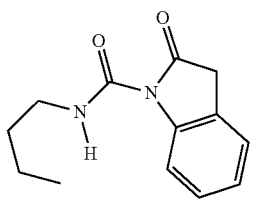

(Structural Formula 98)

A-c-07
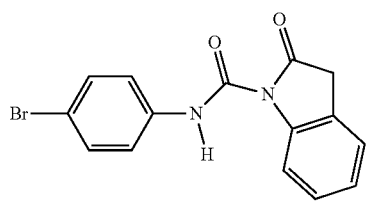

(Structural Formula 99)

A-c-08
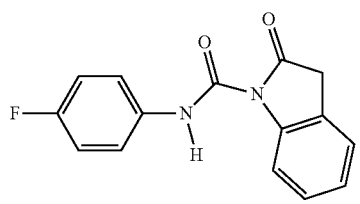

(Structural Formula 100)

A-c-09
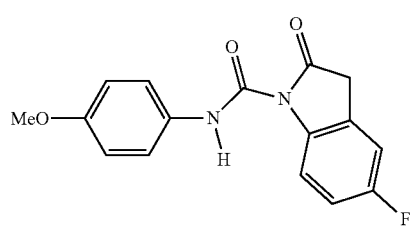

-continued (Structural Formula 101)

A-c-10
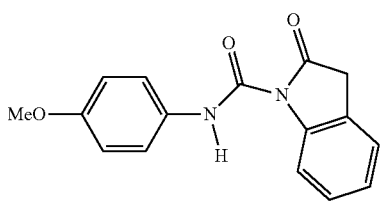

(Structural Formula 102)

A-c-11
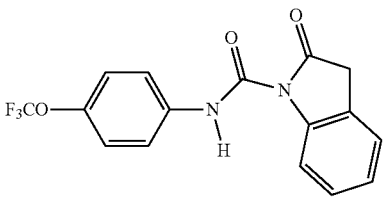

(Structural Formula 103)

A-c-12
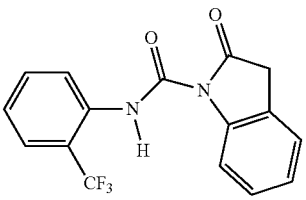

(Structural Formula 104)

A-d-01

(Structural Formula 105)

A-d-02
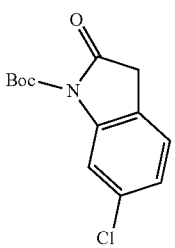

(Structural Formula 106)

A-d-03
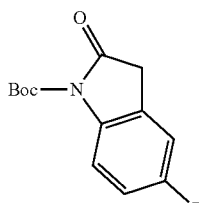

The oxyindoles (A-b-1 to A-b-7) expressed by the Structural Formulas (85) to (91) can be synthesized by allowing a carboxylic anhydride or a carboxylic halide to act on oxyindole (A-e) represented by General Formula (9) below in an organic solvent and mixing a resultant mixture at a temperature range of 50° C. to 120° C. for 12 hours to 24 hours.

General Formula (9)

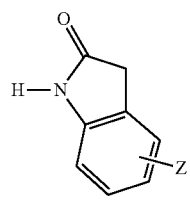

A-e

In the General Formula (9), Z represents a hydrogen atom, a halogen atom, an alkoxy group having 1 to 6 carbon atoms, or a hydrocarbon group having 1 to 20 carbon atoms.

The oxyindole (A-c-1 to A-c-12) expressed by the Structural Formula (92) to (103) can be synthesized by allowing an isocyanate to act on oxyindole (A-e) represented by the General Formula (9) in an organic solvent and mixing a resultant mixture at a temperature range of 50° C. to 120° C. for 12 hours to 24 hours.

The oxyindoles (A-d-1 to A-d-3) expressed by the Structural Formulas (104) to (106) can be synthesized by allowing a carbonic acid ester anhydride to act on oxyindole (A-e) represented by the General Formula (9) in an organic solvent and mixing a resultant mixture at a temperature range of 50° C. to 120° C. for 12 hours to 24 hours.

—Oxyindole (A-e)—

The oxyindole (A-e) is not particularly limited and may be appropriately selected depending on the intended purpose so long as it is represented by the General Formula (9). The oxyindole (A-e) may be a commercially available product or a newly synthesized synthetic product, but is preferably a commercially available product. Examples of the oxyindole (A-e) include 2-oxyindole, 6-chloro-2-oxyindole, 5-bromo-2-oxyindole, and 5-fluoro-2-oxyindole.

—4-Hydroxycoumarin Compound—

The 4-hydroxycoumarin compound (4-hydroxycoumarin (Ba)) is not particularly limited and may be appropriately selected depending on the intended purpose so long as it is represented by General Formula (8). It may be a commercially available product or a newly synthesized synthetic product. Examples of the 4-hydroxycoumarin (Ba) include 6-chloro-4-hydroxycoumarin, 7-methoxy-4-hydroxycoumarin, 6-fluoro-4-hydroxycoumarin, 4-hydroxycoumarin, and 6-methyl-4-hydroxycoumarin.

—Organic Solvent—

The organic solvent is not particularly limited and may be appropriately selected depending on the intended purpose. Examples thereof include: chlorinated alkanes such as dichloromethane and dichloroethane; nitriles such as acetonitrile and propionitrile; sulfoxides such as dimethylsulfoxide; amides such as dimethylformamide; esters such as ethyl acetate; and ethers such as tetrahydrofuran and dioxane. Among them, dichloromethane and acetonitrile are preferable.

—Condensation Agent—

The condensation agent is not particularly limited and may be appropriately selected depending on the intended purpose. Examples thereof include substituted carbodiimides such as N,N'-dicyclohexylcarbodiimide. Among them, N-[3-(dimethylamino)]propyl-N'-ethylcarbodiimide or a hydrochloride thereof is preferable.

—Amine Base—

The amine base is not particularly limited and may be appropriately selected depending on the intended purpose. Examples thereof include tertiary amines such as triethylamine and diisopropylethylamine, and pyridines such as pyridine and 4-(dimethylamino)pyridine. Among them, 4-(dimethylamino)pyridine is preferable.

—Carboxylic Acid—

The carboxylic acid is not particularly limited and may be appropriately selected depending on the intended purpose. It may be a commercially available product or a newly synthesized synthetic product. Examples of the carboxylic acid include compounds expressed by Structural Formulas (107) to (114) below (D-a-01 to D-a-5, D-b-01, D-c-01, and D-c-02).

Structural Formula (107)

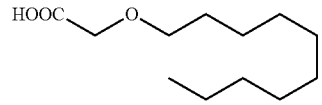

(Compound D-a-01)

Structural Formula (108)

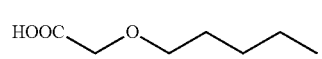

(Compound D-a-02)

Structural Formula (109)

(Compound D-a-03)

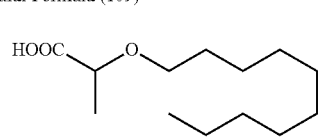

Structural Formula (110)

(Compound D-a-04)

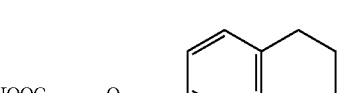

Structural Formula (111)

(Compound D-a-05)

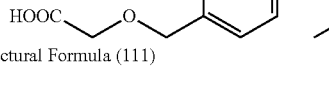

Structural Formula (112)

(Compound D-b-01)

Structural Formula (113)

(Compound D-c-01)

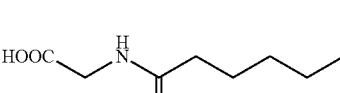

Structural Formula (114)

(Compound D-c-02)

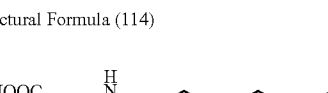

In addition to the compounds expressed by the Structural Formulas (107) to (114), examples of the carboxylic acid include nonanoic acid, decanoic acid, undecanoic acid, dodecanoic acid, methoxyacetic acid, 4-butylcyclohexanecarboxylic acid, N-benzoylglycine, N-Boc-alanine, N-benzoylalanine, N-Boc-glycine, 4-chlorobenzoic acid, 4-fluorobenzoic acid, 4-methoxybenzoic acid, 2-acetoxybenzoic acid, and 10-bromodecanoic acid.

—Other Steps—

The other steps are not particularly limited and may be appropriately selected depending on the intended purpose so long as the effects of the present invention are not impeded. Examples thereof include a step of adding a salt to the compounds belonging to the 3-acyloxyindole compounds or the 3-acyl-4-hydroxycoumarin compounds, tautomers thereof, geometric isomers of the compounds, and the antibacterial compounds; a step of further modifying them; and a step of purifying the compounds belonging to the 3-acyloxyindole compounds or the 3-acyl-4-hydroxycoumarin compounds, tautomers thereof, geometric isomers of the compounds, and the antibacterial compound, or salts thereof.

The reaction temperature in the reaction step of the synthesis method 1 is not particularly limited and may be appropriately selected depending on the intended purpose, but is preferably 0° C. to 120° C., more preferably 0° C. to 50° C., further preferably 20° C. to 30° C.

The reaction time in the reaction step of the synthesis method 1 is not particularly limited and may be appropriately selected depending on the intended purpose, but is preferably 12 hours to 24 hours.

<Synthesis Method 2>

The synthesis method 2 is a method for producing the compound represented by any one of the General Formulas (1) to (3), a tautomer or geometric isomer thereof, or a salt thereof, the method including: a reaction step of mixing and reacting a substrate that is an oxyindole compound represented by General Formula (6) or (7) or a 4-hydroxycoumarin compound represented by the General Formula (8) with a carboxylic acid chloride in an organic solvent in the presence of an amine base without using a condensation agent; and, if necessary, further includes other steps.

—Oxyindole Compound—

The oxyindole compound is similar to those described in the <Synthesis method 1>.

—4-Hydroxycoumarin Compound—

The 4-hydroxycoumarin compound is similar to those described in the <Synthesis method 1>.

—Organic Solvent—

The organic solvent is similar to those described in the <Synthesis method 1>.

—Amine Base—

The amine base is similar to those described in the <Synthesis method 1>.

—Carboxylic Acid Chloride—

The carboxylic acid chloride is not particularly limited and may be appropriately selected depending on the intended purpose. It may be a commercially available product or a newly synthesized synthetic product. Examples of the carboxylic acid chloride include decanoic acid chloride and benzoyl chloride.

—Other Steps—

The other steps are similar to those described in the <Synthesis method 1>.

The reaction temperature in the reaction step of the synthesis method 2 is not particularly limited and may be appropriately selected depending on the intended purpose, but is preferably 0° C. to 120° C., more preferably 0° C. to 50° C., further preferably 20° C. to 30° C.

The reaction time in the reaction step of the synthesis method 2 is not particularly limited and may be appropriately selected depending on the intended purpose, but is preferably 12 hours to 24 hours.

<Synthesis Method 3>

The synthesis method 3 is a method for producing the compound represented by any one of the General Formulas (1) to (3), a tautomer or geometric isomer thereof, or a salt thereof, the method including: a reaction step of mixing and reacting a substrate that is an oxyindole compound represented by General Formula (6) or (7) or a 4-hydroxycoumarin compound represented by the General Formula (8) with a carboxylic anhydride in an organic solvent in the presence of an amine base without using a condensation agent; and, if necessary, further includes other steps.

—Oxyindole Compound—

The oxyindole compound is similar to those described in the <Synthesis method 1>.

—4-Hydroxycoumarin Compound—

The 4-hydroxycoumarin compound is similar to those described in the <Synthesis method 1>.

—Organic Solvent—

The organic solvent is similar to those described in the <Synthesis method 1>.

—Amine Base—

The amine base is similar to those described in the <Synthesis method 1>.

—Carboxylic Anhydride—

The carboxylic anhydride is not particularly limited and may be appropriately selected depending on the intended purpose. It may be a commercially available product or a newly synthesized synthetic product. Examples of the carboxylic anhydride include decanoic anhydride, acetic anhydride, and benzoic anhydride.

—Other Steps—

The other steps are similar to those described in the <Synthesis method 1>.

The reaction temperature in the reaction step of the synthesis method 3 is not particularly limited and may be appropriately selected depending on the intended purpose, but is preferably 0° C. to 120° C., more preferably 0° C. to 50° C., further preferably 20° C. to 30° C.

The reaction time in the reaction step of the synthesis method 3 is not particularly limited and may be appropriately selected depending on the intended purpose, but is preferably 12 hours to 24 hours.

<Synthesis Method 4>

The synthesis method 4 is a method for producing the antibacterial compound represented by the General Formula (5) or a salt thereof, the method including: a reaction step of mixing and reacting a substrate that is a 4-hydroxycoumarin compound represented by the General Formula (8) with a carboxylic acid in an organic solvent in the presence of a condensation agent and an amine base; and, if necessary, further includes other steps.

—4-Hydroxycoumarin Compound—

The 4-hydroxycoumarin compound is similar to those described in the <Synthesis method 1>.

—Organic Solvent—

The organic solvent is similar to those described in the <Synthesis method 1>.

—Condensation Agent—

The condensation agent is similar to those described in the <Synthesis method 1>.

—Amine Base—

The amine base is similar to those described in the <Synthesis method 1>.

—Carboxylic Acid—

The carboxylic acid is similar to those described in the <Synthesis method 1>.

—Other Steps—

The other steps are similar to those described in the <Synthesis method 1>.

The reaction temperature in the reaction step of the synthesis method 4 is not particularly limited and may be appropriately selected depending on the intended purpose, but is preferably 0° C. to 120° C., more preferably 0° C. to 50° C., further preferably 20° C. to 30° C.

The reaction time in the reaction step of the synthesis method 4 is not particularly limited and may be appropriately selected depending on the intended purpose, but is preferably 12 hours to 24 hours.

<Synthesis Method 5>

The synthesis method 4 is a method for producing the antibacterial compound represented by the General Formula (4) or a salt thereof, the method including: a reaction step of mixing and reacting a substrate that is a 4-hydroxycoumarin compound represented by the General Formula (8) with an isocyanate in an organic solvent in the presence of an amine base without using a condensation agent and; and, if necessary, further includes other steps.

—4-Hydroxycoumarin Compound—

The 4-hydroxycoumarin compound is similar to those described in the <Synthesis method 1>.

—Organic Solvent—

The organic solvent is not particularly limited and may be appropriately selected depending on the intended purpose. Examples thereof include: chlorinated alkanes such as dichloromethane and dichloroethane; nitriles such as acetonitrile and propionitrile; sulfoxides such as dimethylsulfoxide; amides such as dimethylformamide; esters such as ethyl acetate; and ethers such as tetrahydrofuran and dioxane. Among them, dichloromethane and toluene are preferable.

—Amine Base—

The amine base is similar to those described in the <Synthesis method 1>.

—Isocyanate—

The isocyanate is not particularly limited and may be appropriately selected depending on the intended purpose. It may be a commercially available product or a newly synthesized synthetic product. Examples of the isocyanate include octyl isocyanate, decyl isocyanate, and dodecyl isocyanate.

—Other Steps—

Examples of the other steps include a step of adding a salt to the compounds belonging to the 3-acyl-4-hydroxycoumarin compounds; a step of further modifying them; and a step of purifying the compounds belonging to the 3-acyl-4-hydroxycoumarin compounds, or salts thereof.

The reaction temperature in the reaction step of the synthesis method 5 is not particularly limited and may be appropriately selected depending on the intended purpose, but is preferably 0° C. to 120° C., more preferably 0° C. to 50° C., further preferably 20° C. to 30° C.

The reaction time in the reaction step of the synthesis method 5 is not particularly limited and may be appropriately selected depending on the intended purpose, but is preferably 12 hours to 24 hours.

(Antibacterial Agent)

An antibacterial agent of the present invention contains the compound, the tautomer or geometric isomer thereof, or the salt thereof of the present invention; or the antibacterial compound or the salt thereof of the present invention; or both thereof. The antibacterial agent of the present invention further contains other ingredients, if necessary.

<Compound, Tautomer or Geometric Isomer Thereof, or Salt Thereof; and Antibacterial Compound or Salt Thereof>

An amount of the compound, the tautomer or geometric isomer thereof, or the salt thereof of the present invention; or the antibacterial compound or the salt thereof of the present invention; or both thereof contained in the antibacterial agent is not particularly limited and may be appropriately selected depending on the intended purpose. Also, the antibacterial agent may be the compound, the tautomer or geometric isomer thereof, or the salt thereof of the present invention itself, or may be the antibacterial compound or the salt thereof of the present invention itself, or may consist of both thereof.

<Other Ingredients>

The other ingredients are not particularly limited and may be appropriately selected depending on the intended purpose so long as the effects of the present invention are not impeded. Examples thereof include pharmacologically acceptable carriers such as ethanol, water, and starch.

An amount of the other ingredients contained in the antibacterial agent is not particularly limited and may be appropriately selected depending on the intended purpose so long as the effects of the compound and the antibacterial compound are not impeded.

<Target>

A target to which the antibacterial agent exhibits antibacterial activity is not particularly limited and may be appropriately selected depending on the intended purpose. It is preferably drug-resistant bacteria, more preferably multiply antibiotic-resistant bacteria, further preferably MRSA, VRE, or *C. difficile*, or any combination thereof.

<Dosage Form>

The dosage form of the antibacterial agent is not particularly limited and may be appropriately selected depending on the intended purpose. Examples of the dosage form include an oral solid preparation, an oral liquid preparation, an injection and an inhalation powder.

—Oral Solid Preparation—

The oral solid preparation is not particularly limited and may be appropriately selected depending on the intended purpose. Examples of the oral solid preparation include a tablet, a coated tablet, granules, powder and a capsule.

The method for producing the oral solid preparation is not particularly limited and may be a routine method. For example, the oral solid preparation can be produced by adding an excipient and, if necessary, the above other ingredients and various additives to the above compound. Here, the excipient is not particularly limited and may be appropriately selected depending on the intended purpose. Examples of the excipient include lactose, sucrose, sodium chloride, glucose, starch, calcium carbonate, kaolin, microcrystalline cellulose and silicic acid. The additives are not particularly limited and may be appropriately selected depending on the intended purpose. Examples of the additives include a binding agent, a disintegrating agent, a lubricating agent, a coloring agent and a sweetening/flavoring agent.

The binding agent is not particularly limited and may be appropriately selected depending on the intended purpose. Examples of the binding agent include water, ethanol, propanol, simple syrup, glucose liquid, starch liquid, gelatine liquid, carboxymethylcellulose, hydroxypropylcellulose, hydroxypropylstarch, methylcellulose, ethylcellulose, shellac, calcium phosphate and polyvinylpyrrolidone.

The disintegrating agent is not particularly limited and may be appropriately selected depending on the intended purpose. Examples of the disintegrating agent include dry starch, sodium alginate, powdered agar, sodium hydrogencarbonate, calcium carbonate, sodium lauryl sulfate, monoglyceride stearate and lactose.

The lubricating agent is not particularly limited and may be appropriately selected depending on the intended purpose. Examples of the lubricating agent include purified talc, stearic acid salts, borax and polyethylene glycol.

The coloring agent is not particularly limited and may be appropriately selected depending on the intended purpose. Examples of the coloring agent include titanium oxide and iron oxide.

The sweetening/flavoring agent is not particularly limited and may be appropriately selected depending on the intended purpose. Examples of the sweetening/flavoring agent include sucrose, orange peel, citric acid and tartaric acid.

—Oral Liquid Preparation—

The oral liquid preparation is not particularly limited and may be appropriately selected depending on the intended purpose. Examples of the oral liquid preparation include an internal liquid, syrup and elixir.

The method for producing the oral liquid preparation is not particularly limited and may be a routine method. For example, the oral liquid preparation can be produced by adding additives to the above compound and optionally used other ingredients described above. Here, the additives are not particularly limited and may be appropriately selected depending on the intended purpose. Examples of the additives include a sweetening/flavoring agent, a buffer and a stabilizing agent.

The sweetening/flavoring agent is not particularly limited and may be appropriately selected depending on the intended purpose. Examples of the sweetening/flavoring agent include sucrose, orange peel, citric acid and tartaric acid.

The buffer is not particularly limited and may be appropriately selected depending on the intended purpose. Examples of the buffer include sodium citrate.

The stabilizing agent is not particularly limited and may be appropriately selected depending on the intended purpose. Examples of the stabilizing agent include tragacanth, gum arabic and gelatin.

—Injection—

The injection is not particularly limited and may be appropriately selected depending on the intended purpose. Examples of the injection include a solution, a suspension and a solid preparation reconstituted upon use.

The method for producing the injection is not particularly limited and may be a routine method. For example, the injection can be produced by adding a pH adjuster, a buffer, a stabilizing agent, a tonicity agent, a local anesthetic, etc. to the above compound and optionally used other ingredients described above. Here, the pH adjuster or buffer is not particularly limited and may be appropriately selected depending on the intended purpose. Examples of the pH adjuster or buffer include sodium citrate, sodium acetate and sodium phosphate. The stabilizing agent is not particularly limited and may be appropriately selected depending on the intended purpose. Examples of the stabilizing agent include sodium pyrosulfite, EDTA, thioglycolic acid and thiolactic acid. The tonicity agent is not particularly limited and may be appropriately selected depending on the intended purpose. Examples of the tonicity agent include sodium chloride and glucose. The local anesthetic is not particularly limited and may be appropriately selected depending on the intended purpose. Examples of the local anesthetic include procaine hydrochloride and lidocaine hydrochloride.

<Administration>

Regarding the antibacterial agent, the administration method, the administration dose, the timing of administration and the subject to be administered are not particularly limited and may be appropriately selected depending on the intended purpose.

The administration method is not particularly limited and may be appropriately selected depending on the intended purpose. Examples of the administration method include oral administration, injection and inhalation.

The administration dose is not particularly limited and may be appropriately selected considering various factors of a subject to be administered, such as the age, body weight, constitution, symptom and the presence or absence of administration of a drug containing other active ingredients.

The animal species serving as the subject to be administered is not particularly limited and may be appropriately selected depending on the intended purpose. Examples of the animal species include human, monkey, pig, bovine, sheep, goat, dog, cat, mouse, rat and bird. Among them, the antibacterial agent is suitably administered to human.

<Antibacterial Activity>

The target to which the antibacterial agent exhibits antibacterial activity is, as described above, not particularly limited and may be appropriately selected depending on the intended purpose. It is preferably drug-resistant bacteria, more preferably multiply antibiotic-resistant bacteria, further preferably MRSA, VRE, or *C. difficile*, or any combination thereof. However, when the target is bacteria resistant to a specific drug (e.g., vancomycin-resistant bacteria), the antibacterial agent is preferably ineffective to bacteria susceptible to the drug (e.g., vancomycin-susceptible bacteria).

The method for measuring the antibacterial activity is not particularly limited and may be appropriately selected depending on the intended purpose. Examples thereof include a method in which the minimum inhibitory concentration (hereinafter may be referred to as "MIC") is measured.

The method for measuring the MIC is not particularly limited and may be appropriately selected from known methods.

The MIC of the antibacterial agent against the drug-resistant bacteria, especially the multiply antibiotic-resistant bacteria, is not particularly limited and may be appropriately selected depending on, for example, the type of the bacteria to be targeted. The MIC is preferably lower than 8 mg/L, more preferably lower than 4 mg/L, still more preferably lower than 2 mg/L, particularly preferably lower than 1 mg/L. When the MIC is 8 mg/L or higher, the antibacterial agent cannot inhibit the growth of the bacteria in some cases, since the antibacterial activity is low.

Also, in the present invention, the description "the antibacterial agent of the present invention is ineffective to drug-susceptible bacteria" also encompasses the case where the antibacterial activity against the drug-susceptible bacteria is low. The MIC of the antibacterial agent against the drug-susceptible bacteria is not particularly limited and may be appropriately selected depending on the intended purpose depending on, for example, the type of the bacteria. It is preferably 8 mg/L or higher.

<Use>

The antibacterial agent may be used alone or in combination with a drug containing other active ingredients. Also, the antibacterial agent may be formulated into a drug containing other active ingredients before use.

The antibacterial agent preferably exhibits no antibacterial activity against drug-susceptible bacteria in order to prevent the drug-susceptible bacteria from becoming resistant. Thus, particularly preferably, the antibacterial agent is used in combination with or is formulated into a drug containing other active ingredients that exhibits an antibacterial activity against drug-susceptible bacteria only.

<Applications>

The antibacterial agent contains at least one of the compounds belonging to the 3-acyloxyindole compounds or the 3-acyl-4-hydroxycoumarin compounds represented by the General Formulas (1) to (5) and has antibacterial activity, and thus can suitably be used for an infectious disease therapeutic drug of the present invention.

(Infectious Disease Therapeutic Drug)

An infectious disease therapeutic drug of the present invention contains the antibacterial agent of the present invention; and, if necessary, further contains other ingredients.

<Antibacterial Agent>

An amount of the antibacterial agent of the present invention contained in the infectious disease therapeutic drug is not particularly limited and may be appropriately selected depending on the intended purpose. Also, the infectious disease therapeutic drug may be the antibacterial agent of the present invention itself.

<Other Ingredients>

The other ingredients are not particularly limited and may be appropriately selected depending on the intended purpose so long as the effects of the present invention are not impeded. Examples thereof include pharmacologically acceptable carriers such as ethanol, water and starch.

An amount of the other ingredients contained in the infectious disease therapeutic drug is not particularly limited and may be appropriately selected depending on the intended purpose from a range within which the effects of the compounds belonging to the 3-acyloxyindole compounds or the 3-acyl-4-hydroxycoumarin compounds represented by the General Formulas (1) to (5) are not impeded.

<Use>

The infectious disease therapeutic drug may be used alone or in combination with a drug containing other active ingredients. Also, the infectious disease therapeutic drug may be formulated into a drug containing other active ingredients before use.

The infectious disease therapeutic drug preferably exhibits no antibacterial activity against drug-susceptible bacteria in order to prevent the drug-susceptible bacteria from becoming resistant. Thus, preferably, the infectious disease therapeutic drug is used in combination with or is formulated into a drug containing other active ingredients that exhibits antibacterial activity against drug-susceptible bacteria only.

EXAMPLES

The present invention will next be described in detail by way of Examples, which should not be construed as limiting the present invention thereto.

Preparation Example 1

Synthesis of D-a-01 (Decyloxyacetic Acid)

Bromodecane (commercially available product, 3.00 g, 13.6 mmol) and methyl glycolate (commercially available product, 1.34 g, 15.0 mmol, 1.1 equiv.) were dissolved in a solvent mixture of dimethylformamide (5 mL)-tetrahydrofuran (commercially available product, 5 mL), and sodium hydride (0.60 g, 1.1 equiv.) was added to the resultant solution at room temperature.

The resultant mixture was stirred at 60° C. for 12 hours and then the solvent was evaporated under reduced pressure.

The obtained oily substance was dissolved in ethanol (15 mL). Next, an aqueous solution of sodium hydroxide (1.1 g, 2.7 mmol, 2 equiv.) in water (5 mL) was added to the resultant solution at room temperature.

After the resultant mixture had been stirred at room temperature for 12 hours, 6 mol/L hydrochloric acid (0.5 mL) was added to the mixture. The solvent of the mixture was evaporated under reduced pressure. The resultant product was purified through silica gel column chromatography using an ethyl acetate-hexane solvent mixture, to thereby obtain D-a-01 (decyloxyacetic acid) expressed by Structural Formula (107) (2.35 g, 80%).

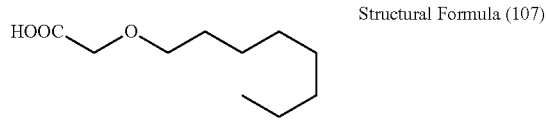

Structural Formula (107)

D-a-01 (Decyloxyacetic Acid)

1H NMR (300 Hz) 0.86 (t, 3H, J=6.6 Hz), 1.19-1.68 (m, 16H), 3.54 (t, 2H, J=6.6 Hz), 4.11 (s, 2H), 8.63-10.13 (br, 1H)

13C NMR (75 Hz) 14.1, 22.6, 25.9, 29.2, 29.3, 29.35, 29.38, 29.5, 31.8, 67.6, 72.1, 175.1

Preparation Example 2

Synthesis of D-a-02 (Pentyloxyacetic Acid)

D-a-02 (pentyloxyacetic acid) expressed by Structural Formula (108) was obtained in the same manner as in Preparation Example 1 except that bromodecane in Preparation Example 1 was changed to bromopentane (commercially available product).

Structural Formula (108)

D-a-02 (Pentyloxyacetic Acid)

1H NMR (300 Hz) 0.89 (t, 3H, J=6.6 Hz), 1.21-1.69 (m, 6H), 3.54 (t, 2H, J=6.6 Hz), 4.11 (s, 2H), 9.78-10.32 (br, 1H)

Preparation Example 3

Synthesis of D-a-03 (Decyloxypropionic Acid)

D-a-03 (decyloxypropionic acid) expressed by Structural Formula (109) was obtained in the same manner as in Preparation Example 1 except that methyl glycolate in Preparation Example 1 was changed to ethyl lactate (commercially available product).

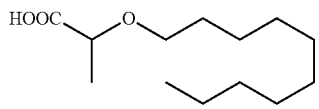

Structural Formula (109)

D-a-03 (Decyloxypropionic Acid)

1H NMR (300 Hz) 0.87 (t, 3H, J=6.9 Hz), 1.18-1.50 (m, 14H), 1.48 (d, 3H, J=6.6 Hz), 1.56-1.72 (m, 2H), 3.35-3.56 (m, 2H), 5.31 (q, 1H, J=6.6 Hz), 8.65-10.14 (br, 1H)

Preparation Example 4

Synthesis of D-a-04 (4-Butylphenylmethoxyacetic Acid)

D-a-04 (4-butylphenylmethoxyacetic acid) expressed by Structural Formula (110) was obtained in the same manner as in Preparation Example 1 except that bromodecane in Preparation Example 1 was changed to 4-butylbenzyl chloride (commercially available product).

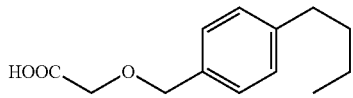

Structural Formula (110)

D-a-04 (4-Butylphenylmethoxyacetic Acid)

1H NMR (300 Hz) 092 (t, 3H, J=6.6 Hz), 1.24-1.64 (m, 4H), 2.62 (t, 2H, J=7.5 Hz), 4.70 (s, 2H), 4.94 (s, 2H), 8.55-10.10 (br, 1H)

Preparation Example 5

Synthesis of D-a-05 (Octyloxyacetic Acid)

D-a-05 (octyloxyacetic acid) expressed by Structural Formula (111) was obtained in the same manner as in Preparation Example 1 except that bromodecane in Preparation Example 1 was changed to bromooctane (commercially available product).

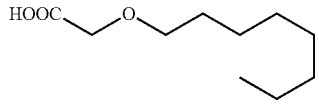

Structural Formula (111)

D-a-05 (Octyloxyacetic Acid)

1H NMR (300 Hz) 0.85 (t, 3H, J=6.6 Hz), 1.15-1.65 (m, 12H), 3.52 (t, 2H, J=6.9 Hz), 4.09 (s, 2H), 10.42-10.52 (br, 1H)

13C NMR (75 Hz) 14.0, 22.5, 25.8, 29.1, 29.6, 29.3, 31.7, 67.6, 72.1, 175.8

Preparation Example 6

Synthesis of D-b-01 (Decylthioacetic Acid)

Bromodecane (commercially available product, 1.00 g, 4.5 mmol) and methyl thioglycolate (commercially available product, 0.53 g, 5.0 mmol, 1.1 equiv.) were dissolved in a solvent mixture of dimethylformamide (3 mL)-tetrahydrofuran (3 mL), and sodium hydride (0.20 g, 1.1 equiv.) was added to the resultant solution at room temperature.

The resultant mixture was stirred at 60° C. for 12 hours and then the solvent was evaporated under reduced pressure.

The obtained oily substance was dissolved in ethanol (5 mL). Next, an aqueous solution of sodium hydroxide (0.36 g, 0.9 mmol, 2 equiv.) in water (2 mL) was added to the resultant solution at room temperature.

After the resultant mixture had been stirred at room temperature for 12 hours, 6 mol/L hydrochloric acid (0.3 mL) was added to the mixture. The solvent of the mixture was evaporated under reduced pressure. The resultant product was purified through silica gel column chromatography using an ethyl acetate-hexane solvent mixture, to thereby obtain D-b-01 (decylthioacetic acid) expressed by Structural Formula (112) (0.78 g, 75%).

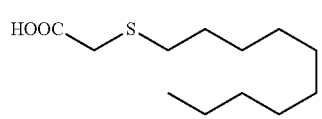

Structural Formula (112)

D-b-01 (Decylthioacetic Acid)

1H NMR (300 Hz) 0.87 (t, 3H, J=6.6 Hz), 1.15-1.68 (m, 16H), 2.65 (t, 2H, 7.5 Hz), 3.25 (s, 2h), 8.95-10.22 (br, 1H)
13C NMR (75 Hz) 14.1, 22.6, 28.7, 28.9, 29.1, 29.3, 29.45, 29.50, 31.9, 32.8, 33.5, 176.8

Preparation Example 7

Synthesis of D-c-01 (N-Decanoylglycine)

Glycine ethyl hydrochloride (commercially available product, 1.40 g, 10.0 mmol) was mixed with tetrahydrofuran (commercially available product, 10 mL), and sodium hydrogen carbonate (1.68 g, 20.0 mmol, 2 equiv.) was added to the resultant mixture at room temperature. Decanoic acid chloride (commercially available product, 2.30 mL, 11.0 mmol, 1.1 equiv.) was added dropwise to this mixture at room temperature. After the resultant mixture had been stirred at room temperature for 3 hours, the solvent was removed under reduced pressure.

The obtained oily substance was dissolved in ethanol (10 mL). Next, an aqueous solution of sodium hydroxide (0.80 g, 20.0 mmol, 2 equiv.) in water (3 mL) was added to the resultant solution at room temperature.

After the resultant mixture had been stirred at room temperature for 12 hours, 6 mmol/L hydrochloric acid (0.5 mL) was added to the mixture. The solvent of the mixture was evaporated under reduced pressure. The resultant product was purified through silica gel column chromatography using an ethyl acetate-hexane solvent mixture, to thereby obtain D-c-01 (N-decanoylglycine) expressed by Structural Formula (113) (1.65 g, 72%).

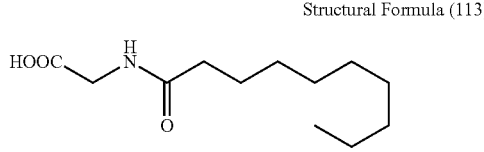

Structural Formula (113)

D-c-01 (N-Decanoylglycine)

1H NMR (300 Hz) 0.88 (t, 3H, J=6.6 Hz), 1.10-1.75 (m, 14H), 2.24 (t, 2H, J=7.5 Hz), 4.85 (s, 2H), 6.25-6.45 (br, 1H), 9.12-10.60 (br, 1H)

Preparation Example 8

Synthesis of D-c-02 (N-Decanoylalanine)

D-c-02 (N-decanoylalanine) expressed by Structural Formula (114) was obtained in the same manner as in Preparation Example 7 except that glycine ethyl hydrochloride in Preparation Example 6 was changed to alanine methyl ester hydrochloride (commercially available product).

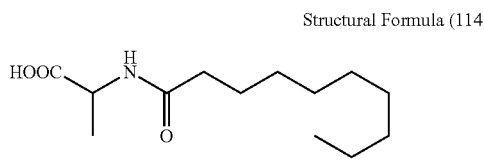

Structural Formula (114)

D-c-02 (N-Decanoylalanine)

1H NMR (300 Hz) 0.87 (t, 3H, J=6.6 Hz), 1.10-1.70 (m, 14H), 1.51 (d, 3H, J=7.2 Hz), 2.25 (t, 2H, J=7.5 Hz), 5.80-5.95 (m, 1H), 6.30 (d, 1H, J=7.5 Hz), 9.10-10.50 (br, 1H)

Preparation Example 9

Synthesis of A-b-06 (N-decanoyl-2-oxyindole)

Oxyindole (commercially available product, 270 mg, 2.0 mmol) and decanoic anhydride (commercially available product, 0.82 mL, 2.2 mmol, 1.1 equiv.) were mixed with toluene (4 mL) at room temperature.

After the resultant mixture had been stirred at 110° C. for 12 hours, the solvent of the mixture was evaporated under reduced pressure. The resultant product was purified through silica gel column chromatography using an ethyl acetate-hexane solvent mixture, to thereby obtain A-b-06 (N-decanoyl-2-oxyindole) expressed by Structural Formula (90) (0.52 g, 90%).

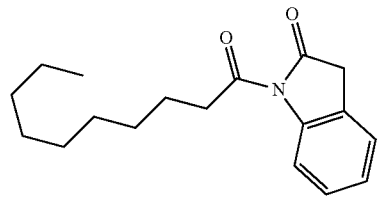

Structural Formula (90)

A-b-06 (N-decanoyl-2-oxyindole)

1H NMR (300 Hz) 0.87 (t, 3H, J=6.6 Hz), 1.19-1.78 (m, 14h), 3.04 (t, 2H, J=7.2 Hz), 3.70 (s, 2H), 7.12-7.35 (m, 3H), 8.21 (d, 1H, J=8.1 Hz)

Preparation Example 10

Synthesis of A-b-01 (N-acetyl-2-oxyindole)

A-b-01 (N-acetyl-2-oxyindole) expressed by Structural Formula (85) was obtained in the same manner as in Preparation Example 9 except that decanoic anhydride in Preparation Example 9 was changed to acetic anhydride.

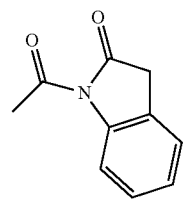

Structural Formula (85)

A-b-01 (N-acetyl-2-oxyindole)

1H NMR (300 Hz) 2.64 (s, 1H), 3.69 (s, 2H), 7.14 (dd, 1H, J=1.2, 7.5 Hz), 7.24 (d, 1H, J=7.5 Hz), 7.31 (t, 1H, J=8.1 Hz), 8.21 (d, 1H, J=8.1 Hz)

Preparation Example 11

Synthesis of A-b-02 (N-acetyl-6-chloro-2-oxyindole)

A-b-02 expressed by Structural Formula (86) was obtained in the same manner as in Preparation Example 9 except that decanoic anhydride and oxyindole in Preparation Example 9 were changed to acetic anhydride and 6-chloro-2-oxyindole (commercially available product), respectively.

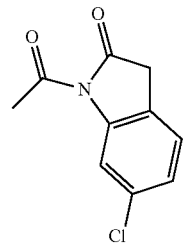

Structural Formula (86)

A-b-02 (N-acetyl-6-chloro-2-oxyindole)

1H NMR (300 Hz) 2.65 (s, 3H), 3.67 (s, 2H), 7.05-7.30 (m, 2H), 8.24 (dd, 1H, J=1.8, 7.8 Hz)

Preparation Example 12

Synthesis of A-b-03 (N-acetyl-5-fluoro-2-oxyindole)

A-b-03 (N-acetyl-5-fluoro-2-oxyindole) expressed by Structural Formula (87) was obtained in the same manner as in Preparation Example 9 except that decanoic anhydride and oxyindole in Preparation Example 9 were changed to acetic anhydride and 5-fluoro-2-oxyindole (commercially available product), respectively.

Structural Formula (87)

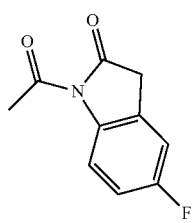

A-b-03 (N-acetyl-5-fluoro-2-oxyindole)

1H NMR (300 Hz) 2.65 (s, 3H), 3.70 (s, 2H), 6.96-7.26 (m, 2H), 8.20 (dd, 1H, J=4.8, 8.1 Hz)

Preparation Example 13

Synthesis of A-b-04 (N-acetyl-5-bromo-2-oxyindole)

A-b-04 (N-acetyl-5-bromo-2-oxyindole) expressed by Structural Formula (88) was obtained in the same manner as in Preparation Example 9 except that decanoic anhydride and oxyindole in Preparation Example 9 were changed to acetic anhydride and 5-bromo-2-oxyindole (commercially available product), respectively.

Structural Formula (88)

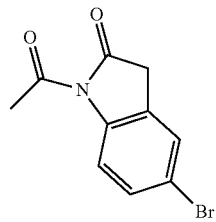

A-b-04 (N-acetyl-5-bromo-2-oxyindole)

1H NMR (300 Hz) 2.65 (s, 3H), 3.70 (s, 2H), 7.39-7.45 (m, 2H), 8.10 (d, 1H, J=8.7 Hz)

Preparation Example 14

Synthesis of A-b-05 (N-benzoyl-2-oxyindole)

A-b-05 (N-benzoyl-2-oxyindole) expressed by Structural Formula (89) was obtained in the same manner as in Preparation Example 9 except that decanoic anhydride in Preparation Example 9 was changed to benzoic anhydride (commercially available product).

Structural Formula (89)

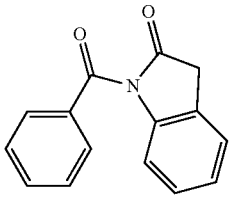

A-b-05 (N-benzoyl-2-oxyindole)

1H NMR (300 Hz) 3.76 (s, 2H), 7.17-7.82 (m, 6H), 7.20 (dd, 1H, J=1.2, 7.5 Hz), 8.13 (d, 2H, J=6.9 Hz)

Preparation Example 15

Synthesis of A-b-07 (N-decanoyl-5-fluoro-2-oxyindole)

A-b-07 (N-decanoyl-5-fluoro-2-oxyindole) expressed by Structural Formula (91) was obtained in the same manner as in Preparation Example 9 except that oxyindole in Preparation Example 9 was changed to 5-fluoro-2-oxyindole (commercially available product).

Structural Formula (91)

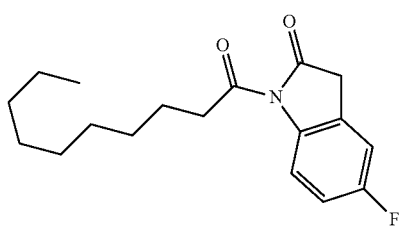

A-b-07 (N-decanoyl-5-fluoro-2-oxyindole)

1H NMR (300 Hz) 0.87 (t, 3H, J=6.6 Hz), 1.20-1.78 (m, 14h), 3.04 (t, 2H, J=7.2 Hz), 3.71 (s, 2H), 6.96-7.24 (m, 2H), 8.20 (dd, 1H, J=4.8, 8.1 Hz)

Preparation Example 16

Synthesis of A-d-01 (N-Boc-2-oxyindole)

A-d-01 (N-Boc-2-oxyindole) expressed by Structural Formula (104) was obtained in the same manner as in Preparation Example 9 except that decanoic anhydride in Preparation Example 9 was changed to di-tert-butyl dicarbonate (commercially available product).

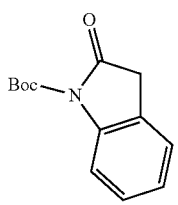

A-d-01 (N-Boc-2-oxyindole)

1H NMR (300 Hz) 1.63 (s, 9H), 3.63 (s, 2H), 7.09-7.32 (m, 2H), 7.23 (d, 1H, J=7.5 Hz), 7.77 (d, 1H, J=7.8 Hz)

Preparation Example 17

Synthesis of A-d-02 (N-Boc-6-chloro-2-oxyindole)

A-d-02 expressed by Structural Formula (105) was obtained in the same manner as in Preparation Example 9 except that decanoic anhydride and oxyindole in Preparation Example 9 were changed to di-tert-butyl dicarbonate (commercially available product) and 6-chloro-2-oxyindole (commercially available product), respectively.

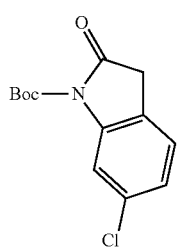

Structural Formula (105)

A-d-02 (N-Boc-6-chloro-2-oxyindole)

1H NMR (300 Hz) 1.63 (s, 9H), 3.60 (s, 2H), 7.10 (dd, 1H, J=1.8, 8.1 Hz), 7.15 (d, 1H, J=8.1 Hz), 7.85 (d, 1H, J=1.8 Hz)

Preparation Example 18

Synthesis of A-d-03 (N-Boc-5-fluoro-2-oxyindole)

A-d-03 (N-Boc-5-fluoro-2-oxyindole) expressed by Structural Formula (106) was obtained in the same manner as in Preparation Example 9 except that decanoic anhydride and oxyindole in Preparation Example 9 were changed to di-tert-butyl dicarbonate (commercially available product) and 5-fluoro-2-oxyindole (commercially available product), respectively.

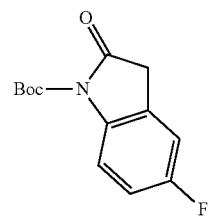

Structural Formula (106)

A-d-03 (N-Boc-5-fluoro-2-oxyindole)

1H NMR (300 Hz) 1.63 (s, 9H), 3.64 (s, 2H), 6.92-7.04 (m, 2H), 7.76 (dd, 1H, J=4.8, 9.0 Hz)

Preparation Example 19

Synthesis of A-c-01 (N-(phenylaminocarbonyl)-2-oxyindole)

Oxyindole (commercially available product, 270 mg, 2.0 mmol) and phenyl isocyanate (commercially available product, 0.24 mL, 2.2 mmol, 1.1 equiv.) were mixed with toluene (4 mL) at room temperature.

After the resultant mixture had been stirred at 110° C. for 12 hours, the solvent of the mixture was evaporated under reduced pressure. The resultant product was purified through silica gel column chromatography using an ethyl acetate-hexane solvent mixture, to thereby obtain A-c-01 (N-(phenylaminocarbonyl)-2-oxyindole) expressed by Structural Formula (92) (0.46 g, 92%).

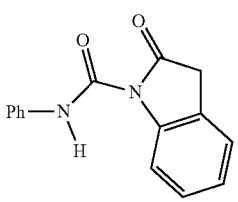

Structural Formula (92)

A-c-01 (N-(phenylaminocarbonyl)-2-oxyindole)

1H NMR (300 Hz) 3.77 (s, 2H), 7.11-7.61 (m, 8H), 8.64 (d, 1H, J=8.4 Hz), 10.68 (bs, 1H)

Preparation Example 20

Synthesis of A-c-02

A-c-02 expressed by Structural Formula (93) was obtained in the same manner as in Preparation Example 19 except that oxyindole in Preparation Example 19 was changed to 6-chloro-2-oxyindole (commercially available product).

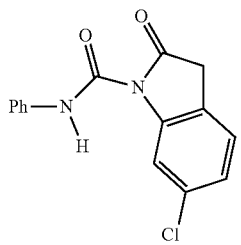

A-c-02

1H NMR (300 Hz) 3.75 (s, 2H), 7.11-7.22 (m, 3H), 7.37 (t, 3H, J=7.5 Hz), 7.58 (dd, 2H, J=1, 2, 7.5 Hz), 8.37 (d, 1H, 1.2 Hz), 10.58 (s, 1H)

Preparation Example 21

Synthesis of A-c-03 (N-(phenylaminocarbonyl)-5-bromo-2-oxyindole)

A-c-03 (N-(phenylaminocarbonyl)-5-bromo-2-oxyindole) expressed by Structural Formula (94) was obtained in the same manner as in Preparation Example 19 except that oxyindole in Preparation Example 19 was changed to 5-bromo-2-oxyindole (commercially available product).

Structural Formula (94)

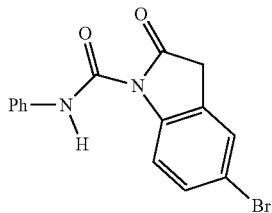

A-c-03 (N-(phenylaminocarbonyl)-5-bromo-2-oxyindole)

1H NMR (300 Hz) 3.76 (s, 2H), 7.11-7.45 (m, 8H), 8.10 (d, 1H, J=8.7 Hz)

Preparation Example 22

Synthesis of A-c-04 (N-(phenylaminocarbonyl)-5-fluoro-2-oxyindole)

A-c-04 (N-(phenylaminocarbonyl)-5-fluoro-2-oxyindole) expressed by Structural Formula (95) was obtained in the same manner as in Preparation Example 19 except that oxyindole in Preparation Example 19 was changed to 5-fluoro-2-oxyindole (commercially available product).

Structural Formula (95)

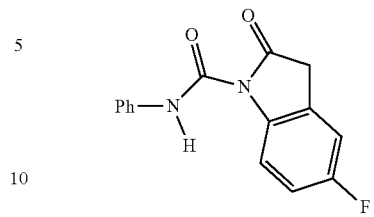

A-c-04 (N-(phenylaminocarbonyl)-5-fluoro-2-oxyindole)

1H NMR (300 Hz) 3.80 (s, 2H), 6.99-7.10 (m, 3H), 7.35 (t, 2H, J=7.5 Hz), 7.59 (dd, 1H, J=1.2, 7.5 Hz), 8.29 (dd, 1H, J=4.8, 9.0 Hz), 10.46-10.76 (br, 1H)

Preparation Example 23

Synthesis of A-c-05 (N-(octylaminocarbonyl)-2-oxyindole)

A-c-05 (N-(octylaminocarbonyl)-2-oxyindole) expressed by Structural Formula (96) was obtained in the same manner as in Preparation Example 19 except that phenyl isocyanate in Preparation Example 19 was changed to octyl isocyanate (commercially available product).

Structural Formula (96)

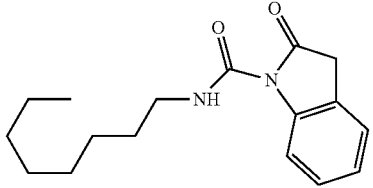

A-c-05 (N-(octylaminocarbonyl)-2-oxyindole)

1H NMR (300 Hz) 0.87 (t, 3H, J=6.6 Hz), 1.18-1.68 (m, 12H), 3.40 (q, 2H, J=6.9 Hz), 3.70 (s, 2H), 7.13 (dd, 1H, J=0.9, 7.5 Hz), 7.23 (dd, 1H, J=0.9, 7.5 Hz), 7.31 (t, 1H, J=8.1 Hz), 8.24 (d, 1H, 8.1 Hz), 8.47-8.67 (br, 1H)

Preparation Example 24

Synthesis of A-c-06 (N-(butylaminocarbonyl)-2-oxyindole)

A-c-06 (N-(butylaminocarbonyl)-2-oxyindole) expressed by Structural Formula (97) was obtained in the same manner as in Preparation Example 19 except that phenyl isocyanate in Preparation Example 19 was changed to butyl isocyanate (commercially available product).

Structural Formula (97)

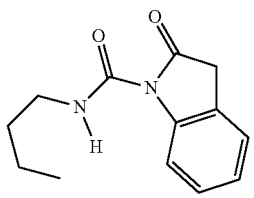

A-c-06 (N-(butylaminocarbonyl)-2-oxyindole)

1H NMR (300 Hz) 0.96 (t, 3H, J=7.2 Hz), 1.34-1.74 (m, 4H), 3.39 (q, 2H, J=6.9 Hz), 3.69 (s, 2H), 7.13 (dd, 1H, J=0.9, 7.5 Hz), 7.24 (d, 1H, J=7.5 Hz), 7.30 (t, 1H, J=8.1 Hz), 8.24 (d, 1H, 8.1 Hz), 8.48-8.63 (br, 1H)

Preparation Example 25

Synthesis of A-c-07 (N-(4-bromophenylaminocarbonyl)-2-oxyindole)

A-c-07 (N-(4-bromophenylaminocarbonyl)-2-oxyindole) expressed by Structural Formula (98) was obtained in the same manner as in Preparation Example 19 except that phenyl isocyanate in Preparation Example 19 was changed to 4-bromophenyl isocyanate (commercially available product).

Structural Formula (98)

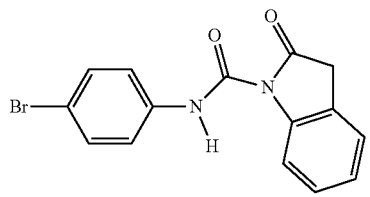

A-c-07 (N-(4-bromophenylaminocarbonyl)-2-oxyindole)

1H NMR (300 Hz) 3.78 (s, 2H), 7.20 (dd, 1H, J=0.9, 7.5 Hz), 7.26 (d, 1H, J=7.5 Hz), 7.34 (t, 1H, J=8.1 Hz), 7.40-7.52 (m, 4H), 8.27 (d, 1H, J=8.1 Hz), 10.72 (bs, 1H)

Preparation Example 26

Synthesis of A-c-08 (N-(4-fluorophenylaminocarbonyl)-2-oxyindole)

A-c-08 (N-(4-fluorophenylaminocarbonyl)-2-oxyindole) expressed by Structural Formula (99) was obtained in the same manner as in Preparation Example 19 except that phenyl isocyanate in Preparation Example 19 was changed to 4-fluorophenyl isocyanate (commercially available product).

Structural Formula (99)

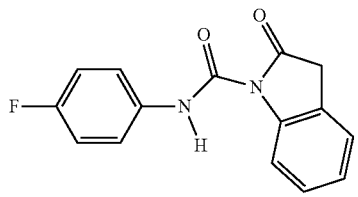

A-c-08 (N-(4-fluorophenylaminocarbonyl)-2-oxyindole)

1H NMR (300 Hz) 3.75 (s, 2H), 6.90-7.10 (m, 2H), 7.17 (dd, 1H, J=0.9, 7.5 Hz), 7.23 (d, 1H, J=7.5 Hz), 7.32 (t, 1H, J=8.1 Hz), 7.48-7.56 (m, 2H), 8.26 (d, 1H, 8.1 Hz), 10.62 (bs, 1H)

Preparation Example 27

Synthesis of A-c-09 (N-(4-methoxyphenylaminocarbonyl)-5-fluoro-2-oxyindole)

A-c-09 (N-(4-methoxyphenylaminocarbonyl)-5-fluoro-2-oxyindole) expressed by Structural Formula (100) was obtained in the same manner as in Preparation Example 19 except that oxyindole and phenyl isocyanate in Preparation Example 19 were changed to 5-fluoro-2-oxyindole (commercially available product) and 4-methoxyphenyl isocyanate (commercially available product), respectively.

Structural Formula (100)

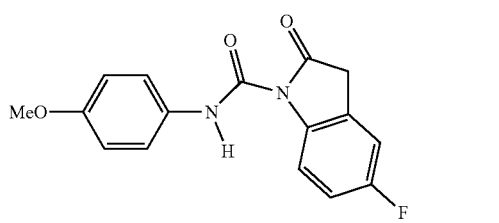

A-c-09 (N-(4-methoxyphenylaminocarbonyl)-5-fluoro-2-oxyindole)

1H NMR (300 Hz) 3.75 (s, 2H), 3.79 (s, 3H), 6.87 (dt, 2H, J (doublet)=9.0 Hz), 6.95-7.04 (m, 3H), 7.44 (dt, 2H, J (doublet)=9.0 Hz), 8.29 (dd, 1H, J=4.8, 8.8 Hz), 10.41 (bs, 1H)

Preparation Example 28

Synthesis of A-c-10 (N-(4-methoxyphenylaminocarbonyl)-2-oxyindole)

A-c-10 (N-(4-methoxyphenylaminocarbonyl)-2-oxyindole) expressed by Structural Formula (101) was obtained in the same manner as in Preparation Example 19 except that phenyl isocyanate in Preparation Example 19 was changed to 4-methoxyphenyl isocyanate (commercially available product).

Structural Formula (101)

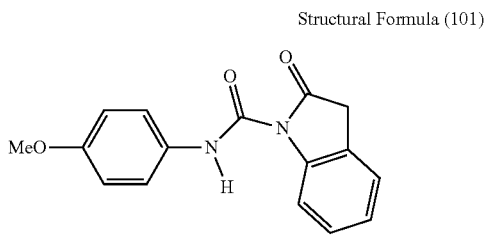 [SMILES: COc1ccc(NC(=O)N2C(=O)Cc3ccccc32)cc1]

A-c-10
(N-(4-methoxyphenylaminocarbonyl)-2-oxyindole)

1H NMR (300 Hz) 3.75 (s, 2H), 3.79 (s, 3H), 6.89 (dt, 2H, J (doublet)=9.0 Hz), 7.21-7.38 (m, 3H), 7.44 (dt, 2H, J (doublet)=9.0 Hz), 8.28 (d, 1H, J=8.4 Hz), 10.50 (bs, 1H)

Preparation Example 29

Synthesis of A-c-11 (N-(4-trifluoromethoxyphenylaminocarbonyl)-2-oxyindole)

A-c-11 (N-(4-trifluoromethoxyphenylaminocarbonyl)-2-oxyindole) expressed by Structural Formula (102) was obtained in the same manner as in Preparation Example 19 except that phenyl isocyanate in Preparation Example 19 was changed to 4-trifluoromethoxyphenyl isocyanate (commercially available product).

Structural Formula (102)

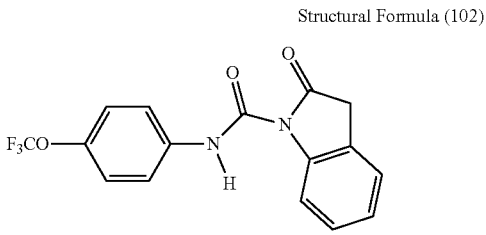 [SMILES: O=C1Cc2ccccc2N1C(=O)Nc1ccc(OC(F)(F)F)cc1]

A-c-11 (N-(4-trifluoromethoxyphenylaminocarbonyl)-2-oxyindole)

1H NMR (300 Hz) 3.81 (s, 2H), 7.15-7.42 (m, 5H), 7.62 (dt, 2H, J (doublet)=8.8 Hz), 8.30 (d, 1H, J=8.1 Hz), 10.78 (bs, 1H)

Preparation Example 30

Synthesis of A-c-12 (N-(2-trifluoromethylphenylaminocarbonyl)-2-oxyindole)

A-c-12 (N-(2-trifluoromethylphenylaminocarbonyl)-2-oxyindole) expressed by Structural Formula (103) was obtained in the same manner as in Preparation Example 19 except that phenyl isocyanate in Preparation Example 19 was changed to 2-trifluoromethylphenyl isocyanate (commercially available product).

Structural Formula (103)

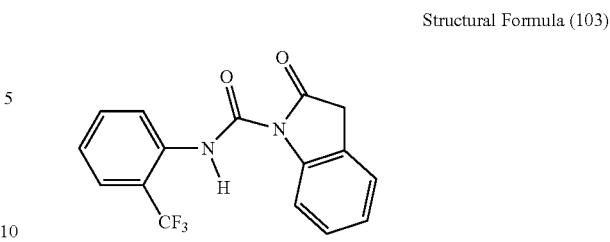

A-c-12 (N-(2-trifluoromethylphenylaminocarbonyl)-2-oxyindole)

1H NMR (300 Hz) 3.83 (s, 2H), 7.18-7.40 (m, 4H), 7.60 (t, 1H, J=7.8 Hz), 7.63 (d, 1H, J=7.8 Hz), 8.20 (d, 1H, J=8.4 Hz), 8.30 (d, 1H, J=8.4 Hz), 11.0 (s, 1H)
13C NMR (75 Hz) 36.9, 116.6, 112.9, 122.9, 124.0, 124.8, 124.9, 125.1, 126.1, 126.2, 128.4, 132.6, 134.5, 141.3, 149.8, 177.7

Example 1

Synthesis of A013
(N-acetyl-3-decyloxyacetyloxyindole)

N-acetyloxyindole (A-b-01) (100 mg, 0.57 mmol), decyloxyacetic acid (D-a-01) (123 mg, 0.57 mmol, 1.0 equiv.), and 4-(dimethylamino)pyridine (commercially available product, 105 mg, 0.85 mmol, 1.5 equiv.) were dissolved in dichloromethane (4 mL), and N-[3-(dimethylamino)]propyl-N'-ethylcarbodiimide hydrochloride (commercially available product, 165 mg, 0.85 mmol, 1.5 equiv.) serving as a condensation agent was added to the resultant solution at room temperature.

After the resultant mixture had been stirred at room temperature for 12 hours, a 5% by weight aqueous citric acid solution (10 mL) was added to the mixture, which was extracted with ethyl acetate (20 mL).

The obtained organic layer was separated and dried over sodium sulfate anhydrate. The solution was concentrated and then purified through silica gel column chromatography using an ethyl acetate-hexane solvent mixture, to thereby obtain A013 (N-acetyl-3-decyloxyacetyl-2-oxyindole) (160 mg, 76%).

Example 2

Synthesis of B003
(6-chloro-3-decanoyl-4-hydroxycoumarin)

6-Chloro-4-hydroxycoumarin (commercially available product, 100 mg, 0.51 mmol) and 4-(dimethylamino)pyridine (commercially available product, 93 mg, 0.76 mmol, 1.5 equiv.) were dissolved in dichloromethane (4 mL), and decanoic acid chloride (0.12 mL, 0.56 mmol, 1.1 equiv.) was added to the resultant solution at room temperature.

After the resultant mixture had been stirred at room temperature for 12 hours, a 5% by weight aqueous citric acid solution (10 mL) was added to the mixture, which was extracted with ethyl acetate (20 mL).

The obtained organic layer was separated and dried over sodium sulfate anhydrate. The solution was concentrated and then purified through silica gel column chromatography using an ethyl acetate-hexane solvent mixture, to thereby obtain B003 (6-chloro-3-decanoyl-4-hydroxycoumarin) (134 mg, 71%).

Example 3

Synthesis of A033 (N-(phenylaminocarbonyl)-5-bromo-3-decanoyl-2-oxyindole)

A-c-03 (N-(phenylaminocarbonyl)-5-bromo-2-oxyindole) (100 mg, 0.30 mmol) and 4-(dimethylamino)pyridine (commercially available product, 55 mg, 0.45 mmol, 1.5 equiv.) were dissolved in dichloromethane (4 mL), and decanoic anhydride (108 mg, 0.33 mmol, 1.1 equiv.) was added to the resultant solution at room temperature.

After the resultant mixture had been stirred at room temperature for 12 hours, a 5% by weight aqueous citric acid solution (10 mL) was added to the mixture, which was extracted with ethyl acetate (20 mL).

The obtained organic layer was separated and dried over sodium sulfate anhydrate. The solution was concentrated and then purified through silica gel column chromatography using an ethyl acetate-hexane solvent mixture, to thereby obtain A033 (N-(phenylaminocarbonyl)-5-bromo-3-decanoyl-2-oxyindole) (127 mg, 87%).

Example 4

Synthesis of B020 (4-hydroxy-3-(octylaminocarbonyl)coumarin)

4-Hydroxycoumarin (commercially available product, 103 mg, 0.64 mmol) and 4-(dimethylamino)pyridine (commercially available product, 94 mg, 0.77 mmol, 1.2 equiv.) were dissolved in dichloromethane (4 mL), and octyl isocyanate (commercially available product, 120 mg, 0.77 mmol, 1.2 equiv.) was added to the resultant mixture at room temperature.

After the resultant mixture had been stirred at room temperature for 12 hours, a 5% by weight aqueous citric acid solution (10 mL) was added to the mixture, which was extracted with ethyl acetate (20 mL).

The obtained organic layer was separated and dried over sodium sulfate anhydrate. The solution was concentrated and then purified through silica gel column chromatography using an ethyl acetate-hexane solvent mixture, to thereby obtain B020 (4-hydroxy-3-(octylaminocarbonyl)coumarin) (165 mg, 82%) as a white solid.

Example 5

Synthesis of A001

A001 was obtained in the same manner as in Example 3 except that A-c-03 in Example 3 was changed to commercially available 2-oxyindole.

Example 6

Synthesis of A002

A002 was obtained in the same manner as in Example 3 except that A-c-03 in Example 3 was changed to commercially available 6-chloro-2-oxyindole.

Example 7

Synthesis of A003

A003 was obtained in the same manner as in Example 3 except that A-c-03 in Example 3 was changed to A-d-02 (N-Boc-6-chloro-2-oxyindole).

Example 8

Synthesis of A004

A004 was obtained in the same manner as in Example 3 except that A-c-03 in Example 3 was changed to commercially available 5-fluoro-2-oxyindole.

Example 9

Synthesis of A005

A005 was obtained in the same manner as in Example 3 except that A-c-03 in Example 3 was changed to A-b-06 (N-decanoyl-2-oxyindole).

Example 10

Synthesis of A007

A007 was obtained in the same manner as in Example 3 except that A-c-03 in Example 3 was changed to commercially available N-methyl-2-oxyindole.

Example 11

Synthesis of A008

A008 was obtained in the same manner as in Example 1 except that A-b-01 and D-a-01 in Example 1 were changed to A-d-01 (N-Boc-2-oxyindole) and commercially available 4-butylcyclohexanecarboxylic acid, respectively.

Example 12

Synthesis of A009

A009 was obtained in the same manner as in Example 1 except that A-b-01 and D-a-01 in Example 1 were changed to A-d-02 (N-Boc-6-chloro-2-oxyindole) and commercially available 4-butylcyclohexanecarboxylic acid, respectively.

Example 13

Synthesis of A010

A010 was obtained in the same manner as in Example 1 except that D-a-01 in Example 1 was changed to commercially available 4-butylcyclohexanecarboxylic acid.

Example 14

Synthesis of A011

A011 was obtained in the same manner as in Example 1 except that A-b-01 and D-a-01 in Example 1 were changed to A-d-01 (N-Boc-2-oxyindole) and D-c-01 (N-decanoylglycine), respectively.

Example 15

Synthesis of A012

A012 was obtained in the same manner as in Example 1 except that A-b-01 in Example 1 was changed to A-d-02 (N-Boc-6-chloro-2-oxyindole).

Example 16

Synthesis of A014

A014 was obtained in the same manner as in Example 1 except that A-b-01 and D-a-01 in Example 1 were changed to A-b-05 (N-benzoyl-2-oxyindole) and commercially available 4-butylcyclohexanecarboxylic acid, respectively.

Example 17

Synthesis of A015

A015 was obtained in the same manner as in Example 1 except that A-b-01 and D-a-01 in Example 1 were changed to A-c-06 (N-(butylaminocarbonyl)-2-oxyindole) and commercially available 4-butylcyclohexanecarboxylic acid, respectively.

Example 18

Synthesis of A016

A016 was obtained in the same manner as in Example 1 except that A-b-01 and D-a-01 in Example 1 were changed to A-c-01 (N-(phenylaminocarbonyl)-2-oxyindole) and commercially available 4-butylcyclohexanecarboxylic acid, respectively.

Example 19

Synthesis of A017

A017 was obtained in the same manner as in Example 1 except that A-b-01 in Example 1 was changed to A-b-02 (N-acetyl-6-chloro-2-oxyindole).

Example 20

Synthesis of A018

A018 was obtained in the same manner as in Example 1 except that D-a-01 in Example 1 was changed to D-a-03 (decyloxypropionic acid).

Example 21

Synthesis of A019

A019 was obtained in the same manner as in Example 1 except that A-b-01 in Example 1 was changed to N-(phenylaminocarbonyl)-2-oxyindole (A-c-01).

Example 22

Synthesis of A020

A020 was obtained in the same manner as in Example 1 except that A-b-01 and D-a-01 in Example 1 were changed to A-c-06 (N-(butylaminocarbonyl)-2-oxyindole) and D-a-03 (decyloxypropionic acid), respectively.

Example 23

Synthesis of A021

A021 was obtained in the same manner as in Example 3 except that A-c-03 and decanoic anhydride in Example 1 were changed to A-c-01 (N-(phenylaminocarbonyl)-2-oxyindole) and D-a-03 (decyloxypropionic acid), respectively.

Example 24

Synthesis of A022

A022 was obtained in the same manner as in Example 1 except that A-b-01 and D-a-01 in Example 1 were changed to A-b-06 (N-decanoyl-2-oxyindole) and acetic anhydride, respectively.

Example 25

Synthesis of A023

A023 was obtained in the same manner as in Example 1 except that A-b-01 in Example 1 was changed to A-b-03 (N-acetyl-5-fluoro-2-oxyindole).

Example 26

Synthesis of A024

A024 was obtained in the same manner as in Example 1 except that D-a-01 in Example 1 was changed to commercially available 10-bromodecanoic acid.

Example 27

Synthesis of A025

A025 was obtained in the same manner as in Example 1 except that A-b-01 and D-a-01 in Example 1 were changed of A-c-01 (N-(phenylaminocarbonyl)-2-oxyindole) and commercially available 10-bromodecanoic acid, respectively.

Example 28

Synthesis of A026

A026 was obtained in the same manner as in Example 3 except that A-c-03 in Example 3 was changed to A-b-04 (N-acetyl-5-bromo-2-oxyindole).

Example 29

Synthesis of A027

A027 was obtained in the same manner as in Example 1 except that A-b-01 and D-a-01 in Example 1 were changed to A-d-03 (N-Boc-5-fluoro-2-oxyindole) and commercially available 4-butylcyclohexanecarboxylic acid, respectively.

Example 30

Synthesis of A029

A029 was obtained in the same manner as in Example 1 except that A-b-01 in Example 1 was changed to A-b-04 (N-acetyl-5-bromo-2-oxyindole).

Example 31

Synthesis of A030

A030 was obtained in the same manner as in Example 1 except that A-b-01 and D-a-01 in Example 1 were changed to A-b-04 (N-acetyl-5-bromo-2-oxyindole) and D-b-01 (decylthioacetic acid), respectively.

Example 32

Synthesis of A031

A031 was obtained in the same manner as in Example 2 except that 6-chloro-4-hydroxycoumarin and decanoic acid chloride in Example 2 were changed to A-c-05 (N-(octylaminocarbonyl)-2-oxyindole) and commercially available benzoyl chloride, respectively.

Example 33

Synthesis of A034

A034 was obtained in the same manner as in Example 1 except that A-b-01 and D-a-01 in Example 1 were changed to A-c-03 (N-(phenylaminocarbonyl)-5-bromo-2-oxyindole) and commercially available 4-butylcyclohexanecarboxylic acid, respectively.

Example 34

Synthesis of A035

A035 was obtained in the same manner as in Example 1 except that A-b-01 in Example 1 was changed to A-c-03 (N-(phenylaminocarbonyl)-5-bromo-2-oxyindole).

Example 35

Synthesis of A036

A036 was obtained in the same manner as in Example 1 except that A-b-01 in Example 1 was changed to N-(phenylaminocarbonyl)-5-fluoro-2-oxyindole (A-c-04).

Example 36

Synthesis of A037

A037 was obtained in the same manner as in Example 1 except that A-b-01 and D-a-01 in Example 1 were changed to A-c-04 (N-(phenylaminocarbonyl)-5-fluoro-2-oxyindole) and D-b-01 (decylthioacetic acid), respectively.

Example 37

Synthesis of A038

A038 was obtained in the same manner as in Example 1 except that A-b-01 in Example 1 was changed to A-c-07 (N-(4-bromophenylaminocarbonyl)-2-oxyindole).

Example 38

Synthesis of A039

A039 was obtained in the same manner as in Example 3 except that A-c-03 in Example 3 was changed to A-c-07 (N-(4-bromophenylaminocarbonyl)-2-oxyindole).

Example 39

Synthesis of A040

A040 was obtained in the same manner as in Example 1 except that A-b-01 and D-a-01 in Example 1 were changed to A-c-07 (N-(4-bromophenylaminocarbonyl)-2-oxyindole) and commercially available 4-butylcyclohexanecarboxylic acid, respectively.

Example 40

Synthesis of A041

A041 was obtained in the same manner as in Example 1 except that A-b-01 in Example 1 was changed to N-(4-fluorophenylaminocarbonyl)-2-oxyindole (A-c-08).

Example 41

Synthesis of A042

A042 was obtained in the same manner as in Example 3 except that A-c-03 in Example 3 was changed to A-c-08 (N-(4-fluorophenylaminocarbonyl)-2-oxyindole).

Example 42

Synthesis of A043

A043 was obtained in the same manner as in Example 1 except that A-b-01 and D-a-01 in Example 1 were changed to A-c-08 (N-(4-fluorophenylaminocarbonyl)-2-oxyindole) and commercially available 4-butylcyclohexanecarboxylic acid, respectively.

Example 43

Synthesis of A044

A044 was obtained in the same manner as in Example 3 except that A-c-03 in Example 3 was changed to N-(phenylaminocarbonyl)-5-fluoro-2-oxyindole (A-c-04).

Example 44

Synthesis of A045

A045 was obtained in the same manner as in Example 1 except that A-b-01 in Example 1 was changed to A-c-10 (N-(4-methoxyphenylaminocarbonyl)-2-oxyindole).

Example 45

Synthesis of A046

A046 was obtained in the same manner as in Example 3 except that A-c-03 in Example 3 was changed to A-c-10 (N-(4-methoxyphenylaminocarbonyl)-2-oxyindole).

Example 46

Synthesis of A047

A047 was obtained in the same manner as in Example 1 except that A-b-01 in Example 1 was changed to A-c-09 (N-(4-methoxyphenylaminocarbonyl)-5-fluoro-2-oxyindole).

Example 47

Synthesis of A048

A048 was obtained in the same manner as in Example 3 except that A-c-03 in Example 3 was changed to A-c-09 (N-(4-methoxyphenylaminocarbonyl)-5-fluoro-2-oxyindole).

Example 48

Synthesis of A049

A049 was obtained in the same manner as in Example 1 except that A-b-01 and D-a-01 in Example 1 were changed to N-decanoyl-2-oxyindole (A-b-06) and commercially available methoxyacetic acid, respectively.

Example 49

Synthesis of A050

A050 was obtained in the same manner as in Example 1 except that A-b-01 and D-a-01 in Example 1 were changed to A-b-07 (N-decanoyl-5-fluoro-2-oxyindole) and commercially available methoxyacetic acid, respectively.

Example 50

Synthesis of A051

A051 was obtained in the same manner as in Example 3 except that A-c-03 and decanoic anhydride in Example 3 were changed to A-b-07 (N-decanoyl-5-fluoro-2-oxyindole) and acetic anhydride, respectively.

Example 51

Synthesis of A052

A052 was obtained in the same manner as in Example 3 except that A-c-03 and decanoic anhydride in Example 3 were changed to A-b-07 (N-decanoyl-5-fluoro-2-oxyindole) and benzoic anhydride, respectively.

Example 52

Synthesis of A053

A053 was obtained in the same manner as in Example 1 except that A-b-01 and D-a-01 in Example 1 were changed to A-c-11 (N-(4-trifluoromethoxyphenylaminocarbonyl)-2-oxyindole) and commercially available decanoic acid, respectively.

Example 53

Synthesis of A054

A054 was obtained in the same manner as in Example 1 except that A-b-01 and D-a-01 in Example 1 were changed to A-c-12 (N-(2-trifluoromethylphenylaminocarbonyl)-2-oxyindole) and commercially available decanoic acid, respectively.

Example 54

Synthesis of A055

A055 was obtained in the same manner as in Example 1 except that A-b-01 in Example 1 was changed to A-d-03 (N-Boc-5-fluoro-2-oxyindole).

Example 55

Synthesis of A056

A056 was obtained in the same manner as in Example 1 except that A-b-01 in Example 1 was changed to A-d-02 (N-Boc-6-chloro-2-oxyindole).

Example 56

Synthesis of A057

A057 was obtained in the same manner as in Example 1 except that D-a-01 in Example 1 was changed to D-a-05 (octyloxyacetic acid).

Example 57

Synthesis of A058

A058 was obtained in the same manner as in Example 1 except that A-b-01 and D-a-01 in Example 1 were changed to A-c-01 (N-(phenylaminocarbonyl)-2-oxyindole) and D-a-05 (octyloxyacetic acid), respectively.

Example 58

Synthesis of A059

A059 was obtained in the same manner as in Example 1 except that A-b-01 and D-a-01 in Example 1 were changed to A-c-04 (N-(phenylaminocarbonyl)-5-fluoro-2-oxyindole) and commercially available nonanoic acid, respectively.

Example 59

Synthesis of A060

A060 was obtained in the same manner as in Example 1 except that A-b-01 and D-a-01 in Example 1 were changed to A-b-06 (N-decanoyl-2-oxyindole) and commercially available 4-chlorobenzoic acid, respectively.

Example 60

Synthesis of A061

A061 was obtained in the same manner as in Example 1 except that A-b-01 and D-a-01 in Example 1 were changed to A-b-06 (N-decanoyl-2-oxyindole) and commercially available 4-fluorobenzoic acid, respectively.

Example 61

Synthesis of A062

A062 was obtained in the same manner as in Example 1 except that A-b-01 and D-a-01 in Example 1 were changed to A-b-06 (N-decanoyl-2-oxyindole) and commercially available 4-methoxybenzoic acid, respectively.

Example 62

Synthesis of A063

A063 was obtained in the same manner as in Example 1 except that A-b-01 and D-a-01 in Example 1 were changed to A-b-06 (N-decanoyl-2-oxyindole) and commercially available 2-acetoxybenzoic acid.

Example 63

Synthesis of B001

B001 was obtained in the same manner as in Example 2 except that 6-chloro-4-hydroxycoumarin in Example 2 was changed to commercially available 7-methoxy-4-hydroxycoumarin.

Example 64

Synthesis of B004

B004 was obtained in the same manner as in Example 2 except that 6-chloro-4-hydroxycoumarin in Example 2 was changed to commercially available 6-fluoro-4-hydroxycoumarin.

Example 65

Synthesis of B006

B006 was obtained in the same manner as in Example 1 except that A-b-01 and D-a-01 in Example 1 were changed to commercially available 4-hydroxycoumarin and commercially available menthoxy acetic acid, respectively.

Example 66

Synthesis of B009

B009 was obtained in the same manner as in Example 1 except that A-b-01 and D-a-01 in Example 1 were changed to commercially available 6-fluoro-4-hydroxycoumarin and commercially available 4-butylcyclohexanecarboxylic acid, respectively.

Example 67

Synthesis of B011

B011 was obtained in the same manner as in Example 1 except that A-b-01 and D-a-01 in Example 1 were changed to commercially available 4-hydroxycoumarin and D-c-02 (N-decanoylalanine), respectively.

Example 68

Synthesis of B012

B012 was obtained in the same manner as in Example 2 except that 6-chloro-4-hydroxycoumarin in Example 2 was changed to commercially available 6-methyl-4-hydroxycoumarin.

Example 69

Synthesis of B013

B013 was obtained in the same manner as in Example 1 except that A-b-01 and D-a-01 in Example 1 were changed to commercially available 4-hydroxycoumarin and commercially available N-benzoylglycine, respectively.

Example 70

Synthesis of B015

B015 was obtained in the same manner as in Example 1 except that A-b-01 in Example 1 was changed to commercially available 4-hydroxycoumarin.

Example 71

Synthesis of B016

B016 was obtained in the same manner as in Example 1 except that A-b-01 and D-a-01 in Example 1 were changed to commercially available 4-hydroxycoumarin and D-c-01 (N-decanoylglycine), respectively.

Example 72

Synthesis of B017

B017 was obtained in the same manner as in Example 1 except that A-b-01 and D-a-01 in Example 1 were changed to commercially available 4-hydroxycoumarin and D-a-03 (decyloxypropionic acid), respectively.

Example 73

Synthesis of B019

B019 was obtained in the same manner as in Example 1 except that A-b-01 in Example 1 was changed to commercially available 6-fluoro-4-hydroxycoumarin.

Example 74

Synthesis of B021

B021 was obtained in the same manner as in Example 1 except that A-b-01 and D-a-01 in Example 1 were changed to commercially available 4-hydroxycoumarin and D-a-02 (pentyloxyacetic acid).

Example 75

Synthesis of B022

B022 was obtained in the same manner as in Example 4 except that 4-hydroxycoumarin in Example 4 was changed to commercially available 6-fluoro-4-hydroxycoumarin.

Example 76

Synthesis of B023

B023 was obtained in the same manner as in Example 1 except that A-b-01 and D-a-01 in Example 1 were changed to commercially available 4-hydroxycoumarin and D-b-01 (decylthioacetic acid), respectively.

Example 77

Synthesis of B024

B024 was obtained in the same manner as in Example 1 except that A-b-01 and D-a-01 in Example 1 were changed to commercially available 4-hydroxycoumarin and D-a-04 (4-butylphenylmethoxyacetic acid).

Example 78

Synthesis of B025

B025 was obtained in the same manner as in Example 4 except that octyl isonyanate in Example 4 was changed to commercially available dodecyl isonyanate.

Example 79

Synthesis of B026

B026 was synthesized by allowing B023 to react with m-chloroperbenzoic acid in dichloromethane.

Example 80

Synthesis of B027

B027 was obtained in the same manner as in Example 1 except that A-b-01 and D-a-01 in Example 1 were changed to commercially available 6-fluoro-4-hydroxycoumarin and D-b-01 (decylthioacetic acid), respectively.

Example 81

Synthesis of B028

B028 was obtained in the same manner as in Example 1 except that A-b-01 in Example 1 was changed to commercially available 6-chloro-4-hydroxycoumarin.

Example 82

Synthesis of B029

B029 was obtained in the same manner as in Example 1 except that A-b-01 in Example 1 was changed of commercially available 6-methyl-4-hydroxycoumarin.

Example 83

Synthesis of B030

B030 was obtained in the same manner as in Example 1 except that A-b-01 and D-a-01 in Example 1 were changed to commercially available 4-hydroxycoumarin and D-a-05 (octyloxyacetic acid), respectively.

Test Example 1

Measurement of MIC for *Staphylococcus aureus* and *Escherichia coli*

Each of the compounds obtained in Examples 1 to 84 was measured for minimum inhibitory concentration (MIC) for *Staphylococcus aureus* and *Escherichia coli*.

Bacterial cells of *Staphylococcus aureus* Smith strain, *Staphylococcus aureus* 209P strain, *Staphylococcus aureus* MRSA No. 17 (methicillin-resistant *Staphylococcus aureus*: MRSA), *Escherichia coli* K-12 strain, and *Escherichia coli* BE1121 strain were respectively cultured with shaking at 37° C. overnight in a regular bouillon medium (polypeptone (product of NIHON PHARMACEUTICAL CO., LTD.) 1% by weight, fish extract for bacteria (product of KYOKUTO PHARMACEUTICAL INDUSTRIAL CO., LTD.) 1% by weight, and sodium chloride 0.2% by weight). After completion of the culturing, the cultures were diluted with the regular bouillon medium so that the concentration of the bacterial cells was $2 \times 10^4$ CFU/mL to $9 \times 10^4$ CFU/mL.

Test samples were prepared to have a concentration of 256 mg/L with the regular bouillon medium. From this concentration, each of the test samples was 2-fold diluted in 11 steps to 0.125 mg/L.

Each of the above-diluted bacterial cultures was added at 50 μL/well to the wells each containing 50 μL of the regular bouillon media containing the test samples at the above series of concentrations, followed by static culturing at 37° C. overnight.

After completion of the culturing, whether the bacteria grew was visually determined based on turbidity to calculate MIC for each bacterial strain. Results are presented in Tables 1 to 3.

Test Example 2

Measurement of MIC for *Enterococcus*

Each of the compounds obtained in Examples 1 to 84 was measured for minimum inhibitory concentration (MIC) for *Enterococcus*.

Bacterial cells of *Enterococcus faecalis* 5038 strain and *Enterococcus faecalis* NCTC12201 strain (vancomycin-resistant *Enterococcus*: VRE) were respectively cultured with shaking at 37° C. overnight in a Heart Infusion Broth medium (product of Becton, Dickinson and Company). After completion of the culturing, the cultures were diluted with the Heart Infusion Broth medium so that the concentration of the bacterial cells was $2 \times 10^4$ CFU/mL to $9 \times 10^4$ CFU/mL.

Test samples were prepared to have a concentration of 256 mg/L with the Heart Infusion Broth medium. From this concentration, each of the test samples was 2-fold diluted in 11 steps to 0.125 mg/L.

Each of the above-diluted bacterial cultures was added at 50 μL/well to the wells each containing 50 μL of the Heart Infusion Broth media containing the test samples at the above series of concentrations, followed by static culturing at 37° C. overnight.

After completion of the culturing, whether the bacteria grew was visually determined based on turbidity to calculate MIC for each bacterial strain. Results are presented in Tables 1 to 3.

Test Example 3

Measurement of MIC for *Clostridium difficile* and *perfringens*

Each of the compounds obtained in Examples 1 to 84 was measured for minimum inhibitory concentration (MIC) for *Clostridium difficile* and *perfringens*.

Under 10% $CO_2$-containing anaerobic culturing conditions, bacterial cells of *Clostridium difficile* JCM1296 strain and *Clostridium perfringens* PB6K strain were respectively statically cultured at 37° C. for 48 hours in a CD medium (proteose peptone (Becton, Becton, Dickinson and Company) 4% by weight, disodium hydrogenphosphate 0.5% by weight, potassium dihydrogenphosphate 0.1% by weight, magnesium sulfate 0.01% by weight, sodium chloride 0.2% by weight, and fructose 0.6% by weight, pH 7.4). After completion of the culturing, the cultures were suspended in and diluted with the CD medium so that the concentration of the bacterial cells was $2 \times 10^4$ CFU/mL to $9 \times 10^4$ CFU/mL.

Test samples were prepared to have a concentration of 256 mg/L with the CD medium. From this concentration, each of the test samples was 2-fold diluted in 11 steps to 0.125 mg/L.

Each of the above-diluted bacterial cultures was added at 50 μL/well to the wells each containing 50 μL of the CD media containing the test samples at the above series of concentrations, followed by static culturing at 37° C. overnight under 10% $CO_2$-containing anaerobic culturing conditions.

After completion of the culturing, whether the bacteria grew was visually determined based on turbidity to calculate MIC for each bacterial strain. Results are presented in Tables 1 to 3.

TABLE 1

| | MIC (μg/mL) | | | | | | | |
|---|---|---|---|---|---|---|---|---|
| | Kind of bacteria | | | | | | | |
| | *Straphyrococcus aureus* | | | *Enterococcus faecalis* | | *Clostridium difficile* | *Clostridium perfringens* | *Escherichia coli* | |
| | Strain | | | | | | | | |
| Compd. | Smith | 209P | MRSA No. 17 (MRSA) | 5038 | NCTC 12201 (VRE) | JCM1296 | PB6K | K12 | BE1121 |
| A001 | 32 | 16 | 32 | 16 | 16 | N.D. | N.D. | 256 | 256 |
| A002 | 16 | 16 | 16 | 16 | 15 | 32 | 32 | 128 | 128 |
| A003 | 256 | 256 | 256 | 128 | 128 | 0.5 | 1 | 256 | 128 |
| A004 | 16 | 16 | 32 | 16 | 15 | 2 | 8 | 128 | 128 |
| A005 | 64 | 32 | 32 | 32 | 32 | 2 | 16 | 128 | 128 |
| A007 | 8 | 32 | 128 | 32 | 15 | 2 | 8 | 256 | 256 |
| A008 | 128 | 64 | 256 | 128 | 128 | 1 | 2 | 128 | 128 |
| A009 | 32 | 128 | 256 | 4 | 4 | 0.5 | 1 | 128 | 128 |
| A010 | 0.5 | 2 | 1 | 0.5 | 0.5 | 0.25 | 1 | 256 | 256 |
| A011 | 128 | 256 | 256 | 256 | 256 | 2 | 2 | 128 | 128 |
| A012 | 256 | 256 | 256 | 256 | 256 | 32 | 32 | 256 | 256 |
| A013 | 256 | 256 | 256 | 64 | 32 | 0.25 | 0.5 | 256 | 256 |
| A014 | 1 | 2 | 4 | 1 | 0.5 | 4 | 8 | 128 | 128 |
| A015 | 256 | 256 | 256 | 8 | 8 | 4 | 8 | 256 | 256 |
| A016 | 4 | 128 | 256 | 1 | 0.5 | 0.25 | 4 | 256 | 256 |
| A017 | <0.125 | 128 | 16 | <0.125 | <0.125 | <0.125 | <0.125 | 128 | 128 |
| A018 | 0.5 | 64 | 8 | 0.5 | 0.5 | 256 | 256 | 256 | <0.125 |
| A019 | 4 | 256 | 256 | 1 | 4 | 0.5 | 2 | 256 | 128 |
| A020 | 1 | 256 | 256 | 0.5 | 1 | 0.5 | 4 | 256 | 256 |
| A021 | 0.5 | 128 | 256 | 0.5 | 0.5 | 1 | 2 | 256 | 256 |
| A022 | 2 | 8 | 4 | 1 | 1 | 0.25 | 4 | 128 | 16 |
| A023 | 1 | 128 | 64 | 0.25 | 0.25 | <0.125 | <0.125 | 128 | 128 |
| A024 | 4 | 16 | 16 | 0.5 | 1 | 0.5 | 0,5 | 128 | 16 |
| A025 | 2 | 256 | 256 | 0.5 | 0.5 | 0.5 | 1 | 256 | 256 |
| A026 | 0.25 | 4 | 4 | <0.125 | <0.125 | <0.125 | 0.25 | 128 | 8 |
| A027 | 16 | 128 | 128 | 8 | 8 | 1 | 2 | 128 | 128 |
| A029 | 0.5 | 128 | 128 | 0.25 | <0.125 | <0.125 | <0.125 | 128 | 128 |
| A030 | 0.25 | 2 | 2 | 0.25 | 0.25 | <0.125 | <0.125 | 256 | 8 |

N.D.: Not determined

TABLE 2

MIC (μg/mL)

| | Kind of bacteria | | | | | | | |
|---|---|---|---|---|---|---|---|---|
| | Straphyrococcus aureus | | | Enterococcus faecalis | | Clostridium difficile | Clostridium perfringens | Escherichia coli | |
| | Strain | | | | | | | | |
| Compd. | Smith | 209P | MRSA No. 17 (MRSA) | 5038 | NCTC 12201 (VRE) | JCM1296 | PB6K | K12 | BE1121 |
|---|---|---|---|---|---|---|---|---|---|
| A031 | 0.5 | 0.25 | 256 | 025 | 0.25 | 0.25 | 0.25 | 256 | 256 |
| A033 | 256 | 256 | 256 | 256 | 256 | 0.5 | 0.5 | 256 | 128 |
| A034 | 1 | 32 | 64 | 1 | 1 | 0.5 | 0.5 | 128 | 128 |
| A035 | 8 | 64 | 64 | 4 | 2 | 0.5 | 0.25 | 128 | 128 |
| A036 | 0.25 | 128 | 128 | 0.5 | 0.5 | 0.25 | 0.25 | 128 | 128 |
| A037 | 0.25 | 2 | 2 | 0.5 | 0.5 | 0.5 | 1 | 256 | 256 |
| A038 | 64 | 64 | 64 | 8 | 16 | 32 | 16 | 128 | 128 |
| A039 | 256 | 256 | 256 | 256 | 256 | 64 | 64 | 256 | 256 |
| A040 | 2 | 128 | 128 | 1 | 1 | 8 | 4 | 256 | 256 |
| A041 | 4 | 256 | 256 | 2 | 4 | 0.5 | 8 | 128 | 256 |
| A042 | 0.5 | 256 | 256 | 2 | 4 | <0.125 | 1 | 256 | 256 |
| A043 | 1 | 256 | 128 | 1 | 1 | 1 | 4 | 256 | 256 |
| A044 | 0.25 | 256 | 256 | 1 | 0.5 | <0.125 | <0.125 | 256 | 256 |
| A045 | 128 | 256 | 256 | 4 | 64 | 0.5 | 8 | 128 | 128 |
| A046 | 256 | 256 | 256 | 256 | 256 | 1 | 8 | 256 | 256 |
| A047 | 8 | 128 | 128 | 4 | 16 | 1 | 0.25 | 128 | 128 |
| A048 | 256 | 256 | 256 | 128 | 256 | 32 | 256 | 256 | 256 |
| A049 | 1 | 256 | 256 | 0.5 | 0.5 | 0.5 | 0.5 | 256 | 128 |
| A050 | 0.5 | 256 | 256 | 0.5 | 0.5 | 0.25 | 0.5 | 256 | 128 |
| A051 | 0.5 | 4 | 4 | 0.5 | 0.25 | 1 | 8 | 56 | 2 |
| A052 | 0.5 | 64 | 64 | 0.25 | 0.5 | 0.5 | 0.5 | 256 | 128 |
| A053 | 256 | 256 | 256 | 128 | 128 | 16 | 32 | 128 | 128 |
| A054 | 0.5 | 2 | 2 | 1 | 1 | <0.125 | <0.125 | 256 | 256 |
| A055 | 128 | 128 | 128 | 128 | 128 | 0.25 | 2 | 256 | 256 |
| A056 | 256 | 256 | 256 | 256 | 256 | 4 | 0.5 | 256 | 256 |
| A057 | 1 | 8 | 16 | 1 | 2 | 0.25 | 0.5 | 128 | 128 |
| A058 | 0.5 | 64 | 128 | 0.25 | 0.25 | <0.125 | <0.125 | 128 | 128 |
| A059 | 0.5 | 64 | 64 | 0.5 | 025 | 8 | 4 | 128 | 256 |
| A060 | 1 | 64 | 16 | 1 | 1 | 0.5 | 1 | 128 | 128 |
| A061 | 2 | 128 | 64 | 4 | 4 | Z. | 2 | 128 | 128 |
| A062 | 2 | 128 | 16 | 2 | 2 | 4 | 8 | 256 | 256 |
| A063 | 256 | 256 | 256 | 256 | 256 | 16 | 256 | 128 | 128 |

TABLE 3

MIC (μg/mL)

| | Kind of bacteria | | | | | | | |
|---|---|---|---|---|---|---|---|---|
| | Straphyrococcus aureus | | | Enterococcus faecalis | | Clostridium difficile | Clostridium perfringens | Escherichia coli | |
| | Strain | | | | | | | | |
| Compd. | Smith | 209P | MRSA No. 17 (MRSA) | 5038 | NCTC 12201 (VRE) | JCM1296 | PB6K | K12 | BE1121 |
|---|---|---|---|---|---|---|---|---|---|
| B001 | 128 | 256 | 256 | 64 | 64 | 64 | 64 | 256 | 256 |
| B003 | 0.5 | 2 | 2 | 0.5 | 0.25 | N.D. | 0.25 | 256 | 256 |
| B004 | 0.25 | 1 | 1 | 0.5 | 0.25 | N.D. | 0.25 | 256 | 2 |
| B006 | 1 | 1 | 2 | 2 | 2 | 2 | 1 | 128 | 2 |
| B009 | 0.5 | 1 | 1 | 0.5 | 0.5 | 0.25 | 1 | 256 | 4 |
| B011 | 256 | 256 | 256 | 256 | 256 | 2 | 1 | 256 | 256 |
| B012 | 0.5 | 0.5 | 0.5 | 0.25 | 0.25 | 0.25 | 0.5 | 256 | 256 |
| B013 | 256 | 256 | 256 | 256 | 256 | 128 | 128 | 256 | 256 |
| B015 | 2 | 8 | 8 | 4 | 2 | 0.25 | 25 | 256 | 128 |
| B016 | 256 | 256 | 256 | 256 | 256 | 8 | 16 | 256 | 256 |
| B017 | 2 | 8 | 4 | 1 | 0.5 | <0.125 | 0.25 | 256 | 256 |
| B019 | 256 | 256 | 256 | 256 | 256 | <0.125 | <0.125 | 256 | 256 |
| B020 | 8 | 8 | 16 | 1 | 1 | 1 | 8 | 64 | 32 |
| B021 | 128 | 32 | 123 | 32 | 64 | 8 | 32 | 128 | 16 |
| B022 | 128 | 128 | 256 | 256 | 256 | 16 | 64 | 256 | 128 |
| B023 | 0.25 | 1 | 1 | 0.25 | 0.25 | <0.125 | <0.125 | 256 | 2 |

TABLE 3-continued

| | MIC (μg/mL) | | | | | | | | |
|---|---|---|---|---|---|---|---|---|---|
| | Kind of bacteria | | | | | | | | |
| | Straphyrococcus aureus | | | Enterococcus faecalis | | Clostridium difficile | Clostridium perfringens | Escherichia coli | |
| | Strain | | | | | | | | |
| Compd. | Smith | 209P | MRSA No. 17 (MRSA) | 5038 | NCTC 12201 (VRE) | JCM1296 | PB6K | K12 | BE1121 |
| B024 | 8 | 4 | 64 | 2 | 2 | 0.25 | 1 | 256 | 2 |
| B025 | 2 | 8 | 8 | 2 | 1 | 4 | 4 | 256 | 256 |
| B026 | 128 | 128 | 123 | 32 | 32 | 8 | 3 | 128 | 128 |
| B027 | 0.25 | 2 | 1 | 0.25 | <0.125 | <0.125 | 0.25 | 256 | 4 |
| B028 | 8 | 128 | 256 | 256 | 256 | 0.25 | 0.25 | 256 | 256 |
| B029 | 4 | 256 | 256 | 8 | 2 | <0.125 | <0.125 | 256 | 256 |
| B030 | 2 | 4 | 1 | 2 | 4 | 0.25 | 0.25 | 128 | 2 |

N.D.: Not determined

From the results in Tables 1 to 3, the compounds of the present invention belonging to the 3-acyloxyindole compounds or the 3-acyl-4-hydroxycoumarin compounds represented by any one of General Formulas (1) to (5) have antibacterial activity, and moreover many of them are found to have specific antibacterial activity against multidrug-resistant bacteria such as MRSA, VRE, *Clostridium difficile*.

Aspects of the present invention are, for example, as follows.

In one aspect, the present invention provides a compound represented by any one of General Formulas (1) to (3) below, a tautomer or geometric isomer thereof, or a salt thereof:

General Formula (1)

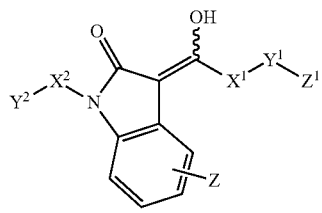

AI

General Formula (2)

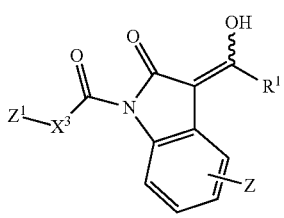

AII

General Formula (3)

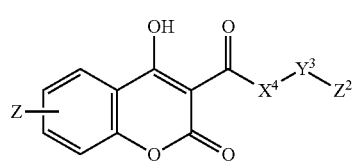

B where in the General Formulas (1) to (3),
$X^1$ represents a single bond or an alkylene group having 1 to 8 carbon atoms,
$Y^1$ represents a single bond, —O—, —NHCO—, —NHCOO—, —S—, —SO—, or —SO$_2$—,
$Z^1$ represents a cyclic, linear, or branched alkyl group which has 8 to 30 carbon atoms and may have a halogen atom,
$X^2$ represents a single bond, —CO—, —CONH—, or —COO—,
$Y^2$ represents a hydrocarbon group which has 1 to 30 carbon atoms and may have —CN, —NO$_2$, an alkoxy group, a halogen atom, or any combination thereof; or a hydrogen atom,
$Z^2$ represents a hydrocarbon group which has 5 to 30 carbon atoms and may have a halogen atom,
$X^3$ represents a single bond or —NH—,
$Y^3$ represents —O—, —NH—, —NHCO—, —NHCOO—, —S—, —SO—, or —SO$_2$—,
$X^4$ represents an alkylene group having 1 to 8 carbon atoms,
Z represents a hydrogen atom, a halogen atom, an alkoxy group having 1 to 6 carbon atoms, or a hydrocarbon group having 1 to 20 carbon atoms, and
$R^1$ represents a hydrocarbon group which has 1 to 30 carbon atoms and may have an alkoxy group, —OH, —CN, —NO$_2$, a halogen atom, or any combination thereof.

In one variant, the present invention provides the compound represented by any one of General Formulas (1) to (3), the tautomer or geometric isomer thereof, or the salt thereof according to the present invention, wherein $X^1$ and $X^4$ each are a methylene group, $X^2$ is —CO— or —CONH—, $X^3$ is a single bond, $Y^1$ and $Y^3$ each are —O—, $Y^2$ is a methyl group, or a phenyl group which may have, as a substituent, an alkoxy group, a trifluoromethyl group, a halogen atom, or any combination thereof, Z is a hydrogen atom or a halogen atom, and $Z^1$ and $Z^2$ each are a cyclic, linear, or branched alkyl group having 8 to 12 carbon atoms.

In one variant, the present invention provides the compound represented by any one of General Formulas (1) to (3), the tautomer or geometric isomer thereof, or the salt thereof according to the present invention, wherein $X^1$ and $X^4$ each are a methylene group, $X^2$ is —CO— or —CONH—, $X^3$ is a single bond, $Y^1$ and $Y^3$ each are —S—, $Y^2$ is a methyl group, or a phenyl group which may have, as a substituent, an alkoxy group, a trifluoromethyl group, a halogen atom, or any combination thereof, Z is a hydrogen atom or a halogen atom, and $Z^1$ and $Z^2$ each are a cyclic, linear, or branched alkyl group having 8 to 12 carbon atoms.

In one variant, the present invention provides the compound represented by any one of General Formulas (1) to (3), the tautomer or geometric isomer thereof, or the salt thereof according to the present invention, wherein $X^1$, $X^3$, and $Y^1$ each are a single bond, $X^2$ is —CO— or —CONH—, $X^4$ is a methylene group, $Y^3$ is —O— or —S—, $Y^2$ is a methyl group, or a phenyl group which may have, as a substituent, an alkoxy group, a trifluoromethyl group, a halogen atom, or any combination thereof, Z is a hydrogen atom or a halogen atom, and $Z^1$ and $Z^2$ each are a cyclic, linear, or branched alkyl group having 8 to 12 carbon atoms.

In one aspect, the present invention provides an antibacterial compound represented by General Formula (4) or (5) below, or a salt thereof:

General Formula (4)

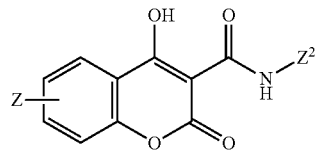

BI

General Formula (5)

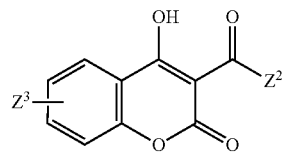

BII where in the General Formulas (4) and (5),
Z represents a hydrogen atom, a halogen atom, an alkoxy group having 1 to 6 carbon atoms, or a hydrocarbon group having 1 to 20 carbon atoms,
$Z^2$ represents a hydrocarbon group which has 5 to 30 carbon atoms and may have a halogen atom, and
$Z^3$ represents a halogen atom, an alkoxy group having 1 to 6 carbon atoms, or a hydrocarbon group having 1 to 20 carbon atoms.

In one variant, the present invention provides a method for producing the compound represented by any one of General Formulas (1) to (3), the tautomer or geometric isomer thereof, or the salt thereof according to the present invention, the method including:
mixing and reacting an oxyindole compound represented by General Formula (6) or (7) below or a 4-hydroxycoumarin compound represented by General Formula (8) below with a carboxylic acid in an organic solvent in the presence of a condensation agent and an amine base, General Formula (6)

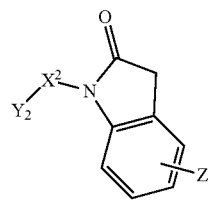

Aa

General Formula (7)

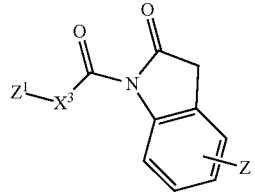

Ab

General Formula (8)

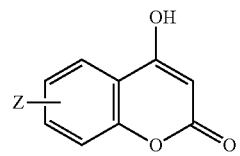

Ba where in the General Formulas (6) to (8),
$Z^1$ represents a cyclic, linear, or branched alkyl group which has 8 to 30 carbon atoms and may have a halogen atom,
$X^2$ represents a single bond, —CO—, —CONH—, or —COO—,
$Y^2$ represents a hydrocarbon group which has 1 to 30 carbon atoms and may have —CN, —NO$_2$, an alkoxy group, a halogen atom, or any combination thereof; or a hydrogen atom,
$X^3$ represents a single bond or —NH—, and
Z represents a hydrogen atom, a halogen atom, an alkoxy group having 1 to 6 carbon atoms, or a hydrocarbon group having 1 to 20 carbon atoms.

In one variant, the present invention provides a method for producing the compound represented by any one of General Formulas (1) to (3), the tautomer or geometric isomer thereof, or the salt thereof according to the present invention, the method including:
mixing and reacting an oxyindole compound represented by General Formula (6) or (7) below or a 4-hydroxycoumarin compound represented by General Formula (8) below with a carboxylic acid chloride in an organic solvent in the presence of an amine base, General Formula (6)

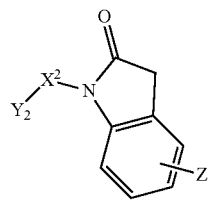

Aa

General Formula (7)

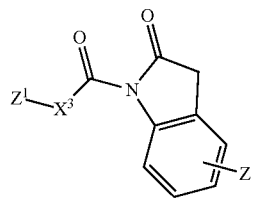

Ab

General Formula (8)

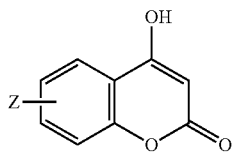

where in the General Formulas (6) to (8),
$Z^1$ represents a cyclic, linear, or branched alkyl group which has 8 to 30 carbon atoms and may have a halogen atom,
$X^2$ represents a single bond, —CO—, —CONH—, or —COO—,
$Y^2$ represents a hydrocarbon group which has 1 to 30 carbon atoms and may have —CN, —NO$_2$, an alkoxy group, a halogen atom, or both thereof; or a hydrogen atom,
$X^3$ represents a single bond or —NH—, and
Z represents a hydrogen atom, a halogen atom, an alkoxy group having 1 to 6 carbon atoms, or a hydrocarbon group having 1 to 20 carbon atoms.

In one variant, the present invention provides a method for producing the compound represented by any one of General Formulas (1) to (3), the tautomer or geometric isomer thereof, or the salt thereof according to the present invention, the method including:
mixing and reacting an oxyindole compound represented by General Formula (6) or (7) below or a 4-hydroxycoumarin compound represented by General Formula (8) below with a carboxylic anhydride in an organic solvent in the presence of an amine base, General Formula (6)

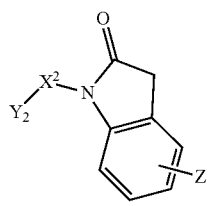

General Formula (7)

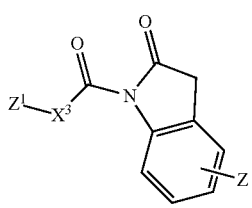

General Formula (8)

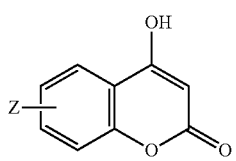

where in the General Formulas (6) to (8),
$Z^1$ represents a cyclic, linear, or branched alkyl group which has 8 to 30 carbon atoms and may have a halogen atom,
$X^2$ represents a single bond, —CO—, —CONH—, or —COO—,
$Y^2$ represents a hydrocarbon group which has 1 to 30 carbon atoms and may have —CN, —NO$_2$, an alkoxy group, a halogen atom, or any combination thereof; or a hydrogen atom,
$X^3$ represents a single bond or —NH—, and
Z represents a hydrogen atom, a halogen atom, an alkoxy group having 1 to 6 carbon atoms, or a hydrocarbon group having 1 to 20 carbon atoms.

In one variant, the present invention provides a method for producing the antibacterial compound represented by General Formula (5) or the salt thereof according to the present invention, the method including:
mixing and reacting a 4-hydroxycoumarin compound represented by General Formula (8) below with a carboxylic acid in an organic solvent in the presence of a condensation agent and an amine base, General Formula (8)

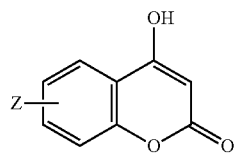

where in the General Formula (8),
Z represents a hydrogen atom, a halogen atom, an alkoxy group having 1 to 6 carbon atoms, or a hydrocarbon group having 1 to 20 carbon atoms.

In one variant, the present invention provides a method for producing the antibacterial compound represented by General Formula (4) or the salt thereof according to the present invention, the method including:
mixing and reacting a 4-hydroxycoumarin compound represented by General Formula (8) below with an isocyanate in an organic solvent in the presence of an amine base, General Formula (8)

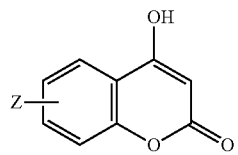

where in the General Formula (8),
Z represents a hydrogen atom, a halogen atom, an alkoxy group having 1 to 6 carbon atoms, or a hydrocarbon group having 1 to 20 carbon atoms.

In one variant, the present invention provides an antibacterial agent, including:
the compound represented by any one of General Formulas (1) to (3), the tautomer or geometric isomer thereof, or the salt thereof according to the present invention.

In one variant, the present invention provides an antibacterial agent, including:

the antibacterial compound represented by General Formulas (4) to (5), or the salt thereof according to the present invention.

In one variant, the present invention provides an infectious disease therapeutic drug, including:

the antibacterial agent including the compound represented by any one of General Formulas (1) to (3) according to the present invention, the antibacterial agent including the compound represented by General Formulas (4) to (5) according to the present invention, or both thereof.

INDUSTRIAL APPLICABILITY

The compound of the present invention has excellent antibacterial activity and can be produced in a simple manner, and thus can suitably be used for prevention or treatment of infectious diseases, in particular those caused by multiply antibiotic-resistant bacteria such as MRSA, VRE, and *Clostridium difficile*.

The invention claimed is:

1. A compound represented by any one of General Formulas (1) to (2) below, a tautomer or geometric isomer thereof, or a salt thereof:

General Formula (1)

AI

General Formula (2)

AII wherein $X^1$ represents a single bond or an alkylene group having 1 to 8 carbon atoms, $Y^1$ represents a single bond, —O—, —NHCO—, —NHCOO—, —S—, —SO—, or —SO$_2$—, $Z^1$ represents a cyclic, linear, or branched alkyl group which has 8 to 30 carbon atoms and may have a halogen atom, $X^2$ represents a single bond, —CO—, —CONH—, or —COO—, $Y^2$ represents a hydrocarbon group which has 1 to 30 carbon atoms and may have —CN, —NO$_2$, an alkoxy group, a halogen atom, or any combination thereof; or a hydrogen atom, $X^3$ represents a single bond or —NH—, Z represents a hydrogen atom, a halogen atom, an alkoxy group having 1 to 6 carbon atoms, or a hydrocarbon group having 1 to 20 carbon atoms, and $R^1$ represents a hydrocarbon group which has 1 to 30 carbon atoms and may have an alkoxy group, —OH, —CN, —NO$_2$, a halogen atom, or any combination thereof.

2. The compound, the tautomer or geometric isomer thereof, or the salt thereof according to claim 1, wherein $X^1$ is a methylene group, $X^2$ is —CO— or —CONH—, $X^3$ is a single bond, $Y^1$ is —O—, $Y^2$ is a methyl group, or a phenyl group which may have, as a substituent, an alkoxy group, a trifluoromethyl group, a halogen atom, or any combination thereof, Z is a hydrogen atom or a halogen atom, and $Z^1$ is a cyclic, linear, or branched alkyl group having 8 to 12 carbon atoms.

3. The compound, the tautomer or geometric isomer thereof, or the salt thereof according to claim 1, wherein $X^1$ is a methylene group, $X^2$ is —CO— or —CONH—, $X^3$ is a single bond, $Y^1$ is —S—, $Y^2$ is a methyl group, or a phenyl group which may have, as a substituent, an alkoxy group, a trifluoromethyl group, a halogen atom, or any combination thereof, Z is a hydrogen atom or a halogen atom, and $Z^1$ is a cyclic, linear, or branched alkyl group having 8 to 12 carbon atoms.

4. The compound, the tautomer or geometric isomer thereof, or the salt thereof according to claim 1, wherein $X^1$, $X^3$, and $Y^1$ each are a single bond, $X^2$ is —CO— or —CONH—, $Y^2$ is a methyl group, or a phenyl group which may have, as a substituent, an alkoxy group, a trifluoromethyl group, a halogen atom, or any combination thereof, Z is a hydrogen atom or a halogen atom, and $Z^1$ is a cyclic, linear, or branched alkyl group having 8 to 12 carbon atoms.

5. A method for producing a compound represented by any one of General Formulas (1) to (2) below, a tautomer or geometric isomer thereof, or a salt thereof, General Formula (1)

AI

General Formula (2)

AII wherein $X^1$ represents a single bond or an alkylene group having 1 to 8 carbon atoms, $Y^1$ represents a single bond, —O—, —NHCO—, —NHCOO—, —S—, —SO—, or —SO$_2$—, $Z^1$ represents a cyclic, linear, or branched alkyl group which has 8 to 30 carbon atoms and may have a halogen atom, $X^2$ represents a single bond, —CO—, —CONH—, or —COO—, $Y^2$ represents a hydrocarbon group which has 1 to 30 carbon atoms and may have —CN, —NO$_2$, an alkoxy group, a halogen atom, or any combination thereof; or a hydrogen atom, $X^3$ represents a single bond or —NH—, Z represents a hydrogen atom, a halogen atom, an alkoxy group having 1 to 6 carbon atoms, or a hydrocarbon group having 1 to 20 carbon atoms, and $R^1$ represents a hydrocarbon group which has 1 to 30 carbon atoms and may have an alkoxy group, —OH, —CN, —NO$_2$, a halogen atom, or any combination thereof, the method comprising:

mixing and reacting an oxyindole compound represented by General Formula (6) or (7) below with a carboxylic acid in an organic solvent in the presence of a condensation agent and an amine base, General Formula (6)

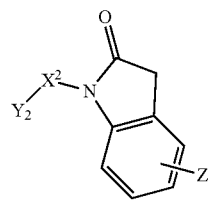

Aa

General Formula (7)

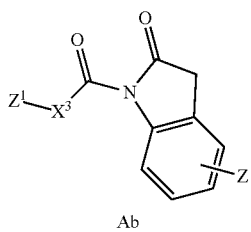

Ab wherein, $Z^1$ represents a cyclic, linear, or branched alkyl group which has 8 to 30 carbon atoms and may have a halogen atom, $X^2$ represents a single bond, —CO—, —CONH—, or —COO—, $Y^2$ represents a hydrocarbon group which has 1 to 30 carbon atoms and may have —CN, —NO$_2$, an alkoxy group, a halogen atom, or any combination thereof; or a hydrogen atom, $X^3$ represents a single bond or —NH—, and Z represents a hydrogen atom, a halogen atom, an alkoxy group having 1 to 6 carbon atoms, or a hydrocarbon group having 1 to 20 carbon atoms.

6. A method for producing a compound represented by any one of General Formulas (1) to (2), below, a tautomer or geometric isomer thereof, or a salt thereof:

General Formula (1)

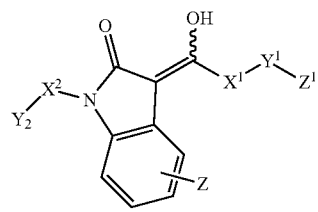

AI

General Formula (2)

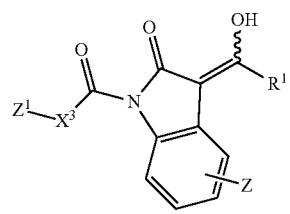

AII wherein $X^1$ represents a single bond or an alkylene group having 1 to 8 carbon atoms, $Y^1$ represents a single bond, —O—, —NHCO—, —NHCOO—, —S—, —SO—, or —SO$_2$—, $Z^1$ represents a cyclic, linear, or branched alkyl group which has 8 to 30 carbon atoms and may have a halogen atom, $X^2$ represents a single bond, —CO—, —CONH—, or —COO—, $Y^2$ represents a hydrocarbon group which has 1 to 30 carbon atoms and may have —CN, —NO$_2$, an alkoxy group, a halogen atom, or any combination thereof; or a hydrogen atom, $X^3$ represents a single bond or —NH—, Z represents a hydrogen atom, a halogen atom, an alkoxy group having 1 to 6 carbon atoms, or a hydrocarbon group having 1 to 20 carbon atoms, and $R^1$ represents a hydrocarbon group which has 1 to 30 carbon atoms and may have an alkoxy group, —OH, —CN, —NO$_2$, a halogen atom, or any combination thereof, the method comprising:

mixing and reacting an oxyindole compound represented by General Formula (6) or (7) below with a carboxylic acid chloride in an organic solvent in the presence of an amine base, General Formula (6)

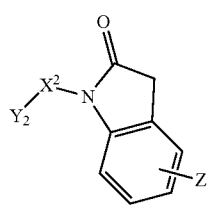

Aa

General Formula (7)

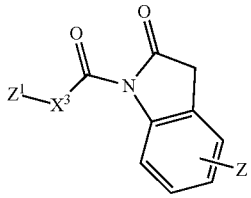

Ab wherein
$Z^1$ represents a cyclic, linear, or branched alkyl group which has 8 to 30 carbon atoms and may have a halogen atom,
$X^2$ represents a single bond, —CO—, —CONH—, or —COO—,
$Y^2$ represents a hydrocarbon group which has 1 to 30 carbon atoms and may have —CN, —NO$_2$, an alkoxy group, a halogen atom, or any combination thereof; or a hydrogen atom,
$X^3$ represents a single bond or —NH—, and
Z represents a hydrogen atom, a halogen atom, an alkoxy group having 1 to 6 carbon atoms, or a hydrocarbon group having 1 to 20 carbon atoms.

7. A method for producing a compound represented by any one of General Formulas (1) to (2) below, a tautomer or geometric isomer thereof, or a salt thereof, General Formula (1)

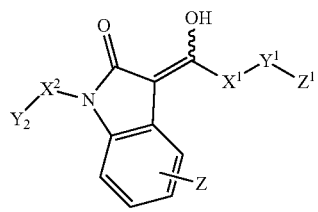

AI

General Formula (2)

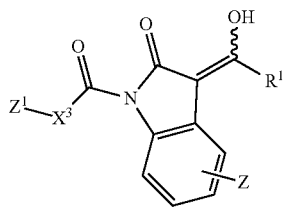

AII wherein
$X^1$ represents a single bond or an alkylene group having 1 to 8 carbon atoms,
$Y^1$ represents a single bond, —O—, —NHCO—, —NHCOO—, —S—, —SO—, or —SO$_2$—,
$Z^1$ represents a cyclic, linear, or branched alkyl group which has 8 to 30 carbon atoms and may have a halogen atom,
$X^2$ represents a single bond, —CO—, —CONH—, or —COO—,
$Y^2$ represents a hydrocarbon group which has 1 to 30 carbon atoms and may have —CN, —NO$_2$, an alkoxy group, a halogen atom, or any combination thereof; or a hydrogen atom, $X^3$ represents a single bond or —NH—,
Z represents a hydrogen atom, a halogen atom, an alkoxy group having 1 to 6 carbon atoms, or a hydrocarbon group having 1 to 20 carbon atoms, and
$R^1$ represents a hydrocarbon group which has 1 to 30 carbon atoms and may have an alkoxy group, —OH, —CN, —NO$_2$, a halogen atom, or any combination thereof,
the method comprising:
mixing and reacting an oxyindole compound represented by General Formula (6) or (7) below with a carboxylic anhydride in an organic solvent in the presence of an amine base, General Formula (6)

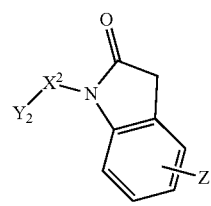

Aa

General Formula (7)

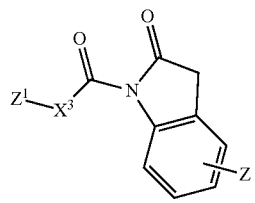

Ab wherein
$Z^1$ represents a cyclic, linear, or branched alkyl group which has 8 to 30 carbon atoms and may have a halogen atom,
$X^2$ represents a single bond, —CO—, —CONH—, or —COO—,
$Y^2$ represents a hydrocarbon group which has 1 to 30 carbon atoms and may have —CN, —NO$_2$, an alkoxy group, a halogen atom, or any combination thereof; or a hydrogen atom,
$X^3$ represents a single bond or —NH—, and
Z represents a hydrogen atom, a halogen atom, an alkoxy group having 1 to 6 carbon atoms, or a hydrocarbon group having 1 to 20 carbon atoms.

8. An antibacterial agent, comprising:
a compound, represented by any one of General Formulas (1) to (2) below, a tautomer or geometric isomer thereof, or a salt thereof:

General Formula (1)

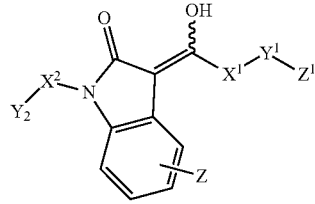

AI

-continued

General Formula (2)

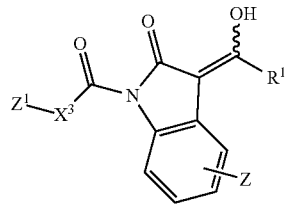

AII

General Formula (1)

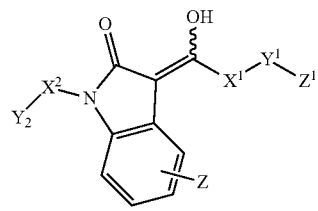

AI

General Formula (2)

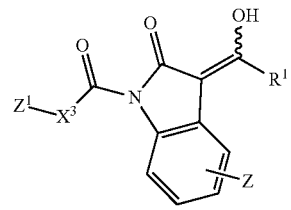

AII wherein, $X^1$ represents a single bond or an alkylene group having 1 to 8 carbon atoms, $Y^1$ represents a single bond, —O—, —NHCO—, —NHCOO—, —S—, —SO—, or —SO$_2$—, $Z^1$ represents a cyclic, linear, or branched alkyl group which has 8 to 30 carbon atoms and may have a halogen atom, $X^2$ represents a single bond, —CO—, —CONH—, or —COO—, $Y^2$ represents a hydrocarbon group which has 1 to 30 carbon atoms and may have —CN, —NO$_2$, an alkoxy group, a halogen atom, or any combination thereof; or a hydrogen atom, $X^3$ represents a single bond or —NH—, Z represents a hydrogen atom, a halogen atom, an alkoxy group having 1 to 6 carbon atoms, or a hydrocarbon group having 1 to 20 carbon atoms, and $R^1$ represents a hydrocarbon group which has 1 to 30 carbon atoms and may have an alkoxy group, —OH, —CN, —NO$_2$, a halogen atom, or any combination thereof.

9. An infectious disease therapeutic drug, comprising:

an antibacterial agent wherein the antibacterial agent comprises:

a compound represented by any one of General Formulas (1) to (2) below, a tautomer or geometric isomer thereof, or a salt thereof, wherein, $X^1$ represents a single bond or an alkylene group having 1 to 8 carbon atoms, $Y^1$ represents a single bond, —O—, —NHCO—, —NHCOO—, —S—, —SO—, or —SO$_2$—, $Z^1$ represents a cyclic, linear, or branched alkyl group which has 8 to 30 carbon atoms and may have a halogen atom, $X^2$ represents a single bond, —CO—, —CONH—, or —COO—, $Y^2$ represents a hydrocarbon group which has 1 to 30 carbon atoms and may have —CN, —NO$_2$, an alkoxy group, a halogen atom, or any combination thereof; or a hydrogen atom, $X^3$ represents a single bond or —NH—, Z represents a hydrogen atom, a halogen atom, an alkoxy group having 1 to 6 carbon atoms, or a hydrocarbon group having 1 to 20 carbon atoms, and $R^1$ represents a hydrocarbon group which has 1 to 30 carbon atoms and may have an alkoxy group, —OH, —CN, —NO$_2$, a halogen atom, or any combination thereof.

* * * * *